US007255881B2

(12) United States Patent
Gillis et al.

(10) Patent No.: US 7,255,881 B2
(45) Date of Patent: Aug. 14, 2007

(54) METAL-CONTAINING MATERIALS

(75) Inventors: Scott H. Gillis, Concord, MA (US); Paul Schechter, Dover, MA (US); James Alexander Robert Stiles, Toronto (CA)

(73) Assignee: Nucryst Pharmaceuticals Corp., Fort Saskatchewan, Alberta (CA)

( * ) Notice: Subject to any disclaimer, the term of this patent is extended or adjusted under 35 U.S.C. 154(b) by 459 days.

(21) Appl. No.: 10/690,774

(22) Filed: Oct. 22, 2003

(65) Prior Publication Data

US 2004/0129112 A1    Jul. 8, 2004

Related U.S. Application Data

(63) Continuation-in-part of application No. 09/916,757, filed on Jul. 27, 2001, now Pat. No. 6,692,773, which is a continuation-in-part of application No. 09/628,735, filed on Jul. 27, 2000, now abandoned, application No. 10/690,774, which is a continuation-in-part of application No. 10/159,587, filed on May 30, 2002, now Pat. No. 7,001,617, which is a continuation-in-part of application No. 10/131,568, filed on Apr. 23, 2002, now abandoned, which is a continuation-in-part of application No. 09/840,637, filed on Apr. 23, 2001, now Pat. No. 7,008,647, application No. 10/690,774, which is a continuation-in-part of application No. 10/131,511, filed on Apr. 23, 2002, now Pat. No. 6,939,568, which is a continuation-in-part of application No. 09/840,637, filed on Apr. 23, 2001, now Pat. No. 7,008,647, application No. 10/690,774, which is a continuation-in-part of application No. 10/131,509, filed on Apr. 23, 2002, now Pat. No. 7,087,249, which is a continuation-in-part of application No. 09/840,637, filed on Apr. 23, 2001, now Pat. No. 7,008,647, application No. 10/690,774, which is a continuation-in-part of application No. 10/128,208, filed on Apr. 23, 2002, now Pat. No. 6,989,156, which is a continuation-in-part of application No. 09/840,637, filed on Apr. 23, 2001, now Pat. No. 7,008,647, application No. 10/690,774, which is a continuation-in-part of application No. 10/277,673, filed on Oct. 22, 2002, now abandoned, and a continuation-in-part of application No. 10/277,356, filed on Oct. 22, 2002, now abandoned, and a continuation-in-part of application No. 10/277,298, filed on Oct. 22, 2002, now Pat. No. 6,989,157, and a continuation-in-part of application No. 10/277,362, filed on Oct. 22, 2002, now abandoned, and a continuation-in-part of application No. 10/277,358, filed on Oct. 22, 2002, now abandoned, and a continuation-in-part of application No. 10/277,320, filed on Oct. 22, 2002, now abandoned.

(60) Provisional application No. 60/285,884, filed on Apr. 23, 2001.

(51) Int. Cl.
| | |
|---|---|
| *A61K 9/02* | (2006.01) |
| *A61K 9/14* | (2006.01) |
| *A61K 31/28* | (2006.01) |
| *A61K 31/282* | (2006.01) |
| *A61K 33/00* | (2006.01) |
| *A61K 33/24* | (2006.01) |
| *A61K 33/38* | (2006.01) |
| *A61K 33/42* | (2006.01) |

(52) U.S. Cl. ............... 424/618; 424/604; 424/619; 424/646; 424/649; 424/430; 424/433; 424/436; 424/489; 514/492; 514/495; 514/951; 514/966; 514/967; 514/968

(58) Field of Classification Search ............ 424/447, 424/451, 457, 464, 468, 489, 618, 649, 646, 424/430, 433, 436, 604, 619; 514/492, 495, 514/951, 966, 967, 968
See application file for complete search history.

(56) References Cited

U.S. PATENT DOCUMENTS

| | | |
|---|---|---|
| 3,757,786 A | 9/1973 | Smith |
| 3,800,792 A | 4/1974 | McKnight et al. |
| 3,918,446 A | 11/1975 | Buttaravoli |
| 4,059,105 A | 11/1977 | Citruzzula et al. |
| 4,324,237 A | 4/1982 | Buttaravoli |
| 4,355,636 A | 10/1982 | Oetjen et al. |
| 4,376,764 A | 3/1983 | Schmolka |
| 4,393,048 A | 7/1983 | Mason, Jr. et al. |
| 4,476,590 A | 10/1984 | Scales et al. |
| 4,581,028 A | 4/1986 | Fox, Jr. et al. |
| 4,596,556 A | 6/1986 | Morrow et al. |
| 4,633,863 A | 1/1987 | Filips et al. |
| 4,749,572 A | 6/1988 | Ahari |
| 4,790,824 A | 12/1988 | Morrow et al. |

(Continued)

FOREIGN PATENT DOCUMENTS

| CA | 2242033 | 1/1999 |
|---|---|---|

(Continued)

OTHER PUBLICATIONS

HCAPLUS Abstract, accession No. 1995:331180 (1995).*

(Continued)

*Primary Examiner*—John Pak
(74) *Attorney, Agent, or Firm*—Fish & Richardson P.C.

(57) ABSTRACT

Metal-containing materials, as well as their preparation and use are disclosed. The metal-containing material can be, for example, an antimicrobial material, an anti-biofilm material, an antibacterial material, an anti-inflammatory material, an anti-fungal material, an anti-viral material, an anti-cancer material, a pro-apoptosis material, anti-proliferative, MMP modulating material, an atomically disordered, crystalline material, and/or a nanocrystalline material. In certain embodiments, the metal-containing material is an atomically disordered, nanocrystalline silver-containing material.

6 Claims, 5 Drawing Sheets

U.S. PATENT DOCUMENTS

| | | | |
|---|---|---|---|
| 4,803,066 A | 2/1989 | Edwards | |
| 4,828,832 A | 5/1989 | De Cuellar et al. | |
| 4,847,049 A | 7/1989 | Yamamoto | |
| 4,908,355 A | 3/1990 | Gettings et al. | |
| 4,952,411 A | 8/1990 | Fox, Jr. et al. | |
| 4,960,413 A | 10/1990 | Sagar et al. | |
| 4,980,172 A * | 12/1990 | Fey | 424/485 |
| 5,019,096 A | 5/1991 | Fox, Jr. et al. | |
| 5,064,413 A | 11/1991 | McKinnon et al. | |
| 5,122,418 A | 6/1992 | Nakane et al. | |
| 5,143,717 A | 9/1992 | Davis | |
| 5,236,421 A | 8/1993 | Becher | |
| 5,240,914 A | 8/1993 | Rubin | |
| 5,270,358 A | 12/1993 | Asmus | |
| 5,275,827 A | 1/1994 | Spinelli et al. | |
| 5,312,335 A | 5/1994 | McKinnon et al. | |
| D349,958 S | 8/1994 | Hollis et al. | |
| 5,369,155 A | 11/1994 | Asmus | |
| 5,372,589 A | 12/1994 | Davis | |
| 5,374,432 A | 12/1994 | Fox et al. | |
| 5,383,851 A | 1/1995 | McKinnon, Jr. et al. | |
| 5,399,163 A | 3/1995 | Peterson et al. | |
| 5,454,886 A | 10/1995 | Burrell et al. | |
| 5,454,889 A | 10/1995 | McNicol et al. | |
| 5,457,015 A | 10/1995 | Boston | |
| 5,520,639 A | 5/1996 | Peterson et al. | |
| 5,534,288 A | 7/1996 | Gruskin et al. | |
| 5,563,132 A | 10/1996 | Bodaness | |
| 5,569,207 A | 10/1996 | Gisselberg et al. | |
| 5,578,073 A | 11/1996 | Haimovich et al. | |
| 5,631,066 A | 5/1997 | O'Brien | |
| 5,681,575 A | 10/1997 | Burrell et al. | |
| 5,744,151 A | 4/1998 | Capelli | |
| 5,753,251 A | 5/1998 | Burrell et al. | |
| 5,770,255 A | 6/1998 | Burrell et al. | |
| 5,770,258 A | 6/1998 | Takizawa | |
| 5,792,793 A | 8/1998 | Oda et al. | |
| 5,837,275 A | 11/1998 | Burrell et al. | |
| 5,848,995 A | 12/1998 | Walder | |
| 5,895,419 A | 4/1999 | Tweden et al. | |
| 5,899,880 A | 5/1999 | Bellhouse et al. | |
| 5,945,032 A | 8/1999 | Breitenbach et al. | |
| 5,958,440 A | 9/1999 | Burrell et al. | |
| 5,981,822 A | 11/1999 | Addison | |
| 5,985,308 A | 11/1999 | Burrell et al. | |
| 6,010,478 A | 1/2000 | Bellhouse et al. | |
| 6,013,050 A | 1/2000 | Bellhouse et al. | |
| 6,017,553 A | 1/2000 | Burrell et al. | |
| 6,022,547 A | 2/2000 | Herb et al. | |
| 6,071,541 A | 6/2000 | Murad | |
| 6,071,543 A | 6/2000 | Thornfeldt | |
| 6,096,002 A | 8/2000 | Landau | |
| 6,123,925 A | 9/2000 | Barry et al. | |
| 6,126,931 A | 10/2000 | Sawan et al. | |
| 6,165,440 A | 12/2000 | Esenaliev | |
| 6,187,290 B1 | 2/2001 | Gilchrist et al. | |
| 6,197,351 B1 | 3/2001 | Neuwirth | |
| 6,201,164 B1 | 3/2001 | Wulff et al. | |
| 6,224,779 B1 * | 5/2001 | Spector | 210/754 |
| 6,224,898 B1 | 5/2001 | Balogh et al. | |
| 6,238,686 B1 | 5/2001 | Burrell et al. | |
| 6,258,385 B1 | 7/2001 | Antelman | |
| 6,277,169 B1 | 8/2001 | Hampden-Smith et al. | |
| 6,294,186 B1 | 9/2001 | Beerse et al. | |
| 6,333,093 B1 | 12/2001 | Burrell et al. | |
| 6,365,130 B1 | 4/2002 | Barry et al. | |
| 6,720,006 B2 | 4/2004 | Hanke et al. | |
| 2001/0010016 A1 | 7/2001 | Modak et al. | |
| 2002/0001628 A1 | 1/2002 | Ito | |
| 2002/0016585 A1 | 2/2002 | Sachse | |
| 2002/0025344 A1 | 2/2002 | Newman et al. | |
| 2002/0045049 A1 | 4/2002 | Madsen | |
| 2002/0051824 A1 | 5/2002 | Burrell et al. | |
| 2002/0192298 A1 | 12/2002 | Burrell et al. | |

FOREIGN PATENT DOCUMENTS

| | | |
|---|---|---|
| CN | 1082645 | 2/1994 |
| CN | 1241662 | 1/2000 |
| CN | 1262093 | 8/2000 |
| CN | 1279222 | 1/2001 |
| CN | 1291666 | 4/2001 |
| CN | 1291667 | 4/2001 |
| CN | 1306117 | 8/2001 |
| CN | 1322474 | 11/2001 |
| CN | 1322874 | 11/2001 |
| CN | 1328819 | 1/2002 |
| CN | 1328827 | 1/2002 |
| DE | 2748882 | 5/1979 |
| DE | 3807944 | 9/1989 |
| DE | 195 41 735 A1 | 5/1997 |
| EP | 0 136 768 | 4/1985 |
| EP | 0 254 413 | 1/1988 |
| EP | 0 356 060 | 8/1989 |
| EP | 0 355 009 | 2/1990 |
| EP | 0 378 147 | 7/1990 |
| EP | 0 599 188 | 6/1994 |
| EP | 0681841 | 11/1995 |
| EP | 0780138 | 6/1997 |
| EP | 0 328 421 A2 | 8/1999 |
| EP | 1 159 972 | 12/2001 |
| GB | 420052 | 11/1934 |
| GB | 427106 | 4/1935 |
| GB | 965010 | 7/1964 |
| GB | 1270410 | 4/1972 |
| GB | 2 073 024 | 10/1981 |
| GB | 2 140 684 | 12/1984 |
| HU | 980078 A | 9/1999 |
| IT | 022309 | 12/1990 |
| JP | 60-21912 | 2/1985 |
| JP | SHO 58-126910 | 2/1985 |
| JP | 04244029 A | 9/1992 |
| JP | 11060493 | 3/1999 |
| JP | 11116488 | 4/1999 |
| JP | 11124335 | 5/1999 |
| JP | 2000327578 | 11/2000 |
| WO | 87/07251 | 12/1987 |
| WO | WO89/09054 | 10/1989 |
| WO | 92/13491 | 8/1992 |
| WO | 93/23092 | 11/1993 |
| WO | 95/13704 | 5/1995 |
| WO | WO95/13704 A | 5/1995 |
| WO | WO96/17595 | 6/1996 |
| WO | 98/41095 | 9/1998 |
| WO | 98/51273 | 11/1998 |
| WO | WO 00/27390 | 5/2000 |
| WO | 00/30697 | 6/2000 |
| WO | 00/44414 | 8/2000 |
| WO | 00/64505 | 11/2000 |
| WO | 00/64506 | 11/2000 |
| WO | 00/78282 | 12/2000 |
| WO | WO 00/78281 | 12/2000 |
| WO | 01/24839 | 4/2001 |
| WO | 01/27365 | 4/2001 |
| WO | WO 01/26627 | 4/2001 |
| WO | 01/34686 | 5/2001 |
| WO | 01/41774 | 6/2001 |
| WO | 01/41819 | 6/2001 |
| WO | 01/43788 | 6/2001 |
| WO | 01/49115 | 7/2001 |
| WO | 01/49302 | 7/2001 |
| WO | WO 01/49301 | 7/2001 |
| WO | WO 01/49303 A | 7/2001 |
| WO | 01/68179 A1 | 9/2001 |

| | | |
|---|---|---|
| WO | 01/70052 | 9/2001 |
| WO | 01/74300 | 10/2001 |
| WO | 01/80920 | 11/2001 |
| WO | 02/15698 | 2/2002 |
| WO | WO 02/09729 A2 | 2/2002 |
| WO | 02/18003 | 3/2002 |
| WO | 02/18699 | 3/2002 |
| WO | 02/44625 | 6/2002 |
| WO | 02/085299 A2 | 10/2002 |
| WO | 02/085384 A2 | 10/2002 |
| WO | 02/085385 A2 | 10/2002 |
| WO | 02/085386 A2 | 10/2002 |
| WO | 02/085387 A2 | 10/2002 |

OTHER PUBLICATIONS

Stedman's Medical Dictionary, 26th ed., Williams & Wilkins, Baltimore, 1995, pp. 1706-1707.*

Melloni et al., Melloni's Pocket Medical Dictionary, The Parthenon Publishing Group, New York, Dec. 2003, p. 451.*

Becker, Robert O. et al., "Treatment of Orthopaedic Infections with Electrically Generated Silver Ions, *The Journal of Bone and Joint Surgery, American*" 60-A(7):871-881 (Oct. 1978).

Berger, T.J., et al., "Electrically Generated Silver Ions: Quantitative Effects on Bacterial and Mammalian Cells," *Antimicrobial Agents and Chemotherapy* 357-358 (Feb. 1976).

Burrell, et al. "Efficacy of Silver-Coated Dressings as Bacterial Barriers in a Rodent Burn Sepsis Model" *Wounds* 1999; 11(4): 64-71.

Colmano, G., DVM, PhD, et al, Activation of Antibacterial Silver Coatings on Surgical Implants by Direct Current: Preliminary Studies in Rabbits, *Microbiology* 41(6):964-966 (1980) [Bracken Library, Queen's University, Kingston, Ontario].

Davis, C.P., et al., "Effects of Microamperage, Medium, and Bacterial Concentration on Iontophoretic Killing of Bacteria in Fluid," *Antimicrobial Agents and Chemotherapy* 442-447 (Apr. 1989).

Deitch, Edwin A., et al., "Silver Nylon Cloth: In vitro and in vivo Evaluation of Antimicrobial Activity," *The Journal of Trauma* 27(3):301-304 (1987).

Deitch, Edwin A., et al., "Silver-Nylon: A New Antimicrobial Agent," *Antimicrobial Agents and Chemotherapy* 356-359 (Mar. 1983).

Demling, et al., "The Role of Silver in Wound Healing: Effects of Silver on Wound Management," *Wounds*, vol. 13, No. 1, Jan./Feb. 2001 Supplement A; pp. 5-14.

Djokic et al., "An Electrochemical Analysis of Thin Silver Films Produced by Reactive Sputtering", *Journal of The Electrochemical Society*, 148 (3) C191-C196 (2001).

Falcone, Alfred, E., D.D.S., M.D., et al., "Inhibitory Effects of Electrically Activated Silver Material on Cutaneous Would Bacteria," *Plactic and Reconstructive Surgery* 455-459 (Mar. 1986).

Grier, N., Ph.D., "Silver and Its Compounds" in Antiseptics and Disinfectants 375-389 (1977). (S.S. Block, Lea and Febiger).

Hall, Richard, E., D.D.S., M.S., Ph.D., et al., "Inhibitory and cidal Antimicrobial Actions of Electrically Generated Silver Ions," *J. Oral Maxillofax Surg.*, 45:779-784 (1987).

Kirsner, et al., "The Role of Silver in Wound Healing: Matrix Metalloproteinases in Normal and Impaired Wound Healing: A Potential Role of Nanocrystalline Silver," *Wounds*, vol. 13, No. 3, May/Jun. 2001, Supplement C pp. 5-12.

Liedberg, H., et al., "Silver Alloy Coated Catheters Reduce Catheter-Associated Bacteriuria," *Br. J. Urol.* 65(4):379-381 (Apr. 1990).

MacKeen et al., "Silver-Coated Nylon Fiber as an Antibacterial Agent," *Antimicrobial Agents and Chemotherapy* 31(1):93-99 (Jan. 1987).

Olson et al., "Healing of Porcine Donor sites Covered with Silver-coated Dressings"* *Eur J Surg* 2000; 166:486-489.

Ovington, "The Role of Silver in Wound Healing: Why is Nanocrystalline Silver Superior? Nanocrystalline Silver: Where the Old and Familiar Meets a New Frontier," *Wounds*, vol. 13, No. 2, Mar./Apr. 2001, Supplement B; pp. 5-10.

Sant et al., "Morphology of Novel Antimicrobial Silver Films Deposited By Magnetron Sputtering" Scripta Materiala, vol. 41, No. 12, pp. 1333-1339, Nov. 19, 1999.

Sant et al., "Novel duplex antimicrobial silver films deposited by magnetron sputtering", *Philosophical Magazine Letters*, 2000, vol. 80, No. 4, 249-256.

Shigemasa et al., "Applications of Chitin and Chitosan for Biomaterials" *Biotechnology & Genetic Engineering Reviews* vol. 13 (14) pp. 383-420.

Spadara, J.A., et al., "Silver Polymethyl Methacrylate Antibacterial Bone Cement," *Clinical Orthopaedics and Related Research* 143:266-270 (Sep. 1979).

Spadaro, J.A., et al., "Antibacterial Effects of Silver Electrode," *IEEE, Eng., in Med. & Biol. Soc.* 215-218 (1981).

Thibodeau, E.A. et al., "Inhibition and Killing of Oral Bacteria by Silver Ions Generated with Low Intensity Direct Current," *Journal of Dental Research* 57(9-10):922-926 (1978).

Thornton, "Deposition Technologies for Films and Coatings: Coating Deposition by Sputtering" *Materials Science Series* 5 pp. 170-243 1982.

Thornton, "Influence of apparatus geometry and deposition conditions on the structure and topography of thick sputtered coatings" *J. Vac. Sci. Technol.*, vol. 11, No. 4, Jul./Aug. 1974.

Tredget, "Evaluation of Wound Healing using Silver Dressing", Feb. 22, 1996.

Tredget et al., "A Matched-Pair, Randomized Study Evaluating the Efficacy and Safety of Acticoat* Silver-Coated Dressing for the Treatment of Burn Wounds," *Journal of Burn Care & Rehabilitation* Nov./Dec. 1998; 19:531-7.

Voigt, et al., "The Use of Acticoat as Silver Impregnated Telfa Dressings in a Regional Burn and Wound Care Center: The Clinicians View," *Wounds*, vol. 13, No. 2, Mar./Apr. 2001, Supplement B; pp. 11-20.

Wright et al., "Early healing events in a porcine model of contaminated wounds: effects of nanocrystalline silver on matrix metalloproteinases, cell apoptosis, and healing" *Wound Repair and Regeneration* 2002; 10:141-151.

Wright, et al., "The Comparative Efficacy of Two Antimicrobial Barrier Dressings: In-vitro Examination of Two Controlled Release of Silver Dressings" *Wounds* vol. 10, No. 6, Nov./Dec. 1998, pp. 179-188.

Wright, et al., "Efficacy of topical silver against fungal burn wound pathogens", *AJIC* vol. 27, No. 4, Aug. 1999.

Wright, et al., "Wound Management in an era of increasing bacterial antibiotic resistance: A role for topical silver treatment," *AJIC* vol. 26, No. 6; pp. 572-577 Dec. 1998.

Yin et al., "Comparative Evaluation of the Antimicrobial Activity of ACTICOAT* Antimicrobial Barrier Dressing" *Journal of Burn Care & Rehabilitation*. vol. 20, No. 3 May/Jun. 1999.

Yin, et al., "Effect of Acticoat Antimicrobial Barrier Dressing on Wound Healing and Graft Take", *Burn Care & Rehabilitation*, part 2 Jan./Feb. 1999.

Database Derwent on West, 197331. Derwent Publication Ltd., Accession No. 1973: 42926U, DE 2200723 A. Fresenious Chemisc-Pharm abstract.

WPIDS abstract 1966-11488F (1966).

WPIDS abstract 1989-312257 (1989).

Medline abstract, accession No. 96064219 (1996).

Hoet, Peter H.M. et al., "Nanoparticles—known and unknown health risks," Journal of Nanobiotechnology, vol. 2, pp. 1-15, 2004.

Borm, Paul J. A. et al., Toxicological hazards of inhaled nanoparticles—potential implications for drug delivery, Journal of Nanoscience and Nanotechnology, vol. 4(5), pp. 521-531, 2004.

Ozkan, M., "Quantum dots and other nonparticles: what can they offer to drug discovery"? Drug Discovery Today, vol. 9(24), pp. 1065-1071, 2004.

Williams, D., "Nanocrystalline metals: another opportunity for medical devices?" Medical Device Technology, vol. 14(9), p. 12 (pp. 1-4 in the copy obtained via ProQuest), 2003.

Grier, N., Ph.D., "Silver and Its Compounds", Disinfection, Sterilization and Preservation, pp. 395-407, 1977, (S.S. Block, Lea and Febiger).

* cited by examiner

METAL-CONTAINING MATERIALS

CROSS-REFERENCE TO RELATED APPLICATIONS

This application is a continuation-in-part of and claims the benefit of priority under 35 U.S.C. §120 to U.S. patent application Ser. No. 09/916,757, filed Jul. 27, 2001, now U.S. Pat. No. 6,692,773, which is a continuation-in-part of U.S. Pat. application Ser. No. 09/628,735, filed Jul. 27, 2000, now abandoned. This application is also a continuation-in-part of U.S. patent application Ser. No. 10/159,587, filed May 30, 2002, now U.S. Pat. No. 7,001,617, which is a continuation-in-part of U.S. patent application Ser. No. 10/131,568, filed Apr. 23, 2002, now abandoned, which is a continuation-in-part of U.S. patent application Ser. No. 09/840,637, filed on Apr. 23, 2001, now U.S. Pat. No. 7,008,647, and also claims the benefit of U.S. Provisional Application Ser. No. 60/285,884, filed Apr. 23, 2001. This application is also a continuation-in-part of U.S. patent application Ser. No. 10/131,511, filed Apr. 23, 2002, now U.S. Pat. No. 6,939,568, which is a continuation-in-part of U.S. patent application Ser. No. 09/840,637, filed Apr. 23, 2001, now U.S. Pat. No. 7,008,647, and also claims the benefit of U.S. Provisional Application Ser. No. 60/285,884, filed Apr. 23, 2001. This application is also a continuation-in-part of U.S. patent application Ser. No. 10/131,509, filed Apr. 23, 2002, now U.S. Pat. No. 7,087,249, which is a continuation-in-part of U.S. patent application Ser. No. 09/840,637, filed Apr. 23, 2001, now U.S. Pat. No. 7,008,647, and also claims the benefit of U.S. Provisional Application Ser. No. 60/285,884, filed Apr. 23 2001. This application is also a continuation-in-part of U.S. patent application Ser. No. 10/128,208, filed Apr. 23, 2002, now U.S. Pat. No. 6,989,156, which is a continuation-in-part of U.S. patent application Ser. No. 09/840,637, filed Apr. 23, 2001, now U.S. Pat. No. 7,008,647, and also claims the benefit of U.S. Provisional Application Ser. No. 60/285,884, filed Apr. 23, 2001. This application is also a continuation-in-part of U.S. patent application Ser. No. 10/277,673, filed Oct. 22, 2002, now abandoned, U.S. patent application Ser. No. 10/277,356, filed Oct. 22, 2002, now abandoned, U.S. patent application Ser. No. 10/277,298, filed Oct. 22, 2002, now U.S. Pat. No. 6,989,157, U.S. patent application Ser. No. 10/277,362, filed Oct. 22, 2002, now abandoned, U.S. patent application Ser. No. 10/277,358, filed Oct. 22, 2002, now abandoned, and U.S. patent application Ser. No. 10/277,320, filed Oct. 22, 2002, now abandoned. Each of these applications is incorporated by reference.

TECHNICAL FIELD

The invention relates to metal-containing materials, as well as their preparation and use.

BACKGROUND

It is generally desirable to treat a subject (e.g., a human) that has an undesirable condition. Many different compositions have been developed to treat undesirable conditions. For example, certain forms of silver have been reported to be effective in treating some undesirable skin conditions.

SUMMARY

The invention relates to metal-containing materials, as well as their preparation and use.

In one aspect, the invention features a nanocrystalline material that includes a metal and at least one atomic percent of a different element. The element can be, for example, oxygen, nitrogen, carbon, boron, sulfur, phosphorus, silicon, a halogen and/or hydrogen.

In another aspect, the invention features a atomically disordered, crystalline material that includes a metal and at least one atomic percent of a different element. The element can be, for example, oxygen, nitrogen, carbon, boron, sulfur, phosphorus, silicon, a halogen and/or hydrogen.

Embodiments can include one or more of the following features.

In some embodiments, the material can include at most about 90 weight percent of the element.

In certain embodiments, the material can in the form of a free-standing powder.

In some embodiments, the material can be contained within a composition that further includes a pharmaceutically acceptable carrier.

In certain embodiments, the material can be contained within a solution that further includes a solvent.

In some embodiments, the material can be in the form of an aerosol.

In certain embodiments, the material can be contained in a composition that further includes a hydrocolloid.

In some embodiments, the material can be contained in an article in the form of a tape, a pill, a capsule, a tablet, a lozenge or a suppository.

In certain embodiments, the material can be in the form of an article including a substrate and a coating, and the nanocrystalline material is in the coating.

In some embodiments, the material can be in the form of an agglomerate of clusters of atoms.

In certain embodiments, the material can be an atomically disordered, crystalline material and/or a nanocrystalline material.

In some embodiments, the material can be an antimicrobial material, an antibacterial material, an anti-inflammatory materials, an antifungal material, an antiviral material, an anti-autoimmune material, an anti-cancer material, a pro-apoptosis material, an MMP modulating material, and/or an anti-proliferative material.

In certain embodiments, the metal can be silver.

In some embodiments, the material can include at least two different metal elements.

Other features and advantages of the methods will be apparent from the description and drawings, and from the claims.

DETAILED DESCRIPTION

Figure 1:
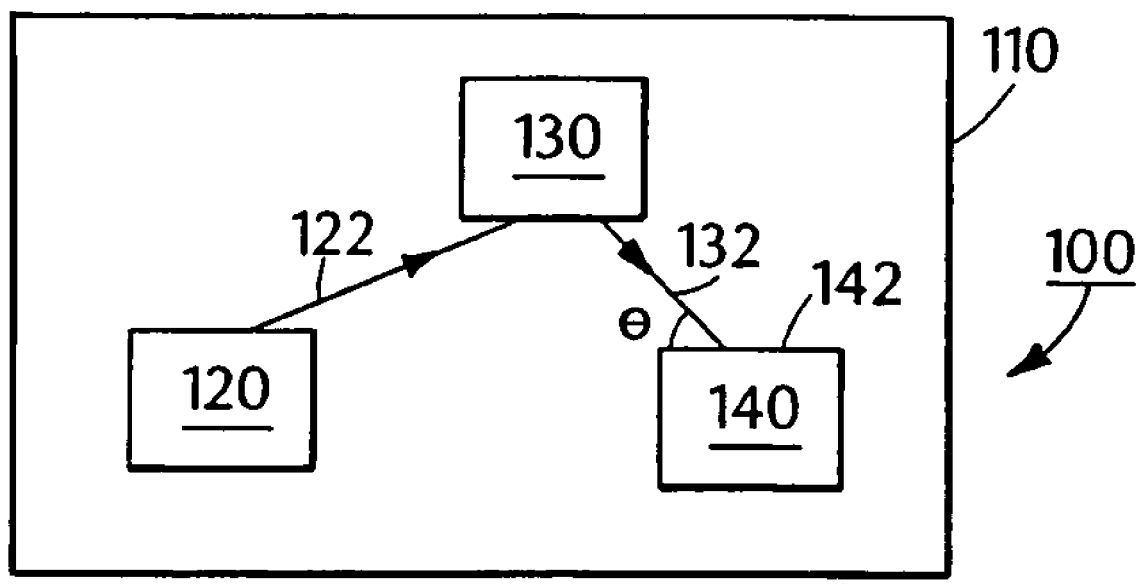
FIG. 1 is a schematic view of a deposition system.
Figure 2:
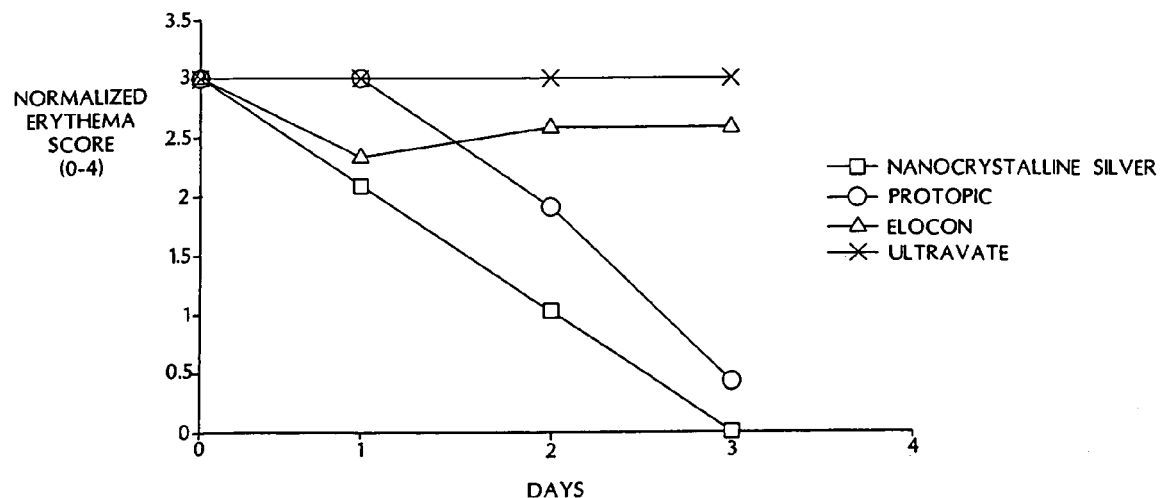
FIG. 2 is a graph showing the efficacy of different forms of silver on erythema.

The inventors have discovered that certain metal-containing materials (e.g., antimicrobial, atomically disordered, nanocrystalline silver-containing materials) can be used to treat a subject with a condition by contacting an area of the subject having the condition with the metal-containing material. As explained below, the metal-containing material can be in any of a variety of forms when delivered to a subject, and the metal-containing material can be delivered to a subject in a variety of ways. As also explained below, the metal-containing material can be used to treat various subjects, conditions, and condition locations.

Without wishing to be bound by theory, it is believed that the therapeutic properties of the metal-containing materials may be explained by one or more potential mechanisms. In one potential mechanism (e.g., at relatively high pH), it is believed that the metal-containing material (e.g., antimicrobial, atomically disordered, nanocrystalline silver-containing materials) forms one or more metastable, relatively high level metal hydroxide species (e.g., $Ag(OH)_4^{3-}$, $Ag(OH)_6^{3-}$) that either directly or indirectly (e.g., via the formation of one or more biological mediators) provide the observed therapeutic properties. In another potential mechanism, it is believed that the metal-containing material is capable of releasing clusters of the metal (e.g., clusters of $Ag^0$, clusters of $Ag^+$, clusters containing both $Ag^+$ and $Ag^0$) that provide the observed therapeutic properties. In a further potential mechanism, it is believed that the concentration of silver in a solution can be raised above the saturation concentration of bare silver ions (e.g., to provide a relatively sustaining reservoir of silver as bare silver ions are consumed). It is believed that, as the bare silver ions are consumed, some of the other silver-containing species can decompose to create additional bare silver ions in accordance with chemical equilibria. It is also believed that the presence of silver in one or more forms other than bare silver ions may raise the level for the effective silver concentration that is nonharmful (e.g., non-toxic) to the cells of a subject (e.g., a human). In an additional potential mechanism, it is believed that one or more forms of silver complexes may be capable of penetrating cellular membranes (e.g., by mimicking species that are normally transported through the membranes), which may accelerate the permeation of silver into the cells. In general, it is believed that the form of the silver-containing species contained in an aqueous solution depends on the solution pH and/or the concentrations of the various silver-containing species in the solid form of the silver-containing material. It is believed that, in general, at low pH the dominant species is a bare silver ion, but that at higher pH, where the solubility of bare silver ions is believed to be limited by the solubility of silver hydroxide, other types of species including complexed silver ions and/or silver-containing clusters become increasingly stable provided that the concentration of bare silver ions remains at the saturation concentration. It is also believed that the nature and relative population of the silver-containing species can depend on the rate at which the species can dissolve from the solid silver-bearing material and the rate at which the species can react with one another in the solution. It is believed that combinations of potential mechanisms may result in the observed therapeutic effect of the metal-containing material.

In general, clusters refer to relatively small groups of atoms, ions or the like. For example, a cluster can contain at least two (e.g., at least three, at least four, at least five, at least six, at least seven, at least eight, at least nine, at least 10, at least 11, at least 12, at least 13, at least 14, at least 15, at least 20, at least 30, at least 40, at least 50, at least 60 at least 70, at least 80, at least 90) atoms, ions or the like, and/or at most 1,000 (e.g., at most 900, at most 800, at most 700, at most 600, at most 500, at most 400, at most 300, at most 200, at most 100) atoms, ions or the like. Clusters are described, for example, in R. P. Andres et al., "Research Opportunities on Cluster and Cluster-Assembled Materials", J. Mater. Res. Vol. 4, No 3, 1989, p. 704. In certain embodiments, a cluster (e.g., a cluster containing silver) can contain less than the 14 atoms and have a normal face centered cubic crystal lattice.

Materials

The metal-containing material can be an ionic material or a non-ionic material. The metal-containing material can be, for example, an atom, a molecule, or a cluster.

In general, the metal-containing material is a metal or an alloy. Examples of metal elements that can be contained in metal-containing materials include Group I A metal elements, Group II A metal elements, Group III A metal elements, Group IV A metal elements, Group V A metal elements, Group VI A metal elements, Group VII A metal elements, Group VIII A metal elements, Group I B metal elements, Group II B metal elements, members of the lanthanide metal element series, and members of the actinide metal element series. In certain embodiments, metal-containing materials contain silver, gold, platinum, palladium, iridium, zinc, copper, tin, antimony, and/or bismuth. In some embodiments, a metal-containing material can include one or more transition metal elements (e.g., scandium, titanium, vanadium, chromium, manganese, iron, cobalt, nickel, copper and/or zinc). As an example, a metal-containing material can contain silver and platinum.

Examples of silver-containing materials include colloidal silver, silver nitrate and silver sulfadiazine, silver carbonate, silver acetate, silver lactate, silver citrate, silver oxide, silver hydroxide, silver succinate, silver chlorate, silver stearate, silver sorbate, silver oleate, silver glutonate, silver adipate, silver myristate, and alkali silver thiosulphate (e.g., sodium silver thiosulphate, potassium silver thiosulphate).

In addition to one or more metal elements, a metal-containing material can contain, for example, oxygen, nitrogen, carbon, boron, sulfur, phosphorus, silicon, a halogen (e.g., fluorine, chlorine, bromine, iodine) and/or hydrogen. Examples of such metal-containing materials include metal oxides, metal hydroxides, metal nitrides, metal carbides, metal phosphides, metal silicates, metal borides, metal sulfides, metal halides (e.g., metal fluorides, metal chlorides, metal bromides, metal iodides), metal myristates, metal sorbates, metal stearates, metal oleates, metal glutonates, metal adipates, metal silicates, metal phosphides, metal hydrides, metal nitrates, metal carbonates, metal sulfadiazines, metal hydrides, metal acetates, metal lactates, metal citrates, alkali metal thiosulphates (e.g., sodium metal thiosulphate, potassium metal thiosulphate). In certain embodiments, a metal-containing material contains at least about one atomic percent (e.g., at least about three atomic percent, at least about five atomic percent, at least about 10 atomic percent, at least about 20 atomic percent, at least about 30 atomic percent, at least about 40 atomic percent, at least about 50 atomic percent) and/or at most about 90 atomic percent (e.g., at most about 80 atomic percent, at most about 70 atomic percent, at most about 60 atomic percent, at most about 50 atomic percent, at most about 40 atomic percent, at most about 30 atomic percent, at most about 20 atomic percent, at most about 15 atomic percent, at most about 12 atomic percent, at most about 10 atomic percent) of non-metallic elements. For example, in some embodiments, a silver-containing material can contain oxygen in an amount from about five atomic percent to about 20 atomic percent (e.g., from about five atomic percent to about 15 atomic percent, from about eight atomic percent to about 12 atomic percent).

In certain embodiments, the metal-containing materials are an antimicrobial material, an anti-biofilm, an antibacterial material, an anti-inflammatory material, an antifungal material, an antiviral material, an anti-autoimmune material, an anti-cancer material, a pro-apoptosis material, an anti-proliferative material, an MMP modulating material, an atomically disordered crystalline material, and/or a nanocrystalline material.

As used herein, an antimicrobial material herein refers to a material that has sufficient antimicrobial activity to have a beneficial therapeutic effect. In certain embodiments, an antimicrobial material has a corrected zone of inhibition ("CZOI") of at least about two millimeters (e.g., at least about three millimeters, at least about four millimeters, at lest about five millimeters, at least about six millimeters, at least about seven millimeters, at least about eight millimeters, at least about nine millimeters, at least about 10 millimeters). The CZOI of a material is determined as follows. The material is formed as a coating on a dressing (see discussion below). Basal medium Eagle (BME) with Earle's salts and L-glutamine is modified with calf/serum (10%) and 1.5% agar prior to being dispensed (15 ml) into Petri dishes. The agar containing Petri dishes are allowed to surface dry prior to being inoculated with a lawn of *Staphylococcus aureus* ATCC #25923. The inoculant is prepared from Bactrol Discs (Difco, M.) which are reconstituted as per the manufacturer's directions. Immediately after inoculation, the coatings to be tested are placed on the surface of the agar. The dishes are incubated for 24 hours at 37° C. After this incubation period, the zone of inhibition ("ZOI") is measured and the CZOI is calculated as the ZOI minus the diameter of the test material in contact with the agar. It is to be noted that, while this test for antimicrobial properties is performed on materials that are in the form of a coating on a substrate (e.g., in the form of a dressing), antimicrobial materials are not limited to materials that are coated on a substrate. Rather, a material in any form may be antimicrobial, but it is in the form of a coating on a substrate (e.g., in the form of a dressing) when its antimicrobial properties are tested according to the procedure described herein.

As referred to herein, an atomically disordered, crystalline material (e.g., an atomically disordered, nanocrystalline material) means a material that has more long range ordered, crystalline structure (a lesser degree of defects) than the material has in a fully amorphous state, but that also has less long range, ordered crystalline structure (a higher degree of defects) than the material has in a bulk crystalline state, such as in the form of a cast, wrought or plated material. Examples of defects include point defects, vacancies, line defects, grain boundaries, subgrain boundaries and amorphous regions. Point defects are defects on a size scale of no more than about four atomic spacings. A vacancy is the omission of an atom from its regular atomic site in the crystal lattice. Line defects are defective regions (e.g., edge dislocations, screw dislocations) that result in lattice distortions along a line (which may or may not be a straight line), and generally have a longer scale than point defects. In an edge dislocation, a lattice displacement is produced by a plane of atoms that forms a terminus of the lattice. In a screw dislocation, part of the lattice is displaced with respect to an adjacent part of the lattice. Grain boundaries separate regions having different crystallographic orientation or misorientation (e.g., high angle grain boundaries, low angle grain boundaries, including tilt boundaries and twist boundaries). Subgrain boundaries refer to low angle grain boundaries. An amorphous region is a region that does not exhibit long range, ordered crystalline structure. In certain embodiments, an atomically disordered, crystalline material (e.g., an atomically disordered, nanocrystalline material) has a degree of atomic disorder that is about the same as the degree of atomic disorder of the nanocrystalline silver coating of a member of the Acticoat® family of dressings (Smith & Nephew, Hull, UK) (e.g., an Acticoat® dressing, an Acticoat7® dressing, an Acticoat® moisture coating dressing, an Acticoat® absorbent dressings). In some embodiments, an atomically disordered, crystalline material (e.g., an atomically disordered, nanocrystalline material) has a degree of atomic disorder that is about the same as the degree of atomic disorder of the nanocrystalline silver coatings having a CZOI of at least five millimeters that are disclosed in the examples of Burrell et al., U.S. Pat. No. 5,958,440. In certain embodiments, an atomically disordered, crystalline material (e.g., an atomically disordered, nanocrystalline material), when contacted with an alcohol or water-based electrolyte, is released into the alcohol or water-based electrolyte (e.g., as ions, atoms, molecules and/or clusters) over a time scale of at least about one hour (e.g., at least about two hours, at least about 10 hours, at least about a day). Examples of alcohols and/or water-based electrolytes include body fluids (e.g., blood, urine, saliva) and body tissue (e.g., skin, muscle, bone).

As referred to herein, a nanocrystalline material is a single-phase polycrystal or a multi-phase polycrystal having a maximum dimension of about 100 nanometers or less (e.g., about 90 nanometers or less, about 80 nanometers or less, about 70 nanometers or less, about 60 nanometers or less, about 50 nanometers or less, about 40 nanometers or less, about 30 nanometers or less, about 25 nanometers or less) in at least one dimension.

Examples of antimicrobial metal-containing materials (which may or may not also be an atomically disordered crystalline material or a nanocrystalline material) include antimicrobial silver-containing materials (e.g., antimicrobial silver, antimicrobial silver alloys, antimicrobial silver oxides, antimicrobial silver carbides, antimicrobial silver nitrides, antimicrobial silver borides, antimicrobial silver sulfides, antimicrobial silver myristates, antimicrobial silver stearates, antimicrobial silver oleates, antimicrobial silver glutonates, antimicrobial silver adipates, antimicrobial silver silicates, antimicrobial silver phosphides, antimicrobial silver halides, antimicrobial silver hydrides, antimicrobial silver nitrates, antimicrobial silver carbonates, antimicrobial silver sulfadiazines, antimicrobial silver acetates, antimicrobial silver lactates, antimicrobial silver citrates, antimicrobial alkali silver thiosulphates (e.g., antimicrobial sodium silver thiosulphate, antimicrobial potassium silver thiosulphate)), antimicrobial gold-containing materials (e.g., antimicrobial gold, antimicrobial gold alloys, antimicrobial gold oxides, antimicrobial gold carbides, antimicrobial gold nitrides, antimicrobial gold borides, antimicrobial gold sulfides, antimicrobial gold myristates, antimicrobial gold stearates, antimicrobial gold oleates, antimicrobial gold glutonates, antimicrobial gold glutonates, antimicrobial gold adipates, antimicrobial gold silicates, antimicrobial gold phosphides, antimicrobial gold halides, antimicrobial gold hydrides, antimicrobial gold nitrates, antimicrobial gold carbonates, antimicrobial gold sulfadiazines, antimicrobial gold acetates, antimicrobial gold lactates, antimicrobial gold citrates, antimicrobial alkali gold thiosulphates (e.g., antimicrobial sodium gold thiosulphate, antimicrobial potassium gold thiosulphate)), antimicrobial platinum-containing materials (e.g., antimicrobial platinum, antimicrobial platinum alloys, antimicrobial platinum oxides, antimicrobial platinum carbides, antimicrobial platinum nitrides, antimicrobial platinum borides, antimicrobial platinum sulfides, antimicrobial platinum myristates, antimicrobial platinum stearates, antimicrobial platinum oleates, antimicrobial platinum glutonates, antimicrobial platinum glutonates, antimicrobial platinum adipates, antimicrobial platinum silicates, antimicrobial platinum phosphides, antimicrobial platinum halides, antimicrobial platinum hydrides, antimicrobial platinum nitrates, antimicrobial platinum carbonates, antimicrobial platinum sulfadiazines, antimicrobial platinum acetates, antimicrobial platinum lactates, antimicrobial platinum citrates, antimicrobial alkali platinum thiosulphates (e.g., antimicrobial sodium platinum thiosulphate, antimicrobial potassium platinum thiosulphate)), antimicrobial palladium-containing materials (e.g., antimicrobial palladium, antimicrobial palladium alloys, antimicrobial palladium oxides, antimicrobial palladium carbides, antimicrobial palladium nitrides, antimicrobial palladium borides, antimicrobial palladium sulfides, antimicrobial palladium myristates, antimicrobial palladium stearates, antimicrobial palladium oleates, antimicrobial palladium glutonates, antimicrobial palladium glutonates, antimicrobial palladium adipates, antimicrobial palladium silicates, antimicrobial palladium phosphides, antimicrobial palladium halides, antimicrobial palladium hydrides, antimicrobial palladium nitrates, antimicrobial palladium carbonates, antimicrobial palladium sulfadiazines, antimicrobial palladium acetates, antimicrobial palladium lactates, antimicrobial palladium citrates, antimicrobial alkali palladium thiosulphates (e.g., antimicrobial sodium palladium thiosulphate, antimicrobial potassium palladium thiosulphate)), antimicrobial iridium-containing materials (e.g., antimicrobial iridium, antimicrobial iridium alloys, antimicrobial iridium oxides, antimicrobial iridium carbides, antimicrobial iridium nitrides, antimicrobial iridium borides, antimicrobial iridium sulfides, antimicrobial iridium myristates, antimicrobial iridium stearates, antimicrobial iridium oleates, antimicrobial iridium glutonates, antimicrobial iridium glutonates, antimicrobial iridium adipates, antimicrobial iridium silicates, antimicrobial iridium phosphides, antimicrobial iridium halides, antimicrobial iridium hydrides, antimicrobial iridium nitrates, antimicrobial iridium carbonates, antimicrobial iridium sulfides, antimicrobial iridium sulfadiazines; antimicrobial iridium acetates, antimicrobial iridium lactates, antimicrobial iridium citrates, antimicrobial alkali iridium thiosulphates (e.g., antimicrobial sodium iridium thiosulphate, antimicrobial potassium iridium thiosulphate)), antimicrobial zinc-containing materials (e.g., antimicrobial zinc, antimicrobial zinc alloys, antimicrobial zinc oxides, antimicrobial zinc carbides, antimicrobial zinc nitrides, antimicrobial zinc borides, antimicrobial zinc sulfides, antimicrobial zinc myristates, antimicrobial zinc stearates, antimicrobial zinc oleates, antimicrobial zinc glutonates, antimicrobial zinc glutonates, antimicrobial zinc adipates, antimicrobial zinc silicates, antimicrobial zinc phosphides, antimicrobial zinc halides, antimicrobial zinc hydrides, antimicrobial zinc nitrates, antimicrobial zinc carbonates, antimicrobial zinc sulfides, antimicrobial zinc sulfadiazines, antimicrobial zinc acetates, antimicrobial zinc lactates, antimicrobial zinc citrates, antimicrobial alkali zinc thiosulphates (e.g., antimicrobial sodium zinc thiosulphate, antimicrobial potassium zinc thiosulphate)), antimicrobial copper-containing materials (e.g., antimicrobial copper, antimicrobial copper alloys, antimicrobial copper oxides, antimicrobial copper carbides, antimicrobial copper nitrides, antimicrobial copper borides, antimicrobial copper sulfides, antimicrobial copper myristates, antimicrobial copper stearates, antimicrobial copper oleates, antimicrobial copper glutonates, antimicrobial copper glutonates, antimicrobial copper adipates, antimicrobial copper silicates, antimicrobial copper phosphides, antimicrobial copper halides, antimicrobial copper hydrides, antimicrobial copper nitrates, antimicrobial copper carbonates, antimicrobial copper sulfides, antimicrobial copper sulfadiazines, antimicrobial copper acetates, antimicrobial copper lactates, antimicrobial copper citrates, antimicrobial alkali copper thiosulphates (e.g., antimicrobial sodium copper thiosulphate, antimicrobial potassium copper thiosulphate)), antimicrobial tin-containing materials (e.g., antimicrobial tin, antimicrobial tin alloys, antimicrobial tin oxides, antimicrobial tin carbides, antimicrobial tin nitrides, antimicrobial tin borides, antimicrobial tin sulfides, antimicrobial tin myristates, antimicrobial tin stearates, antimicrobial tin oleates, antimicrobial tin glutonates, antimicrobial tin glutonates, antimicrobial tin adipates, antimicrobial tin silicates, antimicrobial tin phosphides, antimicrobial tin halides, antimicrobial tin hydrides, antimicrobial tin nitrates, antimicrobial tin carbonates, antimicrobial tin sulfides, antimicrobial tin sulfadiazines, antimicrobial tin acetates, antimicrobial tin lactates, antimicrobial tin citrates, antimicrobial alkali tin thiosulphates (e.g., antimicrobial sodium tin thiosulphate, antimicrobial potassium tin thiosulphate)), antimicrobial antimony-containing materials (e.g., antimicrobial antimony, antimicrobial antimony alloys, antimicrobial antimony oxides, antimicrobial antimony carbides, antimicrobial antimony nitrides, antimicrobial antimony borides, antimicrobial antimony sulfides, antimicrobial antimony myristates, antimicrobial antimony stearates, antimicrobial antimony oleates, antimicrobial antimony glutonates, antimicrobial antimony glutonates, antimicrobial antimony adipates, antimicrobial antimony silicates, antimicrobial antimony phosphides, antimicrobial antimony halides, antimicrobial antimony hydrides, antimicrobial antimony nitrates, antimicrobial antimony carbonates, antimicrobial antimony sulfides, antimicrobial antimony sulfadiazines, antimicrobial antimony acetates, antimicrobial antimony lactates, antimicrobial antimony citrates, antimicrobial alkali antimony thiosulphates (e.g., antimicrobial sodium antimony thiosulphate, antimicrobial potassium antimony thiosulphate)), antimicrobial bismuth containing materials (e.g., antimicrobial bismuth, antimicrobial bismuth alloys, antimicrobial bismuth oxides, antimicrobial bismuth carbides, antimicrobial bismuth nitrides, antimicrobial bismuth borides, antimicrobial bismuth sulfides, antimicrobial bismuth myristates, antimicrobial bismuth stearates, antimicrobial bismuth oleates, antimicrobial bismuth glutonates, antimicrobial bismuth glutonates, antimicrobial bismuth adipates, antimicrobial bismuth silicates, antimicrobial bismuth phosphides, antimicrobial bismuth halides, antimicrobial bismuth hydrides, antimicrobial bismuth nitrates, antimicrobial bismuth carbonates, antimicrobial bismuth sulfides, antimicrobial bismuth sulfadiazines, antimicrobial bismuth acetates, antimicrobial bismuth lactates, antimicrobial bismuth citrates, antimicrobial alkali bismuth thiosulphates (e.g., antimicrobial sodium bismuth thiosulphate, antimicrobial potassium bismuth thiosulphate)).

While the preceding paragraph lists certain metal-containing materials that are anti-microbial, similar metal-containing materials (oxides, carbides, nitrides, borides, sulfides, myristates, stearates, oleates, glutonates, adipates, silicates, phosphides, halides, hydrides, nitrates, hydroxides, carbonates, sulfides, sulfadiazines, acetates, lactates, citrates and/or alkali metal thiosulphates of silver, gold, palladium, platinum, tin, iridium, antimony, bismuth, copper, zinc) can be anti-biofilm materials, antibacterial materials, anti-inflammatory materials, antifungal materials, antiviral materials, anti-autoimmune materials, anti-cancer materials, pro-apoptosis materials, anti-proliferatives, and/or MMP modulating materials.

Examples of nanocrystalline metal-containing materials (which may or may not also be an antimicrobial material or an atomically disordered crystalline material) include nanocrystalline silver-containing materials (e.g., nanocrystalline silver, nanocrystalline silver alloys, nanocrystalline silver oxides, nanocrystalline silver carbides, nanocrystalline silver nitrides, nanocrystalline silver borides, nanocrystalline silver sulfides, nanocrystalline silver halides, nanocrystalline silver myristates, nanocrystalline silver stearates, nanocrystalline silver oleates, nanocrystalline silver glutonates, nanocrystalline silver glutonates, nanocrystalline silver adipates, nanocrystalline silver silicates, nanocrystalline silver phosphides, nanocrystalline silver hydrides, nanocrystalline silver nitrates, nanocrystalline silver carbonates, nanocrystalline silver sulfides, nanocrystalline silver sulfadiazines, nanocrystalline silver acetates, nanocrystalline silver lactates, nanocrystalline silver citrates, nanocrystalline alkali silver thiosulphates (e.g., nanocrystalline sodium silver thiosulphate, nanocrystalline potassium silver thiosulphate)), nanocrystalline gold-containing materials (e.g., nanocrystalline gold, nanocrystalline gold alloys, nanocrystalline gold oxides, nanocrystalline gold carbides, nanocrystalline gold nitrides, nanocrystalline gold borides, nanocrystalline gold sulfides, nanocrystalline gold halides, nanocrystalline gold hydrides, nanocrystalline gold nitrates, nanocrystalline gold myristates, nanocrystalline gold stearates, nanocrystalline gold oleates, nanocrystalline gold glutonates, nanocrystalline gold glutonates, nanocrystalline gold adipates, nanocrystalline gold silicates, nanocrystalline gold phosphides, nanocrystalline gold carbonates, nanocrystalline gold sulfides, nanocrystalline gold sulfadiazines, nanocrystalline gold acetates, nanocrystalline gold lactates, nanocrystalline gold citrates, nanocrystalline alkali gold thiosulphates (e.g., nanocrystalline sodium gold thiosulphate, nanocrystalline potassium gold thiosulphate)), nanocrystalline platinum-containing materials (e.g., nanocrystalline platinum, nanocrystalline platinum alloys, nanocrystalline platinum oxides, nanocrystalline platinum carbides, nanocrystalline platinum nitrides, nanocrystalline platinum borides, nanocrystalline platinum sulfides, nanocrystalline platinum myristates, nanocrystalline platinum stearates, nanocrystalline platinum oleates, nanocrystalline platinum glutonates, nanocrystalline platinum glutonates, nanocrystalline platinum adipates, nanocrystalline platinum silicates, nanocrystalline platinum phosphides, nanocrystalline platinum halides, nanocrystalline platinum hydrides, nanocrystalline platinum nitrates, nanocrystalline platinum carbonates, nanocrystalline platinum sulfides, nanocrystalline platinum sulfadiazines, nanocrystalline platinum acetates, nanocrystalline platinum lactates, nanocrystalline platinum citrates, nanocrystalline alkali platinum thiosulphates (e.g., nanocrystalline sodium platinum thiosulphate, nanocrystalline potassium platinum thiosulphate)), nanocrystalline palladium-containing materials (e.g., nanocrystalline palladium, nanocrystalline palladium alloys, nanocrystalline palladium oxides, nanocrystalline palladium carbides, nanocrystalline palladium nitrides, nanocrystalline palladium borides, nanocrystalline palladium sulfides, nanocrystalline palladium myristates, nanocrystalline palladium stearates, nanocrystalline palladium oleates, nanocrystalline palladium glutonates, nanocrystalline palladium glutonates, nanocrystalline palladium adipates, nanocrystalline palladium silicates, nanocrystalline palladium phosphides, nanocrystalline palladium halides, nanocrystalline palladium hydrides, nanocrystalline palladium nitrates, nanocrystalline palladium carbonates, nanocrystalline palladium sulfides, nanocrystalline palladium sulfadiazines, nanocrystalline palladium acetates, nanocrystalline palladium lactates, nanocrystalline palladium citrates, nanocrystalline alkali palladium thiosulphates (e.g., nanocrystalline sodium palladium thiosulphate, nanocrystalline potassium palladium thiosulphate)), nanocrystalline iridium-containing materials (e.g., nanocrystalline iridium, nanocrystalline iridium alloys, nanocrystalline iridium oxides, nanocrystalline iridium carbides, nanocrystalline iridium nitrides, nanocrystalline iridium borides, nanocrystalline iridium sulfides, nanocrystalline iridium myristates, nanocrystalline iridium stearates, nanocrystalline iridium oleates, nanocrystalline iridium glutonates, nanocrystalline iridium glutonates, nanocrystalline iridium adipates, nanocrystalline iridium silicates, nanocrystalline iridium phosphides, nanocrystalline iridium halides, nanocrystalline iridium hydrides, nanocrystalline iridium nitrates, nanocrystalline iridium carbonates, nanocrystalline iridium sulfides, nanocrystalline iridium sulfadiazines, nanocrystalline iridium acetates, nanocrystalline iridium lactates, nanocrystalline iridium citrates, nanocrystalline alkali iridium thiosulphates (e.g., nanocrystalline sodium iridium thiosulphate, nanocrystalline potassium iridium thiosulphate)), nanocrystalline zinc-containing materials (e.g., nanocrystalline zinc, nanocrystalline zinc alloys, nanocrystalline zinc oxides, nanocrystalline zinc carbides, nanocrystalline zinc nitrides, nanocrystalline zinc borides, nanocrystalline zinc sulfides, nanocrystalline zinc myristates, nanocrystalline zinc stearates, nanocrystalline zinc oleates, nanocrystalline zinc glutonates, nanocrystalline zinc glutonates, nanocrystalline zinc adipates, nanocrystalline zinc silicates, nanocrystalline zinc phosphides, nanocrystalline zinc halides, nanocrystalline zinc hydrides, nanocrystalline zinc nitrates, nanocrystalline zinc carbonates, nanocrystalline zinc sulfides, nanocrystalline zinc sulfadiazines, nanocrystalline zinc acetates, nanocrystalline zinc lactates, nanocrystalline zinc citrates, nanocrystalline alkali zinc thiosulphates (e.g., nanocrystalline sodium zinc thiosulphate, nanocrystalline potassium zinc thiosulphate)), nanocrystalline copper-containing materials (e.g., nanocrystalline copper, nanocrystalline copper alloys, nanocrystalline copper oxides, nanocrystalline copper carbides, nanocrystalline copper nitrides, nanocrystalline copper borides, nanocrystalline copper sulfides, nanocrystalline copper myristates, nanocrystalline copper stearates, nanocrystalline copper oleates, nanocrystalline copper glutonates, nanocrystalline copper glutonates, nanocrystalline copper adipates, nanocrystalline copper silicates, nanocrystalline copper phosphides, nanocrystalline copper halides, nanocrystalline copper hydrides, nanocrystalline copper nitrates, nanocrystalline copper carbonates, nanocrystalline copper sulfadiazines, nanocrystalline copper acetates, nanocrystalline copper lactates, nanocrystalline copper citrates, nanocrystalline alkali copper thiosulphates (e.g., nanocrystalline sodium copper thiosulphate, nanocrystalline potassium copper thiosulphate)), nanocrystalline tin-containing materials (e.g., nanocrystalline tin, nanocrystalline tin alloys, nanocrystalline tin oxides, nanocrystalline tin carbides, nanocrystalline tin nitrides, nanocrystalline tin borides, nanocrystalline tin sulfides, nanocrystalline tin myristates, nanocrystalline tin stearates, nanocrystalline tin oleates, nanocrystalline tin glutonates, nanocrystalline tin glutonates, nanocrystalline tin adipates, nanocrystalline tin silicates, nanocrystalline tin phosphides, nanocrystalline tin halides, nanocrystalline tin hydrides, nanocrystalline tin nitrates, nanocrystalline tin carbonates, nanocrystalline tin sulfides, nanocrystalline tin sulfadiazines, nanocrystalline tin acetates, nanocrystalline tin lactates, nanocrystalline tin citrates, nanocrystalline alkali tin thiosulphates (e.g., nanocrystalline sodium tin thiosulphate, nanocrystalline potassium tin thiosulphate)), nanocrystalline antimony-containing materials (e.g., nanocrystalline antimony, nanocrystalline antimony alloys, nanocrystalline antimony oxides, nanocrystalline antimony carbides, nanocrystalline antimony nitrides, nanocrystalline antimony borides, nanocrystalline antimony sulfides, nanocrystalline antimony myristates, nanocrystalline antimony stearates, nanocrystalline antimony oleates, nanocrystalline antimony glutonates, nanocrystalline antimony glutonates, nanocrystalline antimony adipates, nanocrystalline antimony silicates, nanocrystalline antimony phosphides, nanocrystalline antimony halides, nanocrystalline antimony hydrides, nanocrystalline antimony nitrates, nanocrystalline antimony carbonates, nanocrystalline antimony sulfides, nanocrystalline antimony sulfadiazines, nanocrystalline antimony acetates, nanocrystalline antimony lactates, nanocrystalline antimony citrates, nanocrystalline alkali antimony thiosulphates (e.g., nanocrystalline sodium antimony thiosulphate, nanocrystalline potassium antimony thiosulphate)), nanocrystalline bismuth containing materials (e.g., nanocrystalline bismuth, nanocrystalline bismuth alloys, nanocrystalline bismuth oxides, nanocrystalline bismuth carbides, nanocrystalline bismuth nitrides, nanocrystalline bismuth borides, nanocrystalline bismuth sulfides, nanocrystalline bismuth myristates, nanocrystalline bismuth stearates, nanocrystalline bismuth oleates, nanocrystalline bismuth glutonates, nanocrystalline bismuth glutonates, nanocrystalline bismuth adipates, nanocrystalline bismuth silicates, nanocrystalline bismuth phosphides, nanocrystalline bismuth halides, nanocrystalline bismuth hydrides, nanocrystalline bismuth nitrates, nanocrystalline bismuth carbonates, nanocrystalline bismuth sulfides, nanocrystalline anti bismuth sulfadiazines, nanocrystalline bismuth acetates, nanocrystalline bismuth lactates, nanocrystalline bismuth citrates, nanocrystalline alkali bismuth thiosulphates (e.g., nanocrystalline sodium bismuth thiosulphate, nanocrystalline potassium bismuth thiosulphate)).

Examples of atomically disordered, crystalline metal-containing material (which may or may not also be an antimicrobial material or a nanocrystalline material) include atomically disordered, crystalline silver-containing materials (e.g., atomically disordered, crystalline silver; atomically disordered, crystalline silver alloys; atomically disordered, crystalline silver oxides; atomically disordered, crystalline silver carbides; atomically disordered, crystalline silver nitrides; atomically disordered, crystalline silver borides; atomically disordered, crystalline silver sulfides; atomically disordered, crystalline silver myristates; atomically disordered, crystalline silver stearates; atomically disordered, crystalline silver oleates; atomically disordered, crystalline silver glutonates; atomically disordered, crystalline silver glutonates; atomically disordered, crystalline silver adipates; atomically disordered, crystalline silver silicates; atomically disordered, crystalline silver phosphides; atomically disordered, crystalline silver halides; atomically disordered, crystalline silver hydrides, atomically disordered, crystalline silver nitrates; atomically disordered, crystalline silver carbonates; atomically disordered, crystalline silver sulfides; atomically disordered, crystalline silver sulfadiazines; atomically disordered, crystalline silver acetates; atomically disordered, crystalline silver lactates; atomically disordered, crystalline silver citrates; atomically disordered, crystalline alkali silver thiosulphates (e.g., atomically disordered, crystalline sodium silver thiosulphate, atomically disordered, crystalline potassium silver thiosulphate)), atomically disordered, crystalline gold-containing materials (atomically disordered, crystalline gold; atomically disordered, crystalline gold alloys; atomically disordered, crystalline gold oxides; atomically disordered, crystalline gold carbides; atomically disordered, crystalline gold nitrides; atomically disordered, crystalline gold borides; atomically disordered, crystalline gold sulfides; atomically disordered, crystalline gold myristates; atomically disordered, crystalline gold stearates; atomically disordered, crystalline gold oleates; atomically disordered, crystalline gold glutonates; atomically disordered, crystalline gold glutonates; atomically disordered, crystalline gold adipates; atomically disordered, crystalline gold silicates; atomically disordered, crystalline gold phosphides; atomically disordered, crystalline gold halides; atomically disordered, crystalline gold hydrides, atomically disordered, crystalline gold nitrates; atomically disordered, crystalline gold carbonates; atomically disordered, crystalline gold sulfides; atomically disordered, crystalline gold sulfadiazines; atomically disordered, crystalline gold acetates; atomically disordered, crystalline gold lactates; atomically disordered, crystalline gold citrates; atomically disordered, crystalline alkali gold thiosulphates (e.g., atomically disordered, crystalline sodium gold thiosulphate, atomically disordered, crystalline potassium gold thiosulphate)), atomically disordered, crystalline platinum-containing materials (e.g., atomically disordered, crystalline platinum; atomically disordered, crystalline platinum alloys; atomically disordered, crystalline platinum oxides; atomically disordered, crystalline platinum carbides; atomically disordered, crystalline platinum nitrides; atomically disordered, crystalline platinum borides; atomically disordered, crystalline platinum sulfides; atomically disordered, crystalline platinum myristates; atomically disordered, crystalline platinum stearates; atomically disordered, crystalline platinum oleates; atomically disordered, crystalline platinum glutonates; atomically disordered, crystalline platinum glutonates; atomically disordered, crystalline platinum adipates; atomically disordered, crystalline platinum silicates; atomically disordered, crystalline platinum phosphides; atomically disordered, crystalline platinum halides; atomically disordered, crystalline platinum hydrides, atomically disordered, crystalline platinum nitrates; atomically disordered, crystalline platinum carbonates; atomically disordered, crystalline platinum sulfides; atomically disordered, crystalline platinum sulfadiazines; atomically disordered, crystalline platinum acetates; atomically disordered, crystalline platinum lactates; atomically disordered, crystalline platinum citrates; atomically disordered, crystalline alkali platinum thiosulphates (e.g., atomically disordered, crystalline sodium platinum thiosulphate, atomically disordered, crystalline potassium platinum thiosulphate), atomically disordered, crystalline palladium-containing materials (e.g., atomically disordered, crystalline palladium; atomically disordered, crystalline palladium alloys; atomically disordered, crystalline palladium oxides; atomically disordered, crystalline palladium carbides; atomically disordered, crystalline palladium nitrides; atomically disordered, crystalline palladium borides; atomically disordered, crystalline palladium sulfides; atomically disordered, crystalline palladium myristates; atomically disordered, crystalline palladium stearates; atomically disordered, crystalline palladium oleates, atomically disordered, crystalline palladium glutonates; atomically disordered, crystalline palladium glutonates; atomically disordered, crystalline palladium adipates; atomically disordered, crystalline palladium silicates; atomically disordered, crystalline palladium phosphides; atomically disordered, crystalline palladium halides; atomically disordered, crystalline palladium hydrides, atomically disordered, crystalline palladium nitrates; atomically disordered, crystalline palladium carbonates; atomically disordered, crystalline palladium sulfides; atomically disordered, crystalline palladium sulfadiazines; atomically disordered, crystalline palladium acetates; atomically disordered, crystalline palladium lactates; atomically disordered, crystalline palladium citrates; atomically disordered, crystalline alkali palladium thiosulphates (e.g., atomically disordered, crystalline sodium palladium thiosulphate, atomically disordered, crystalline potassium palladium thiosulphate)), atomically disordered, crystalline iridium-containing materials (e.g., atomically disordered, crystalline iridium; atomically disordered, crystalline iridium alloys; atomically disordered, crystalline iridium oxides; atomically disordered, crystalline iridium carbides; atomically disordered, crystalline iridium nitrides; atomically disordered, crystalline iridium borides; atomically disordered, crystalline iridium sulfides; atomically disordered, crystalline iridium myristates; atomically disordered, crystalline iridium stearates; atomically disordered, crystalline iridium oleates; atomically disordered, crystalline iridium glutonates; atomically disordered, crystalline iridium glutonates; atomically disordered, crystalline iridium adipates; atomically disordered, crystalline iridium silicates; atomically disordered, crystalline iridium phosphides; atomically disordered, crystalline iridium halides; atomically disordered, crystalline iridium hydrides, atomically disordered, crystalline iridium nitrates; atomically disordered, crystalline iridium carbonates; atomically disordered, crystalline iridium sulfides; atomically disordered, crystalline iridium sulfadiazines; atomically disordered, crystalline iridium acetates; atomically disordered, crystalline iridium lactates; atomically disordered, crystalline iridium citrates; atomically disordered, crystalline alkali iridium thiosulphates (e.g., atomically disordered, crystalline sodium iridium thiosulphate, atomically disordered, crystalline potassium iridium thiosulphate)), atomically disordered, crystalline zinc-containing materials (e.g., atomically disordered, crystalline zinc; atomically disordered, crystalline zinc alloys; atomically disordered, crystalline zinc oxides; atomically disordered, crystalline zinc carbides; atomically disordered, crystalline zinc nitrides; atomically disordered, crystalline zinc borides; atomically disordered, crystalline zinc sulfides; atomically disordered, crystalline zinc myristates; atomically disordered, crystalline zinc stearates; atomically disordered, crystalline zinc oleates; atomically disordered, crystalline zinc glutonates; atomically disordered, crystalline zinc glutonates; atomically disordered, crystalline zinc adipates; atomically disordered, crystalline zinc silicates; atomically disordered, crystalline zinc phosphides; atomically disordered, crystalline zinc halides; atomically disordered, crystalline zinc hydrides, atomically disordered, crystalline zinc nitrates; atomically disordered, crystalline zinc carbonates; atomically disordered, crystalline zinc sulfides; atomically disordered, crystalline zinc sulfadiazines; atomically disordered, crystalline zinc acetates; atomically disordered, crystalline zinc lactates; atomically disordered, crystalline zinc citrates; atomically disordered, crystalline alkali zinc thiosulphates (e.g., atomically disordered, crystalline sodium zinc thiosulphate, atomically disordered, crystalline potassium zinc thiosulphate)), atomically disordered, crystalline copper-containing materials (e.g., atomically disordered, crystalline copper; atomically disordered, crystalline copper alloys; atomically disordered, crystalline copper oxides; atomically disordered, crystalline copper carbides; atomically disordered, crystalline copper nitrides; atomically disordered, crystalline copper borides; atomically disordered, crystalline copper sulfides; atomically disordered, crystalline copper myristates; atomically disordered, crystalline copper stearates; atomically disordered, crystalline copper oleates; atomically disordered, crystalline copper glutonates; atomically disordered, crystalline copper glutonates; atomically disordered, crystalline copper adipates; atomically disordered, crystalline copper silicates; atomically disordered, crystalline copper phosphides; atomically disordered, crystalline copper halides; atomically disordered, crystalline copper hydrides, atomically disordered, crystalline copper nitrates; atomically disordered, crystalline copper carbonates; atomically disordered, crystalline copper sulfides; atomically disordered, crystalline copper sulfadiazines; atomically disordered, crystalline copper acetates; atomically disordered, crystalline copper lactates; atomically disordered, crystalline copper citrates; atomically disordered, crystalline alkali copper thiosulphates (e.g., atomically disordered, crystalline sodium copper thiosulphate, atomically disordered, crystalline potassium copper thiosulphate)), atomically disordered, crystalline tin-containing materials (e.g., atomically disordered, crystalline tin; atomically disordered, crystalline tin alloys; atomically disordered, crystalline tin oxides; atomically disordered, crystalline tin carbides; atomically disordered, crystalline tin nitrides; atomically disordered, crystalline tin borides; atomically disordered, crystalline tin sulfides; atomically disordered, crystalline tin myristates; atomically disordered, crystalline tin stearates; atomically disordered, crystalline tin oleates; atomically disordered, crystalline tin glutonates; atomically disordered, crystalline tin glutonates; atomically disordered, crystalline tin adipates; atomically disordered, crystalline tin silicates; atomically disordered, crystalline tin phosphides; atomically disordered, crystalline tin halides; atomically disordered, crystalline tin hydrides, atomically disordered, crystalline tin nitrates; atomically disordered, crystalline tin carbonates; atomically disordered, crystalline tin sulfides; atomically disordered, crystalline tin sulfadiazines; atomically disordered, crystalline tin acetates; atomically disordered, crystalline tin lactates; atomically disordered, crystalline tin citrates; atomically disordered, crystalline alkali tin thiosulphates (e.g., atomically disordered, crystalline sodium tin thiosulphate, atomically disordered, crystalline potassium tin thiosulphate)), atomically disordered, crystalline antimony-containing materials (e.g., atomically disordered, crystalline antimony; atomically disordered, crystalline antimony alloys; atomically disordered, crystalline antimony oxides; atomically disordered, crystalline antimony carbides; atomically disordered, crystalline antimony nitrides; atomically disordered, crystalline antimony borides; atomically disordered, crystalline antimony sulfides; atomically disordered, crystalline antimony myristates; atomically disordered, crystalline antimony stearates; atomically disordered, crystalline antimony oleates; atomically disordered, crystalline antimony glutonates; atomically disordered, crystalline antimony glutonates; atomically disordered, crystalline antimony adipates; atomically disordered, crystalline antimony silicates; atomically disordered, crystalline antimony phosphides; atomically disordered, crystalline antimony halides; atomically disordered, crystalline antimony hydrides, atomically disordered, crystalline antimony nitrates; atomically disordered, crystalline antimony carbonates; atomically disordered, crystalline antimony sulfides; atomically disordered, crystalline antimony sulfadiazines; atomically disordered, crystalline antimony acetates; atomically disordered, crystalline go antimony ld lactates; atomically disordered, crystalline antimony citrates; atomically disordered, crystalline alkali antimony thiosulphates (e.g., atomically disordered, crystalline sodium antimony thiosulphate, atomically disordered, crystalline potassium antimony thiosulphate)), atomically disordered, crystalline bismuth-containing materials (e.g., atomically disordered, crystalline bismuth; atomically disordered, crystalline bismuth alloys; atomically disordered, crystalline bismuth oxides; atomically disordered, crystalline bismuth carbides; atomically disordered, crystalline bismuth nitrides; atomically disordered, crystalline bismuth borides; atomically disordered, crystalline bismuth sulfides; atomically disordered, crystalline bismuth myristates; atomically disordered, crystalline bismuth stearates; atomically disordered, crystalline bismuth oleates; atomically disordered, crystalline bismuth glutonates; atomically disordered, crystalline bismuth glutonates; atomically disordered, crystalline bismuth adipates; atomically disordered, crystalline bismuth silicates; atomically disordered, crystalline bismuth phosphides; atomically disordered, crystalline bismuth halides; atomically disordered, crystalline bismuth hydrides, atomically disordered, crystalline bismuth nitrates; atomically disordered, crystalline bismuth carbonates; atomically disordered, crystalline bismuth sulfides; atomically disordered, crystalline bismuth sulfadiazines; atomically disordered, crystalline bismuth acetates; atomically disordered, crystalline bismuth lactates; atomically disordered, crystalline bismuth citrates; atomically disordered, crystalline alkali bismuth thiosulphates (e.g., atomically disordered, crystalline sodium bismuth thiosulphate, atomically disordered, crystalline potassium bismuth thiosulphate)).

Subjects

The metal-containing material can be used to treat, for example a human or an animal (e.g., a dog, a cat, a horse, a bird, a reptile, an amphibian, a fish, a turtle, a guinea pig, a hamster, a rodent, a cow, a pig, a goat, a primate, a monkey, a chicken, a turkey, a buffalo, an ostrich, a sheep, a llama).

Conditions and Condition Locations

The conditions that can be treated with the metal-containing material include, for example, bacterial conditions, microbial conditions, biofilm conditions, inflammatory conditions, fungal conditions, viral conditions, autoimmune conditions, idiopathic conditions, hyperproliferative conditions, noncancerous growths and/or cancerous conditions (e.g., tumorous conditions, hematologic malignancies). Such conditions can be associated with, for example, one or more prions, parasites, fungi, viruses and/or bacteria. In general, the location of the condition to be treated corresponds to the type of condition to be treated.

In some embodiments, the condition can be a skin condition or a integument condition (e.g., a bacterial skin condition, a microbial skin condition, a biofilm skin condition, an inflammatory skin condition, a hyperproliferative skin condition, a fungal skin condition, a viral skin condition, an autoimmune skin condition, an idiopathic skin condition, a hyperproliferative skin condition, a cancerous skin condition, a microbial integument condition, an inflammatory integument condition, a fungal integument condition, a viral integument condition, an autoimmune integument condition, an idiopathic integument condition, a hyperproliferative integument condition, a cancerous integument condition). Examples of skin conditions or integument conditions include burns, eczema (e.g., atopic eczema, acrodermatitis continua, contact allergic dermatitis, contact irritant dermatitis, dyshidrotic eczema, pompholyx, lichen simplex chronicus, nummular eczema, seborrheic dermatitis, stasis eczema), erythroderma, insect bites, mycosis fungoides, pyoderma gangrenosum, eythrema multiforme, rosacea, onychomycosis, acne (e.g., acne *vulgaris*, neonatal acne, infantile acne, pomade acne), psoriasis, Reiter's syndrome, pityriasis rubra pilaris, hyperpigmentation, vitiligo, scarring conditions (e.g., hypertropic scarring), keloids, lichen planus, age-related skin disorders (e.g., wrinkles, cellulite) and hyperproliferative skin disorders, such as, for example, hyperproliferative variants of the disorders of keratinization (e.g., actinic keratosis, senile keratosis). Generally, the treatment of skin or integument conditions involves contacting the metal-containing material with the area of the skin having the condition. As an example, a skin or integument condition can be treated by contacting the area of skin having the condition with a dressing having a coating of the metal-containing material. As another example, a skin or integument condition can be treated by contacting the area of skin having the condition with a solution containing the metal-containing material. As an additional example, a skin or integument condition can be treated by contacting the area of skin having the condition with a pharmaceutical carrier composition containing the metal-containing material. In the case of onychomycosis, the material may be applied to the nail in an appropriate form (see below) such that the material penetrates the hard nail to contact the affected area.

In certain embodiments, the condition can be a respiratory condition (e.g., a bacterial respiratory condition, a biofilm respiratory condition, a microbial respiratory condition, an inflammatory respiratory condition, a fungal respiratory condition, a viral respiratory condition, an autoimmune respiratory condition, an idiopathic respiratory condition, a hyperproliferative respiratory condition, a cancerous respiratory condition). Examples of respiratory conditions include asthma, emphysema, bronchitis, pulmonary edema, acute respiratory distress syndrome, bronchopulmonary dysplasia, fibrotic conditions (e.g., pulmonary fibrosis), pulmonary atelectasis, tuberculosis, pneumonia, sinusitis, allergic rhinitis, pharyngitis, mucositis, stomatitis, chronic obstructive pulmonary disease, bronchiectasis, lupus pneumonitis and cystic fibrosis. In general, the treatment of respiratory conditions involves contacting the metal-containing material with the area of the respiratory system having the condition. Areas of the respiratory system include, for example, the oral cavity, the nasal cavity, and the lungs. As an example, certain respiratory conditions can be treated by inhaling a free standing powder of the metal-containing material (e.g., with a dry powder inhaler). As another example, certain respiratory conditions can be treated by inhaling an aerosol containing the metal-containing material (e.g., with an inhaler).

In some embodiments, the condition can be a musculo-skeletal condition (e.g., a bacterial musculo-skeletal condition, a biofilm musculo-skeletal condition, a microbial musculo-skeletal condition, an inflammatory musculo-skeletal condition, a fungal musculo-skeletal condition, a viral musculo-skeletal condition, an autoimmune musculo-skeletal condition, an idiopathic musculo-skeletal condition, a hyperproliferative musculo-skeletal condition, a cancerous musculo-skeletal condition). A musculo-skeletal condition can be, for example, a degenerative musculo-skeletal condition (e.g., arthritis) or a traumatic musculo-skeletal condition (e.g., a torn or damaged muscle). Examples of musculo-skeletal conditions include tendonitis, osteomyelitis, fibromyalgia, bursitis and arthritis. Generally, the treatment of musculo-skeletal conditions involves contacting the metal-containing material material with the area of the musculo-skeletal system having the condition. Areas of the musculo-skeletal system include, for example, the joints, the muscles, and the tendons. As an example, certain musculo-skeletal conditions can be treated by injecting (e.g., via a small needle injector) a solution containing the metal-containing material into the subject. As another example, certain musculo-skeletal conditions can be treated by injecting (e.g., via a needleless injector) a free standing powder of the metal-containing material into the subject. As an additional example, certain musculo-skeletal conditions can be treated by using a pharmaceutical carrier composition of the metal-containing material, such as a penetrating pharmaceutical carrier composition of the metal-containing material (e.g., a composition containing DMSO).

In certain embodiments, the condition can be a circulatory condition (e.g., a bacterial circulatory condition, a biofilm circulatory condition, a microbial circulatory condition, an inflammatory circulatory condition, a fungal circulatory condition, a viral circulatory condition, an autoimmune circulatory condition, an idiopathic circulatory condition, a hyperproliferative circulatory condition, a cancerous circulatory condition). As referred to herein, circulatory conditions include lymphatic conditions. Examples of circulatory conditions include arteriosclerosis, lymphoma, septicemia, leukemia, ischemic vascular disease, lymphangitis and atherosclerosis. In general, the treatment of circulatory conditions involves contacting the metal-containing material with the area of the circulatory system having the condition. Areas of the circulatory system include, for example, the heart, the lymphatic system, blood, blood vessels (e.g., arteries, veins). As an example, certain circulatory conditions can be treated by injecting (e.g., via a small needle injector) a solution containing the metal-containing material into the subject. As another example, certain circulatory conditions can be treated by injecting (e.g., via a needleless injector) a free standing powder of the metal-containing material into the subject.

In some embodiments, the condition can be a mucosal or serosal condition (e.g., a bacterial mucosal or serosal condition, a biofilm mucosal or serosal condition, a microbial mucosal or serosal condition, an inflammatory mucosal or serosal condition, a fungal mucosal or serosal condition, a viral mucosal or serosal condition, an autoimmune mucosal or serosal condition, an idiopathic mucosal or serosal condition, a hyperproliferative mucosal or serosal condition, a cancerous mucosal or serosal condition). Examples of mucosal or serosal conditions include pericarditis, Bowen's disease, stomatitis, prostatitis, sinusitis, allergic rhinitis, digestive disorders, peptic ulcers, esophageal ulcers, gastric ulcers, duodenal ulcer, espohagitis, gastritis, enteritis, enterogastric intestinal hemorrhage, toxic epidermal necrolysis syndrome, Stevens Johnson syndrome, fibrotic condition (e.g., cystic fibrosis), bronchitis, pneumonia (e.g., nosocomial pneumonia, ventilator-assisted pneumonia), pharyngitis, common cold, ear infections, sore throat, sexually transmitted diseases (e.g., syphilis, gonorrhea, herpes, genital warts, HIV, chlamydia), inflammatory bowel disease, colitis, hemorrhoids, thrush, dental conditions, oral conditions, conjunctivitis, and periodontal conditions. Generally, the treatment of mucosal or serosal conditions involves contacting the metal-containing material with the area of a mucosal or serosal region having the condition. Mucosal or serosal areas include, for example, the oral cavity, the nasal cavity, the colon, the small intestine, the large intestine, the stomach, and the esophagus. As an example, certain mucosal or serosal conditions can be treated by inhaling a free standing powder of the metal-containing material (e.g., with a dry powder inhaler). As another example, certain mucosal or serosal conditions can be treated by inhaling an aerosol containing the metal-containing material (e.g., with an inhaler). As an additional example, certain mucosal or serosal conditions can be treated by gargling or spraying a solution of the metal-containing material. As another example, certain mucosal or serosal conditions can be treated using a suppository. As a further example, certain mucosal or serosal conditions can be treated by an enema.

In embodiments in which the metal-containing material is used to treat hyperproliferation of cell growth (e.g., cancerous conditions, such as malignant tumors, or non-cancerous conditions, such as benign tumors), the metal-containing material can be used to induce apoptosis (programmed cell death), modulate matrix metalloproteinases (MMPs) and/or modulates cytokines by contacting affected tissue (e.g., a hyperplastic tissue, a tumor tissue or a cancerous lesion) with the metal-containing material. It has been observed that the metal-containing material (e.g., an antimicrobial, anti-biofilm, antibacterial, anti-inflammatory, antifungal, antiviral, anti-autoimmune, anti-cancer, pro-apoptosis, anti-proliferative, and/or MMP modulating, nanocrystalline and/or atomically disordered, silver-containing material) can be effective in preventing production of a high number of MMPs and/or cytokines by certain cells without necessarily reducing MMP and/or cytokine production by the same cells to about zero. It is believed, however, that in certain embodiments, the metal-containing material can be used to inhibit MMP and/or cytokine production (e.g., bring MMP and/or cytokine production to normal levels, desired levels, and/or about zero) in certain cells.

MMPs refer to any protease of the family of MMPs which are involved in the degradation of connective tissues, such as collagen, elastins, fibronectin, laminin, and other components of the extracellular matrix, and associated with conditions in which excessive degradation of extracellular matrix occurs, such as tumor invasion and metastasis. Examples of MMPs include MMP-2 (secreted by fibroblasts and a wide variety of other cell types) and MMP-9 (released by mononuclear phagocytes, neutrophils, corneal epithelial cells, tumor cells, cytotrophoblasts and keratinocytes). Cytokine refers to a nonimmunoglobulin polypeptide secreted by monocytes and lymphocytes in response to interaction with a specific antigen, a nonspecific antigen, or a nonspecific soluble stimulus (e.g., endotoxin, other cytokines). Cytokines affect the magnitude of inflammatory or immune responses. Cytokines can be divided into several groups, which include interferons, tumor necrosis factor (TNF), interleukins (IL-1 to IL-8), transforming growth factors, and the hematopoietic colony-stimulating factors. An example of a cytokine is TNF-α. A fibroblast is an area connective tissue cell which is a flat-elongated cell with cytoplasmic processes at each end having a flat, oval vesicular nucleus. Fibroblasts which differentiate into chondroblasts, collagenoblasts, and osteoblasts form the fibrous tissues in the body, tendons, aponeuroses, supporting and binding tissues of all sorts. Hyperplastic tissue refers to tissue in which there is an abnormal multiplication or increase in the number of cells in a normal arrangement in normal tissue or an organ. A tumor refers to spontaneous growth of tissue in which multiplication of cells is abnormal, uncontrolled and progressive. A tumor generally serves no useful function and grows at the expense of the healthy organism. A cancerous lesion is a tumor of epithelial tissue, or malignant, new growth made up of epithelial cells tending to infiltrate surrounding tissues and to give rise to metastases. As used in reference to the skin, a cancerous lesion means a lesion which may be a result of a primary cancer, or a metastasis to the site from a local tumor or from a tumor in a distant site. It may take the form of a cavity, an open area on the surface of the skin, skin nodules, or a nodular growth extending from the surface of the skin.

Conditions characterized by undesirable MMP activity include ulcers, asthma, acute respiratory distress syndrome, skin disorders, skin aging, keratoconus, restenosis, osteo- and rheumatoid arthritis, degenerative joint disease, bone disease, wounds, cancer including cell proliferation, invasiveness, metastasis (carcinoma, fibrosarcoma, osteosarcoma), hypovolemic shock, periodontal disease, epidermolysis bullosa, scleritis, atherosclerosis, multiple sclerosis, inflammatory diseases of the central nervous system, vascular leakage syndrome, collagenase induced disease, adhesions of the peritoneum, strictures of the esophagus or bowel, ureteral or urethral strictures, and biliary strictures. Excessive TNF production has been reported in diseases which are characterized by excessive MMP activity, such as autoimmune disease, cancer, cachexia, HIV infection, and cardiovascular conditions.

Forms of the Material and Methods of Applying the Material

In general, the metal-containing material can be in any desired form or formulation. For example, the material can be a coating on a substrate (e.g., in the form of a dressing, a coated medical implant), a free standing powder, a solution, or disposed within a pharmaceutically acceptable carrier.

In some embodiments, the metal-containing material can act as a preservative. In such embodiments, a form or formulation containing the metal-containing material can be prepared with or without additional preservatives. Moreover, in embodiments in which the metal-containing material acts as a preservative, the metal-containing material may be included in a therapeutic formulation containing other therapeutic agents (e.g., the metal-containing material may be included primarily in certain therapeutic compositions to act as a preservative).

Moreover, the material can be applied to the subject in any of a variety of ways, generally depending upon the form of the material as applied and/or the location of the condition to be treated. In general, the amount of material used is selected so that the desired therapeutic effect (e.g., reduction in the condition being treated) is achieved while the material introduces an acceptable level of toxicity (e.g., little or no toxicity) to the subject. Generally, the amount of the material used will vary with the conditions being treated, the stage of advancement of the condition, the age and type of host, and the type, concentration and form of the material as applied. Appropriate amounts in any given instance will be readily apparent to those skilled in the art or capable of determination by routine experimentation. In some embodiments, a single application of the material may be sufficient. In certain embodiments, the material may be applied repeatedly over a period of time, such as several times a day for a period of days, weeks, months or years.

Substrate Coatings

Examples of commercially available metal-containing materials include the Acticoat® family of dressings (Smith & Nephew, Hull, UK), which are formed of antimicrobial, anti-inflammatory atomically disordered, nanocrystalline silver-containing material coated on one or more substrates. Such dressings include the Acticoat® dressings, the Acticoat7® dressings, the Acticoat® moisture coating dressings, and the Acticoat® absorbent dressings.

A coating of a metal-containing material (e.g., an antimicrobial, atomically disordered, nanocrystalline silver-containing material) can be formed on a substrate using a desired technique. In certain embodiments, the coating is formed by depositing the material on the substrate surface using chemical vapor deposition, physical vapor deposition, and/or liquid phase deposition. Exemplary deposition methods include vacuum evaporation deposition, arc evaporation deposition, sputter deposition, magnetron sputter deposition and ion plating.

In some embodiments, the coating is prepared using physical vapor deposition. FIG. 1 shows a vapor deposition system 100 that includes a vacuum chamber 110, an energy source 120 (e.g., an electron beam source, an ion source, a laser beam, a magnetron source), a target 130 and a substrate 140. During operation, energy source 120 directs a beam of energy 122 to target 130, causing material 132 to be removed (e.g., by evaporation) from target 130 and directed to a surface 142 of substrate 140. At least a portion of the removed material 132 is deposited on surface 142.

In general, the values of the system parameters (e.g., the temperature of surface 142, the pressure of chamber 110, the angle of incidence of removed material 132 on surface 142, the distance between target 130 and surface 142) can be selected as desired. The temperature of surface 142 can be relatively low during the deposition process. For example, during the deposition process, the ratio of the temperature of substrate 140 to the melting point of the material forming target 130 (as determined in using Kelvin) can be about 0.5 or less (e.g., about 0.4 or less, about 0.35 or less, about 0.3 or less).

The pressure in chamber 110 can be relatively high. For example, vacuum evaporation deposition, electron beam deposition or arc evaporation, the pressure can be about 0.01 milliTorr or greater. For gas scattering evaporation (pressure plating) or reactive arc evaporation, the pressure in chamber 110 can be about 20 milliTorr or greater. For sputter deposition, the pressure in chamber 110 can be about 75 milliTorr or greater. For magnetron sputter deposition, the pressure in chamber 110 can be about 10 milliTorr or greater. For ion plating, the pressure in chamber 110 can be 200 milliTorr or greater.

The angle of incidence of removed material 132 on surface 142 ($\theta$) can be relatively low. For example, the angle of incidence of removed material 132 on surface 142 can be about 75° or less (e.g., about 60° or less, about 45° or less, about 30° or less).

The distance between target 130 and surface 142 can be selected based upon the values of the other system parameters. For example, the distance between target 130 and surface 142 can be about 250 millimeters or less (e.g., about 150 millimeters or less, 125 millimeters or less, about 100 millimeters or less, about 90 millimeters or less, about 80 millimeters or less, about 70 millimeters or less, about 60 millimeters or less, about 50 millimeters or less, about 40 millimeters or less).

As noted above, it is believed that, the metal-containing material, when contacted with an alcohol or water-based electrolyte, can be released into the alcohol or water-based electrolyte (e.g., as ions, atoms, molecules and/or clusters). It is also believed that the ability to release the metal (e.g., as atoms, ions, molecules and/or clusters) on a sustainable basis from a coating is generally dependent upon a number of factors, including coating characteristics such as composition, structure, solubility and thickness, and the nature of the environment in which the device is used. As the level of atomic disorder is increased, it is believed that the amount of metal species released per unit time increases. For example, a silver metal film deposited by magnetron sputtering at a ratio of substrate temperature to the target melting point of less than about 0.5 and a working gas pressure of about 0.93 Pascals (about seven milliTorr) releases approximately $\frac{1}{3}$ of the silver ions that a film deposited under similar conditions, but at four Pascals (about 30 milliTorr), will release over 10 days. Coatings formed with an intermediate structure (e.g., lower pressure, lower angle of incidence etc.) have been observed to have metal (e.g., silver) release values intermediate to these values as determined by bioassays. In general, to obtain relatively slow release of the metal, the coating should have a relatively low degree of atomic disorder, and, to obtain relatively fast release of the metal, the coating should have a relatively high degree of atomic disorder.

For continuous, uniform coatings, the time for total dissolution is generally a function of coating thickness and the nature of the environment to which the coating is exposed. The release of metal is believed to increase approximately linearly as the thickness of the coating is increased. For example, it has been observed that a two fold increase in coating thickness can result in about a two fold increase in longevity.

In certain embodiments, it is possible to manipulate the degree of atomic disorder, and therefore the metal release from a coating, by forming a thin film coating with a modulated structure. For example, a coating deposited by magnetron sputtering such that the working gas pressure was relatively low (e.g., about two Pascals or about 15 milliTorr) for about 50% of the deposition time and relatively high (e.g., about four Pascals or 30 milliTorr) for the remaining time, can result in a relatively rapid initial release of metal (e.g., ions, clusters, atoms, molecules), followed by a longer period of slow release. This type of coating is can be particularly effective on devices such as urinary catheters for which an initial rapid release is advantageous to achieve quick antimicrobial concentrations followed by a lower release rate to sustain the concentration of metal (e.g., ions, clusters, atoms, molecules) over a period of weeks.

It is further believed that the degree of atomic disorder of a coating can be manipulated by introducing one or more dissimilar materials into the coating. For example, one or more gases can be present in chamber 110 during the deposition process. Examples of such gases include oxygen-containing gases (e.g., oxygen, air, water), nitrogen-containing gases (e.g., nitrogen), hydrogen-containing gases (e.g., water, hydrogen), boron-containing gases (e.g., boron), sulfur-containing gases (e.g., sulfur), carbon-containing gases (e.g., carbon monoxide, carbon dioxide), phosphorus-containing gases, silicon-containing gases, and halogen-containing gases (e.g., fluorine, chlorine, bromine, iodine). The additional gas(es) can be co-deposited or reactively deposited with material 132. This can result in the deposition/formation of an oxide, hydroxide, nitride, carbide, phosphide, silicate, boride, sulfide, hydride, nitrate, carbonate, alkali thiosulphate (e.g., sodium thiosulphate, potassium thiosulphate), myristate, sorbate, stearate, oleate, glutonate, adipate, silicate, phosphide, sulfadiazine, acetate, lactate, citrate and/or halide material (e.g., an oxide of a metal-containing material, a hydroxide of a metal-containing material, a nitride of a metal-containing material, a carbide of a metal-containing material, a phosphide of a metal-containing material, a silicate of a metal-containing material, a boride of a metal-containing material, a sulfide of a metal-containing material, a hydride of a metal-containing material, a halide of a metal-containing material, a nitrate of a metal-containing material, a carbonate of a metal-containing material, a myristate of a metal-containing material, a sorbate of a metal-containing material, a stearate of a metal-containing material, an oleate of a metal-containing material, a glutonate of a metal-containing material, an adipate of a metal-containing material, a silicate of a metal-containing material, a phosphide of a metal-containing material, a sulfide of a metal-containing material, a sulfadiazine of a metal-containing material, a sulfadiazine of a metal-containing material, an acetate of a metal-containing material, a lactate of a metal-containing material, a citrate of a metal-containing material, an alkali metal thiosulphate (e.g., sodium metal thiosulphate, potassium metal thiosulphate) of a metal-containing material). Without wishing to be bound by theory, it is believed that atoms and/or molecules of the additional gas(es) may become absorbed or trapped in the material, resulting in enhanced atomic disorder. The additional gas(es) may be continuously supplied during deposition, or may be pulsed to (e.g., for sequential deposition). In embodiments, the material formed can be constituted of a material with a ratio of material 132 to additional gas(es) of about 0.2 or greater. The presence of dissimilar atoms or molecules in the coating can enhance the degree of atomic disorder of the coating due to the difference in atomic radii of the dissimilar constituents in the coating.

The presence of dissimilar atoms or molecules in the coating may also be achieved by co-depositing or sequentially depositing one or more additional metal elements (e.g., one or more additional antimicrobial metal elements). Such additional metal elements include, for example, Au, Pt, Ta, Ti, Nb, Zn, V, Hf, Mo, Si, Al, and other transition metal elements. It is believed that the presence of dissimilar metal elements (one or more primary metal elements and one or more additional metal elements) in the coating can reduce atomic diffusion and stabilize the atomically disordered structure of the coating. A coating containing dissimilar metal elements can be formed, for example, using thin film deposition equipment with multiple targets. In some embodiments, sequentially deposited layers of the metal elements are discontinuous (e.g., islands within a the primary metal). In certain embodiments, the weight ratio of the additional metal(s) to the primary metal(s) is greater than about 0.2.

While FIG. 1 shows one embodiment of a deposition system, other embodiments are possible. For example, the deposition system can be designed such that during operation the substrate moves along rollers. Additionally or alternatively, the deposition system may contain multiple energy sources, multiple targets, and/or multiple substrates. The multiple energy sources, targets and/or substrates can be, for example, positioned in a line, can be staggered, or can be in an array.

In certain embodiments, two layers of the material are deposited on the substrate to achieve an optical interference effect. Alternatively, the two layers can be formed of different materials, with the outer (top) of the two layers being formed of an antimicrobial, atomically disordered, nanocrystalline silver-containing material, and the inner of the two layers having appropriate reflective properties so that the two layers can provide an interference effect (e.g., to monitor the thickness of the outer (top) of the two layers).

The substrate can be selected as desired. The substrate may be formed of one layer or multiple layers, which may be formed of the same or different materials.

In certain embodiments, the substrate can include one or more layers containing a bioabsorbable material. Bioabsorbable materials are disclosed, for example, in U.S. Pat. No. 5,423,859. In general, bioabsorbable materials can include natural bioabsorbable polymers, biosynethetic bioabsorbable polymers and synthetic bioabsorbable polymers. Examples of synthetic bioabsorbable polymers include polyesters and polylactones (e.g., polymers of polyglycolic acid, polymers of glycolide, polymers of lactic acid, polymers of lactide, polymers of dioxanone, polymers of trimethylene carbonate, polyanhydrides, polyesteramides, polyorthoesters, polyphosphazenes, and copolymers of the foregoing). Examples of natural bioabsorbable polymers include proteins (e.g., albumin, fibrin, collagen, elastin), polysaccharides (e.g., chitosan, alginates, hyaluronic acid). Examples of biosynthetic polymers include polyesters (e.g., 3-hydroxybutyrate polymers).

In some embodiments, the substrate includes multiple layers (e.g., two layers, three layers, four layers, five layers, six layers, seven layers, eight layers, nine layers, 10 layers). The layers can be laminated together (e.g., by thermal fusing, stitching and/or ultrasonic welding).

One or more layers (e.g., an outer layer) of a multi-layer substrate can be formed of a perforated (and optionally non-adherent) material (e.g., a woven material or a non-woven material) that can allow fluid to penetrate or diffuse therethrough. Such materials include, for example, cotton, gauze, polymeric nets (e.g., polyethylene nets, nylon nets, polypropylene nets, polyester nets, polyurethane nets, polybutadiene nets), polymeric meshes (e.g., polyethylene meshes, nylon meshes, polypropylene meshes, polyester meshes, polyurethane meshes, polybutadiene meshes) and foams (e.g., an open cell polyurethane foam). Examples of commercially available materials include DELNET™ P530 non-woven polyethylene veil (Applied Extrusion Technologies, Inc., Middletown, Del.), Exu-Dry CONFORMANT2™ non-woven polyethylene veil (Frass Survival Systems, Inc., NY, N.Y.), CARELLE™ material (Carolina Formed Fabrics Corp.), NYLON90™ material (Carolina Formed Fabrics Corp.), N-TERFACE™ material (Winfield Laboratories, Inc., Richardson, Tex.), HYPOL™ hydrophilic polyurethane foam (W. R. Grace & Co., NY, N.Y.).

One or more layers (e.g., an inner layer) of a multi-layer substrate can be formed of an absorbent material (e.g., a woven material or a non-woven material) formed of, for example, rayon, polyester, a rayon/polyester blend, polyester/cotton, cotton and/or cellulosic fibers. Examples include creped cellulose wadding, air felt, air laid pulp fibers and gauze. An example of a commercially available material is SONATRA™ 8411 70/30 rayon/polyester blend (Dupont Canada, Mississauga, Ontario).

One or more layers (e.g., an outer layer) of a multi-layer substrate can be formed of an occlusive or semi-occlusive material, such as an adhesive tape or polyurethane film (e.g., to secure the device to the skin and/or to retain moisture).

In some embodiments, the layers in a multi-layer substrate are laminated together (e.g., at intermittent spaced locations) by ultrasonic welds. Typically, heat (e.g., generated ultrasonically) and pressure are applied to either side of the substrate at localized spots through an ultrasonic horn so as to cause flowing of at least one of the plastic materials in the first and second layers and the subsequent bonding together of the layers on cooling. The welds can be formed as localized spots (e.g., circular spots). The spots can have a diameter of about 0.5 centimeter or less.

The shape of the substrate can generally be varied as desired. For example, the substrate can be in the shape of a film, a fiber or a powder.

The substrate/coating article can be used in a variety of articles. For example, the article can be in the shape of a medical device. Exemplary medical devices include wound closure devices (e.g., sutures, staples, adhesives), tissue repair devices (e.g., meshes, such as meshes for hernia repair), prosthetic devices (e.g., internal bone fixation devices, physical barriers for guided bone regeneration, stents, valves, electrodes), tissue engineering devices (e.g., for use with a blood vessel, skin, a bone, cartilage, a liver), controlled drug delivery systems (e.g., microcapsules, ion-exchange resins) and wound coverings and/or fillers (e.g., alginate dressings, chitosan powders). In some embodiments, the article is a transcutaneous medical device (e.g., a catheter, a pin, an implant), which can include the substrate/coating supported on, for example, a solid material (e.g., a metal, an alloy, latex, nylon, silicone, polyester and/or polyurethane). In some embodiments, the article is in the form of a patch (e.g., a patch having an adhesive layer for adhering to the skin, such as a transdermal patch).

Subsequent to deposition, the material can optionally be annealed. In general, the anneal is conducted under conditions to increase the stability (e.g., shelf life) of the material while maintaining the desired therapeutic activity of the material. In certain embodiments, the material can be annealed at a temperature of about 200° C. or less (e.g., about room temperature).

The substrate/coating is typically sterilized prior to use (e.g., without applying sufficient thermal energy to anneal out the atomic disorder). The energy used for sterilization can be, for example, gamma radiation or electron beam radiation. In some embodiments, ethylene oxide sterilization techniques are used to sterilize the substrate/coating.

Free Standing Powders

A free standing powder can be prepared by, for example, cold working or compressing to impart atomic disorder to the powder. In certain embodiments, a free standing powder is prepared by forming a coating of the material as described above, and then removing the material from the surface of the substrate. For example, the material can be scraped from the surface of the substrate by one or more scrapers. In embodiments in which the substrate moves during deposition of the material, the scrapers can remove the material as the substrate moves. The scrapers can be, for example, suspended above the substrate. Such scrapers can be, for example, weighted and/or spring loaded to apply pressure sufficient to remove the material as the substrate moves. In some embodiments (e.g., when a continuous belt is used), the scrapers can be located above the end rollers to remove the material with a reverse dragging action as the substrate rounds the end roller.

A free standing powder can be used to treat a condition in various ways. As an example, the powder can sprinkled onto the subject's skin. As another example, the powder can be inhaled using an inhaler, such as a dry powder inhaler. In some embodiments, a dry powder can be in the form of an aerosol, which contains, for example, at least about 10 (e.g., at least about 20, at least about 30) weight percent and/or at most about 99 (e.g., at most about 90, at most about 80, at most about 70, at most about 60, at most about 50) weight percent of the dry powder.

In certain embodiments (e.g., when the free standing powder is inhaled), the average particle size of the free standing powder is selected to reduce the likelihood of adverse reaction(s) of the particles in the tissue and/or to deposit the powder onto specific anatomical locations (e.g., tissue contacted by the free standing powder during inhalation). In some embodiments, the average particle size is selected (e.g., less than about 10 microns) so that a relatively small amount of the particles get into the lower respiratory tract. In embodiments, a free standing powder can have an average particle size of less than about 10 microns (e.g., less than about eight microns, less than about five microns, less than about two microns, less than about one micron, less than about 0.5 micron) and/or at least about 0.01 micron (e.g., at least about 0.1 micron, at least about 0.5 micron).

Powder Impregnated Materials

The metal-containing material can be in the form of a powder impregnated material. Such powder impregnated materials can, for example, be in the form of a hydrocolloid having the free standing powder blended therein. A powder impregnated material can be, for example, in the form of a dressing, such as a hydrocolloid dressing.

Solutions

The material can be in the form of a solution (e.g., a solvent-based solution). The solution can be formed, for example, by dissolving a free standing powder of the material in a solvent for the powder. As an example, a container (e.g., a tea bag-type container) with the free standing powder within it can be immersed in the water or solvent. As another example, a substrate (e.g., in the form of a strip or a bandage) carrying the material can be immersed in the solvent. In certain embodiments, it can be preferable to form a solution by dissolving a free standing powder of the material in a solvent because this can be a relatively convenient approach to forming a solution. A solution also refers to a suspension that contains one or more metal-containing materials. As an example, a suspension can be formed by dissolving a metal-containing material (e.g., a nanocrystalline silver-containing material) in a liquid (e.g., water) for a period of time (e.g., several days) so that particles of the metal-containing material are suspended (e.g., by Brownian motion) in the liquid. In some embodiments, a suspended particle of metal-containing material can have, for example, a diameter of the order of from about 10 nanometers to about 20 nanometers. A solution also refers to a dispersion that contains one or more metal-containing materials.

In certain embodiments, the solution containing the material is contacted with the subject relatively soon after formation of the solution. For example, the solution containing the material can be contacted with the subject within about one minute or less (e.g., within about 30 seconds or less, within about 10 seconds or less) of forming the solution containing the material. In some embodiments, a longer period of time lapses before the solution containing the material is contacted with the subject. For example a period of time of at least about 1.5 minutes (e.g., at least about five minutes, at least about 10 minutes, at least about 30 minutes, at least about one hour, at least about 10 hours, at least about a day, at least about a week) lapses between the time the solution containing the material is formed and the solution containing the material is contacted with the subject.

In some embodiments, lowering the pH of the solution (e.g., to less than about 6.5, such as from about 3.5 to about 6.5) can allow for a higher concentration of the dissolved material and/or a faster rate of dissolution. The pH of the solution can be lowered, for example, by adding acid to the solution (e.g., by adding $CO_2$ to the solution to form carbonic acid).

A solution containing the material can be contacted with the subject with or without the use of a device. As an example, a solution containing the material can be contacted with the skin, mouth, ears or eyes as a rinse, a bath, a wash, a gargle, a spray, and/or drops. As another example, the solution can be injected using a small needle injector and/or a needleless injector. As an additional example, a solution containing the material can be formed into an aerosol (e.g., an aerosol prepared by a mechanical mister, such as a spray bottle or a nebulizer), and the aerosol can be contacted with the subject using an appropriate device (e.g., a hand held inhaler, a mechanical mister, a spray bottle, a nebulizer, an oxygen tent). As a further example, a solution containing the material can be contacted with the second location via a catheter.

In embodiments in which onychomycosis is being treated, the method can include first hydrating the nail with urea (1-40%) or lactic acid (10-15%), followed by treatment with the metal-containing material, which may contain an appropriate solvent (e.g., DMSO) for penetration through the nail. Alternatively or additionally, onychomycosis can be treated by injecting (e.g., via a needleless injector and/or a needle) the metal-containing material to the affected area.

Typically, the solvent is a relatively hydrophilic solvent. Examples of solvents include water, DMSO and alcohols. In certain embodiments, a water-based solution is a buffered solution. In some embodiments, a water-based solution contains carbonated water. In embodiments, more than one solvent can be used.

In some embodiments, the solution can contain about 0.001 weight percent or more (e.g., about 0.01 weight percent or more, about 0.02 weight percent or more, about 0.05 weight percent or more, about 0.1 weight percent or more, about 0.2 weight percent or more, about 0.5 weight percent or more, about one weight percent or more) of the material and/or about 10 weight percent or less (e.g., about five weight percent or less, about four weight percent or less, about three weight percent or less, about two weight percent or less, about one weight percent or less) of the material.

Pharmaceutical Carrier Compositions

The metal-containing material can disposed (e.g., suspended) within a pharmaceutically acceptable carrier. The formulation can be, for example, a semi-solid, a water-based hydrocolloid, an oil-in-water emulsion, a water-in-oil emulsion, a non-dried gel, and/or a dried gel. Typically, when disposed in a pharmaceutically acceptable carrier, the metal-containing material is applied to the skin.

Examples of pharmaceutically acceptable carriers include creams, ointments, gels, sprays, solutions, drops, powders, lotions, pastes, foams and liposomes.

The formulation can contain about 0.01 weight percent or more (e.g., about 0.1 weight percent or more, about 0.5 weight percent or more, about 0.75 weight percent or more, about one weight percent or more, about two weight percent or more, about five weight percent or more, about 10 weight percent or more) of the metal-containing material and/or about 50 weight percent or less (e.g., about 40 weight percent or less, about 30 weight percent or less, about 20 weight percent or less, about 20 weight percent or less, about 15 weight percent or less, about 10 weight percent or less, about five weight percent or less) of the metal-containing material.

In certain embodiments, the metal-containing material can be effectively used in the oral cavity when in the form of an article (e.g., a tape, a pill, a capsule, a tablet or lozenge) that is placed within the oral cavity (e.g., so that the subject can suck on the tape, pill, capsule, tablet or lozenge). In some embodiments, the article can be a sustained release article (e.g., a sustained release capsule) which can allow the metal-containing material to be released at a predetermined rate (e.g., a relatively constant rate). In some embodiments, an article can include a material (e.g., in the form of a coating and/or in the form of a matrix material) that allows the article to pass through certain portions of the gastrointestinal system with relatively little (e.g., no) release of the metal-containing material, but that allows a relatively large amount of the metal-containing material to be released in a desired portion of the gastrointestinal system. As an example, the article can be an enteric article (e.g., an enteric coated tablet) so that the article to passes through the stomach with little (e.g., no) metal-containing material being released, and so that the metal-containing material is relatively easily released by the article in the intestines.

Formulations can optionally include one or more components which can be biologically active or biologically inactive. Examples of such optional components include base components (e.g., water and/or an oil, such as liquid paraffin, vegetable oil, peanut oil, castor oil, cocoa butter), thickening agents (aluminum stearate, hydrogen lanolin), gelling agents, stabilizing agents, emulsifying agents, dispersing agents, suspending agents, thickening agents, coloring agents, perfumes, excipients (starch, tragacanth, cellulose derivatives, polyethylene glycols, silicones, bentonites, silicic acid, talc), foaming agents (e.g., surfactants), surface active agents, preservatives (e.g., methyl paraben, propyl paraben) and cytoconductive agents (e.g., betaglucan). In some embodiments, a formulation includes petrolatum. In certain embodiments, a pharmaceutical carrier composition can include a constituent (e.g., DMSO) to assist in the penetration of skin.

While the foregoing has described embodiments in which a single condition is treated, in some embodiments multiple conditions can be treated. The multiple conditions can be the same type of condition (e.g., multiple skin or integument conditions) or different types of conditions. For example, a dressing formed of one or more substrates coated with an appropriate metal-containing material (e.g., antimicrobial, atomically disordered, silver-containing material) can be applied to an area of the skin having multiple skin or integument conditions (e.g., a burn and psoriasis) so that the metal-containing material treats the multiple skin or integument conditions.

Moreover, while the foregoing has described embodiments that involve one method of contacting a subject with the metal-containing material, in other embodiments, more than one method of contacting a subject with the metal-containing material can be used. For example, the methods can include one or more of ingestion (e.g., oral ingestion), injection (e.g., using a needle, using a needleless injector), topical administration, inhalation (e.g., inhalation of a dry powder, inhalation of an aerosol) and/or application of a dressing.

Furthermore, while the foregoing has described embodiments in which one form of the metal-containing material is used, in other embodiments, more than one form of the metal-containing material can be used. For example, the methods can include using the metal-containing material in the form of a coating (e.g., a dressing), a free standing powder, a solution and/or a pharmaceutical carrier composition.

Moreover, the metal-containing material can be used in various industrial applications. For example, the metal-containing material can be used to reduce and/or prevent microbial growth on industrial surfaces (e.g., industrial surfaces where microbial growth may occur, such as warm and/or moist surfaces). Examples of industrial surfaces include heating pipes and furnace filters. In certain embodiments, the metal-containing material can be disposed (e.g., coated or sprayed) on the surface of interest to reduce and/or prevent microbial growth. This can be advantageous in preventing the spread of microbes via, for example, heating and/or air circulation systems within buildings.

The following examples are illustrative and not intended as limiting.

EXAMPLES

Treatment of Hyperoroliferative Skin Conditions

Example 1

Preparation of Nanocrystalline Silver Coatings on Dressings

This example shows the preparation of a bilayer nanocrystalline silver coating on a dressing material. A high density polyethylene dressing, DELNET™ or CONFORMANT 2™ was coated with a silver base layer and a silver/oxide top layer to generate a coloured anti-microbial coating having indicator value. The coating layers were formed by magnetron sputtering under the conditions set out in the following table.

| Sputtering Conditions: | Base Layer | Top Layer |
| --- | --- | --- |
| Target | 99.99% Ag | 99.99% Ag |
| Target Size | 20.3 cm diameter | 20.3 cm diameter |
| Working Gas | 96/4 wt % Ar/$O_2$ | 96/4 wt % Ar/$O_2$ |
| Working Gas Pressure | 5.33 Pa (40 mT) | 5.33 Pa (40 mT) |
| Power | 0.3 kW | 0.15 kW |
| Substrate Temperature | 20° C. | 20° C. |
| Base Pressure | $3.0 \times 10^{-6}$ Torr | $3.0 \times 10^{-6}$ Torr |
| Anode/Cathode Distance | 100 mm | 100 mm |
| Sputtering Time | 7.5-9 min | 1.5 min |
| Voltage | 369-373 V | 346 V |

The resulting coating was blue in appearance. A fingertip touch was sufficient to cause a colour change to yellow. The base layer was about 900 nm thick, while the top layer was 100 nm thick.

To establish that silver species were released from the coated dressings, a zone of inhibition test was conducted. Mueller Hinton agar was dispensed into Petri dishes. The agar plates were allowed to surface dry prior to being inoculated with a lawn of Staphylococcus aureus ATCC#25923. The inoculant was prepared from Bactrol Discs (Difco, M.), which were reconstituted as per the manufacturer's directions. Immediately after inoculation, the coated materials to be tested were placed on the surface of the agar. The dishes were incubated for 24 hr. at 37° C. After this incubation period, the zone of inhibition was calculated (corrected zone of inhibition=zone of inhibition–diameter of the test material in contact with the agar). The results showed a corrected ZOI of about 10 mm, demonstrating good release of silver species.

The coating was analyzed by nitric acid digestion and atomic absorption analysis to contain 0.24+/−0.04 mg silver per mg high density polyethylene. The coating was a binary alloy of silver (>97%) and oxygen with negligible contaminants, based on secondary ion mass spectroscopy. The coating, as viewed by SEM, was highly porous and consisted of equiaxed nanocrystals organized into coarse columnar structures with an average grain size of 10 nm. Silver release studies in water demonstrated that silver was released continuously from the coating until an equilibrium concentration of about 66 mg/L was reached (determined by atomic absorption), a level that is 50 to 100 times higher than is expected from bulk silver metal (solubility $\leq$ 1 mg/L).

By varying the coating conditions for the top layer to lengthen the sputtering time to 2 min, 15 sec., a yellow coating was produced. The top layer had a thickness of about 140 nm and went through a colour change to purple with a fingertip touch. Similarly, a purple coating was produced by shortening the sputtering time to 1 min, to achieve a top layer thickness of about 65 nm. A fingertip touch caused a colour change to yellow.

To form a three layer dressing, two layers of this coated dressing material were placed above and below an absorbent core material formed from needle punched rayon/polyester (SONTARA™ 8411). With the silver coating on both the first and third layers, the dressing may be used with either the blue coating side or the silver side in the skin facing position. For indicator value, it might be preferable to have the blue coating visible. The three layers were laminated together by ultasonic welding to produce welds between all three layers spaced at about 2.5 cm intervals across the dressing. This allowed the dressing to be cut down to about 2.5 cm size portions for smaller dressing needs while still providing at least one weld in the dressing portion.

The coated dressings were sterilized using gamma radiation and a sterilization dose of 25 kGy. The finished dressing was packaged individually in sealed polyester peelable pouches, and has shown a shelf life greater than 1 year in this form. The coated dressings can be cut in ready to use sizes, such as 5.1×10.2 cm strips, and slits formed therein before packaging. Alternatively, the dressings may be packaged with instructions for the clinician to cut the dressing to size and form the desired length of the slit for the medical device.

Additional silver coated dressings were prepared in a full scale roll coater under conditions to provide coatings having the same properties set out above, as follows:

the dressing material included a first layer of silver coated DELNET, as set out above, laminated to STRATEX, AET, 8.0NP$_2$-A/QW, which is a layer of 100% rayon on a polyurethane film.

Silver Foam Dressing—three layers of silver coated high density polyethylene prepared as above, alternating with two layers of polyurethane foam, L-00562-6 Medical Foam, available from Rynel Ltd., Bootbay, Me., USA.

Example 2

Preparation of Nanocrystalline Silver Powders

Nanocrystalline silver powder was prepared by preparing silver coatings on silicon wafers, under the conditions set forth in the table above, and then scraping the coating off using a glass blade.

Nanocrystalline silver powder was also prepared by sputtering silver coatings on silicon wafers using Westaim Biomedical NGRC unit, and then scraping the coating off. The sputtering conditions were as follows:

| Target: | 99.99% Ag |
| Target Size: | 15.24 cm × 1216.125 cm |
| Working Gas: | 75:25 wt % Ar/O$_2$ |
| Working Gas Pressure: | 40 mTorr |
| Total Current: | 40 A |
| Base Pressure: | $5.0 \times 10^{-5}$ Torr |
| Sandvik Belt Speed: | 340 mm/min |
| Voltage: | 370 V |

The powder has a particle size ranging from 2 μm to 100 μm, with crystallite size of 8 to 10 nm, and demonstrated a positive rest potential.

Example 3

Treatment of Psoriasis

This patient was a 58 year old female with psoriatic plaques covering up to sixty percent of her body. For this patient, psoriatic plaques first occurred ten years ago and have been treated with the following:

1. Adrenal corticosteroids. Injections gave relief from pruritus and general discomfort. Treatments led to a rebound effect; i.e. psoriasis would flare up after treatments wore off. Corticosteroids were discontinued.

2. UV Light and Methotrexate treatments. UV light treatments were given in conjunction with methotrexate. The UV light treatments caused burns and new lesions. The methotrexate caused severe nausea. Both treatments were discontinued.

3. Ice Cap Spray. This treatment contained a potent corticosteroid, and gave some relief but it was taken off the market and is no longer available.

4. Soriatone (acetretin 10 mg). This systemic retinoid treatment was associated with joint aches and was discontinued.

5. Diet. The patient was attempting to control the disease through diet.

Nanocrystalline silver was tested as follows. Nanocrystalline silver was deposited on sheets of high-density polyethylene (HDPE) using a vapour deposition process as set forth in Example 1.

Two sheets of this coated HDPE were laminated together around a core of non-woven rayon polyester, as set forth in Example 1. A 50 mm×50 mm (2"×2") piece of this composite material was saturated with water and placed centrally on a one and a half year old 150 mm×100 mm (6"×4") psoriatic plaque on the patient's flank. The nanocrystalline silver coated material was covered with a piece of low moisture vapour transmission thin polymer film. The polymer sheet extended 50 mm (2") beyond the nanocrystalline silver coated HDPE to provide control data regarding occlusion of the psoriatic plaque.

The dressing was removed after three days. There was no discernible change in the plaque at this time. However two days later the area that was covered with the nanocrystalline silver had the appearance of normal skin while the rest of the plaque was still rough and unchanged, including the untreated but occluded area.

The nanocrystalline silver therapy caused the treated psoriatic plaque to resolve.

Example 4

Treatment of Psoriasis

The subject was a 58 year old female with psoriatic plaques over up to sixty percent of her body. Psoriatic plaques had first occurred 10 years ago and had been treated with the following:

1. Adrenal corticosteroids. Injections gave relief from pruritus and general discomfort. Treatments led to a rebound effect i.e. psoriasis would flare up after treatments wore off. Corticosteroids were discontinued.

2. UV Light and Methotrexate treatments. UV light treatments were given in conjunction with methotrexate. The UV light treatments caused burns and new lesions. The methotrexate caused severe nausea. Both treatments were discontinued.

3. Ice Cap Spray. This treatment contained a potent corticosteroid, and gave some relief but it was taken off the market and is no longer available.

4. Soriatone (acetretin 10 mg). This systemic retinoid treatment was associated with joint aches and was discontinued.

5. Diet. The patient was attempting to control the disease through diet.

Nanocrystalline silver was tested as follows. Nanocrystalline silver was deposited on sheets of high-density polyethylene (HDPE) using a vapour deposition process as set forth in Example 1 (top layer). Two sheets of this coated HDPE were laminated together around a core of non-woven rayon polyester, as set forth in Example 1. A 50 mm×50 mm (2"×2") piece of this composite material was saturated with water and placed centrally on a 125 mm×100 mm (5"×4") psoriatic plaque on the patient's upper left thigh. The nanocrystalline silver coated material was covered with a piece of low moisture vapour transmission thin polymer film. The polymer sheet extended 50 mm (2") beyond the nanocrystalline silver coated HDPE to provide control data regarding occlusion of the psoriatic plaque.

The dressing was removed and the plaque examined after two days. The area that was covered with the nanocrystalline silver was free of scaling and only slightly erythenatous while the rest of the plaque was still erythenatous and scaly, including the untreated but occluded area. The plaque was redressed with a similar 50 mm×50 mm (2"×2") piece of nanocrystalline silver coated dressing, which was left in place for a further period of 2 days. The area that was covered with the nanocrystalline silver remained free of scale and only slightly erythenatous, while the rest of the plaque was still erythenatous and scaly, including the area under the occlusive film.

The nanocrystalline silver therapy caused the treated psoriatic plaque to resolve.

Example 5

Preparation of Nanocrystalline Gels

A commercial carboxymethyl cellulose/pectin (Duoderm Convatec™) was combined with nanocrystalline silver powder prepared as in Example 2 to produce a gel with 0.1% w/v. silver. Carboxymethyl cellulose (CMC) fibers were coated by magnetron sputtering, under conditions similar to those set out in Example 1 for the top layer to produce a defective nanocrystalline silver coating. The CMC was then gelled in water by adding 2.9 g to 100 mL volume. An alginate fibrous substrate was directly coated with a defective nanocrystalline silver coating by magnetron sputtering under coating conditions similar to those set forth in Example 1 for the top layer. The alginate (5.7 g) was added to 100 mL volume of water to create a gel. A commercial gel containing CMC and alginate (Purilon gel Coloplast™) was mixed with an atomic disordered nanocrystalline silver powder prepared as in Example 2 to give a gel product with 0.1% w/v silver. A commercially available gel (Lubriderm™—glyceryl polymethacrylate) was blended with atomic disordered nanocrystalline silver powder prepared as in Example 2, to prepare a gel with a silver content of 0.1% w/v. A further gel was formulated with, on w/v basis, 0.1% methyl paraben, 0.02% propyl paraben, 0.5% polyvinyl alcohol (Airvol™ PVA 540), 2% CMC, 0.1% nanocrystalline silver powder prepared as in Example 2, and was brought up to 1000 g with water.

Treatment of Inflammatory Skin Conditions

Example 1

Preparation of Nanocrystalline Silver Coatings on Dressings

This example shows the preparation of a bilayer nanocrystalline silver coating on a dressing material. A high density polyethylene dressing, DELNET™ or CONFORMANT 2™ was coated with a silver base layer and a silver/oxide top layer to generate a coloured antimicrobial coating having indicator value as described in Example 1 of the Treatment of Hyperproliferative Skin conditions examples. The coating layers were formed by magnetron sputtering under the conditions set out in the following table.

Example 2

Preparation of Nanocrystalline Silver Coating on HDPE Mesh

The silver coated mesh was produced, as set forth in Example 1, by sputtering silver onto Delnet, a HDPE mesh (Applied Extrusion Technologies, Inc., Middletown, Del., USA) using Westaim Biomedical TMRC unit under the following conditions:

| | |
|---|---|
| Target: | 99.99% Ag |
| Target Size: | 15.24 cm × 152.4 cm |
| Working Gas: | 99.375:0.625 wt % Ar/O$_2$ |
| Working Gas Pressure: | 5.33 Pascals (40 mTorr) |
| Total Current: | 22 A |
| Base Pressure: | 5.0 × 10$^{-5}$ Torr |
| Sandvik Belt Speed: | 577 mm/min |
| Voltage: | 367 V |

The coating was tested and found to have a weight ratio of reaction product to silver of between 0.05 and 0.1. The dressing was non-staining to human skin.

Example 3

Preparation of Atomic Disordered Nanocrystalline Silver Powders

Nanocrystalline silver coatings were prepared by sputtering silver in an oxygen-containing atmosphere directly onto an endless stainless steel belt of a magnetron sputtering roll coater, or onto silicon wafers on the belt. The belt did not need to be cooled. The coatings were scraped off with the belt with suspended metal scrapers as the belt rounded the end rollers. For the coated silicon wafers, the coatings were scraped off with a knife edge. The sputtering conditions were as follows:

| | |
|---|---|
| Target: | 99.99% Ag |
| Target Size: | 15.24 cm × 1216.125 cm |
| Working Gas: | 75:25 wt % Ar/O$_2$ |
| Working Gas Pressure: | 5.33 Pascals (40 milliTorr) |
| Total Current: | 40 A |
| Base Pressure: | 5.0 × 10$^{-5}$ Torr (range: 1 × 10$^{-4}$-9 × 10$^{-7}$ Torr or 1 × 10$^{-2}$-1.2 × 10$^{-4}$ Pa) |
| Sandvik Belt Speed: | 340 mm/min |
| Voltage: | 370 V |

Note—pressure conversions to Pa herein may not be accurate, most accurate numbers are in torr, mTorr units.

The powder had a particle size ranging from 2 μm to 100 μm, with grain or crystallite size of 8 to 10 nm (i.e., nanocrystalline), and demonstrated a positive rest potential.

Similar atomic disordered nanocrystalline silver powders were formed as set forth hereinabove by magnetron sputtering onto cooled steel collectors, under conditions taught in the prior Burrell et al. patents to produce atomic disorder.

Example 4

In vitro Activity of Silver Solution Against *Propionibacterium acne*

An in vitro test was conducted to determine if silver solutions according to the present invention effectively control *Propionibacterium acne*. The silver solution was obtained by static elution of Acticoat™ Burn Wound Dressing (lot #: 00403A-05, Westaim Biomedical Corp., Fort Saskatchewan, Canada) with nanopure water in a ratio of one square inch of dressing in five milliliters of water for 24 hours at room temperature. The silver concentration of the silver solution was determined by an atomic absorption method. The silver elute was diluted with nanopure water to 20 μg/ml. The *Propionibacterium acne* (ATCC No. 0919) was provided by Biofilm Research Group, University of Calgary.

The inoculum was prepared by inoculating freshly autoclaved and cooled tubes of Tryptic soy broth (TSB) with *P. acne* and incubating them for 2 days at 37° C. in an anaerobic jar. At this time, the optical density of the suspensions was ~0.3 at a wavelength of 625 nm.

The bacterial suspension (100 μL) was mixed with 100 μL of the silver solution being tested. The final concentration of silver in these mixtures was 10 μg/ml. The mixtures were incubated in an anaerobic jar at 37° C. for two hours. The silver was neutralized by addition of 0.4% STS (0.85% NaCl, 0.4% Sodium thioglycolate, 1% Tween™ 20) and the solution was serially 10-fold diluted with phosphate-buffered saline. 20 μL aliquots of the original solution and subsequent dilutions were plated onto TSA drop plates. The drops were allowed to dry and the plates were incubated in an anaerobic jar at 37° C. for 72 hours at which time the colonies were counted. The control consisted of 100 μL of bacterial suspension mixed with 100 μL of nanopure water and treated as above.

The results showed that the silver solution according to the present invention, at a final concentration of 10 μg/ml, gave 4.3 logarithm reduction in viable *P. acne* counts in two hours.

Example 5

Treatment of Acne

A sixteen year old female was diagnosed with acne *vulgaris*. She had numerous red papules and pustules on her forehead. Various skin cleansing regimes and antibiotic (erythromycin and clindomycin) treatments had been tried and had failed to control the acne. Prior to bedtime, the papules and pustules on one side of her forehead were moistened and covered with a nanocrystalline silver coated high density polyethylene mesh, prepared as in Example 1 (single layer, blue coating). The mesh was then occluded with a thin film dressing which remained in place for 10 hours. Upon removal, the papules and pustules were no longer red and were only slightly raised. Some brown staining of the skin was observed.

Example 6

Treatment of Acne

A sixteen year old male was diagnosed with acne *vulgaris*. He had numerous raised, red papules and pustules on his forehead. Various skin cleansing regimes and antibiotic treatments had been tried and had failed to control the acne. The patient was placed on isotretinoin treatment which controlled his acne well. He did develop a single large pustule on his forehead which was embarrassing for him. Prior to bedtime, the pustule was moistened and covered with a nanocrystalline silver coated high density polyethylene mesh prepared as in Example 2. The mesh was then occluded with a thin film dressing which remained in place for 10 hours. Upon removal the pustule was no longer red and was only slightly raised. A second treatment resulted in the disappearance of the pustule.

Example 7

Treatment of Acne

A sixteen year old female was diagnosed with acne *vulgaris*. She had numerous red papules and pustules on her forehead. Various skin cleansing regimes and antibiotic (erythromycin and clindomycin) treatments had been tried and had failed to control the acne. Prior to bedtime, the papules and pustules on one side of her forehead were moistened and covered with a nanocrystalline silver coated high density polyethylene mesh, prepared as in Example 2. The mesh was then occluded with a thin film dressing which remained in place for 10 hours. Upon removal the papules and pustules were no longer red and were only slightly raised. A second treatment resulted in the disappearance of the papules and virtual elimination of the pustules. The silver coated mesh, when prepared as set forth in Example 2, did not result in any staining of the skin.

Example 8

Treatment of Adult Acne with Silver-Impregnated Hydrocolloid Dressing

A 49 year old white male experienced occasional acne *vulgaris*. He had painful, raised, red papules and pustules on his shoulders. The patient was treated with a thin hydrocolloid dressing (Craig Medical Products Ltd., Clay Gate House 46 Albert Rd. North Reigate, Surrey, United Kingdom) which was impregnated with 1% nanocrystalline silver powder formed with atomic disorder as in Example 3.

Following cleansing, the pustule was covered with a small disc of the dressing, which remained in place for 24 hours. Upon removal, the pustule was no longer painful, red, or raised.

Example 9

Treatment of Eczema

A twenty-nine year old white female presented with acrodermatitis. The erythematous area was located on the dorsal surface of the first web space of the left hand. It was bounded by the metacarpal bones of the thumb and index finger. The patient also complained of pruritus associated with the dermatitis. A gel consisting of 0.1% nanocrystalline silver powder (formed with atomic disorder as in Example 3) and 2% carboxyniethylcellulose was applied to the inflamed area before bedtime. There was an immediate antipruritic effect that provided the patient with relief in the short term. The next morning all evidence of acrodermatitis (i.e. redness disappeared) was gone. The condition had not returned after two weeks.

Example 10

Allergic Contact Dermatitis

Skin allergic contact hypersensitivity is caused by excessive infiltration of eosinophils. An animal model may be used for in vivo evaluation of eosinophil infiltration in the contact sensitivity reaction and to determine whether it is associated with allergic skin conditions such as contact dermatitis. On a gross histology level, this can be measured by the degree of erythema and edema at the dermatitis site. Current drugs used for treatment of this and other related eczema conditions include high potency steroids (Ultravate™), medium potency steroids (Elocon™) and non steroidal anti-inflammatory compounds (Protopic™ or tacrolimus). These compounds do not always work and may have undesirable side effects. Several commercially available anti-inflammatory products were compared to a nanocrystalline silver powder for the treatment of allergic contact dermatitis as follows.

Four healthy domestic pigs (approximate weight 20 kg) were used in the study. All pigs had normal skin prior to induction of eczema with 10% 2,4-dinitrochlorobenzene (DNCB) in acetone. The animals were housed in appropriate animal facilities with 12 hour light-dark cycles. The pigs were fed antibiotic-free feed and water ad libitum. The pigs were housed and cared for in accordance with Canadian Council of Animal Care guidelines. On day 0, the hair on both left and right back and side were clipped. The DNCB solution was painted over this area. This was repeated on day 7 and 11. On day 11, the solution was painted approximately 4 hours before treatment was initiated.

Treatment groups are shown in the following table. Protopic™ (tacrolimus), Elocon™ and Ultravate™ were purchased as creams from the local pharmacy. The nanocrystalline silver powder (1 g/L) was mixed into a 2% sodium carboxymethyl cellulose (CMC) and water solution at 30° C. using a magnetic stirrer at a high speed (Vista Scientific). Petrolatum, commercially known as Vaseline™, was used as a control for Elocon™ and Ultravate™.

| Pig # Treatment | Treatment (Left Side) | Control (Right Side) | Day of |
|---|---|---|---|
| 1 | Protopic™ (tacrolimus) | Protopic™ Control | Day 0 |
| 2 | Medium Potency Steroid (Elocon™) | Petrolatum | Day 0 |
| 3 | 2% CMC + 1% nanocrystalline silver (Vista Scientific) | 2% CMC | Day 0 |
| 4 | High Potency Steroid (Ultravate™) | Petrolatum | Day 0 |

Pigs were placed under general anesthetic with ketamine (Ketalean™, MTC Pharmaceuticals, Cambridge, ON; 4-500 mg) and halothane (MTC Pharmaceuticals). The skin was wiped with a moist gauze and allowed to dry. Bandages (n=8) containing each treatment were applied to the left side of the thoracolumbar area of the pig, while control bandages (n=8) were applied to the right side of the thoracolumbar area of the pig. Following placement of bandages, they were covered with Tegaderm™ (3M Corp., Minneapolis, Minn.) which was secured with an Elastoplast™ (Smith and Nephew, Lachine, QC) wrap. Bandages with active agents were changed daily. The skin associated with each bandage site was scored for severity of erythema (0=normal, 1=slight, 2=moderate, 3=severe, 4=very severe) and swelling (0=normal, 1=slight, 2=moderate, 3=severe, 4=very severe). This was performed on days 0, 1, 2 and 3.

Figure 3:
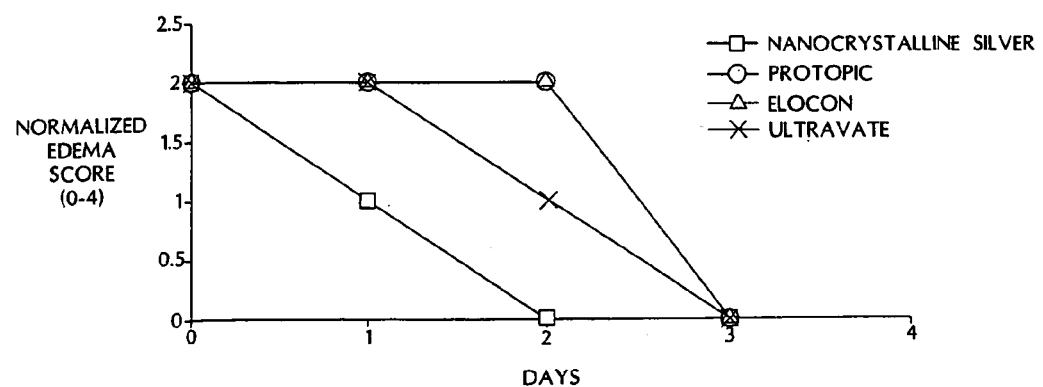
FIG. 3 is a graph showing the efficacy of different forms of silver on edema.
Figure 4:
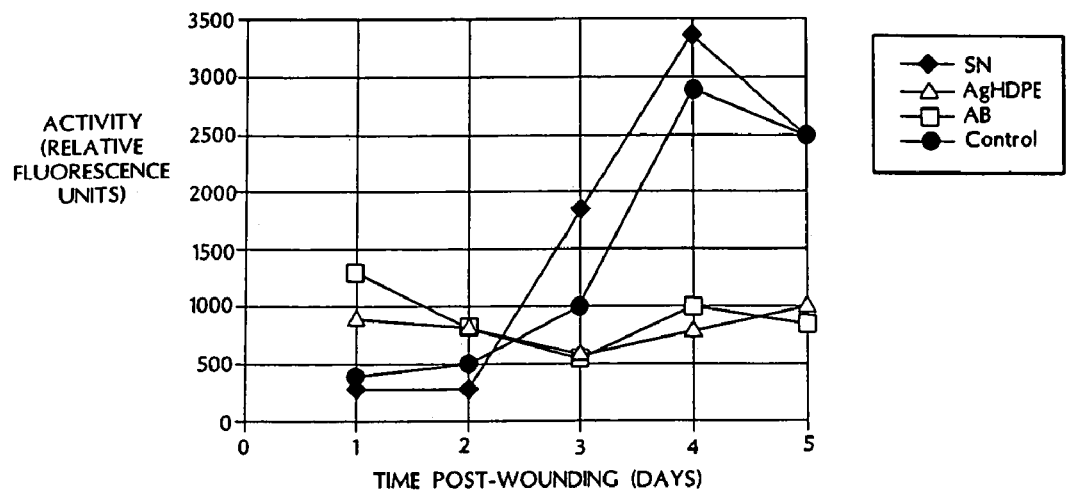
FIG. 4 is a graph showing MMP activity of incision fluids recovered from incisions dressed with materials.

All pigs remained healthy during the study. Results are shown in the following tables, and indicated in FIGS. 3 and 4. FIGS. 3 and 4 show the efficacy of the nanocrystalline silver powder compared to Protopic™, Elocon™ and Ultravate™ in the treatment of contact dermatitis in the pig model.

| | Day 0 | Day 1 | Day 2 | Day 3 |
|---|---|---|---|---|
| Treatment (Erythema) | | | | |
| Nanocrystalline silver | 3 | 2 | 1 | 0 |
| Protopic™ | 3 | 3 | 1.9 | 0.4 |
| Elocon™ | 3 | 2.4 | 2.6 | 2.6 |
| Ultravate™ | 3 | 3 | 3 | 3 |
| Treatment (Edema) | | | | |
| Nanocrystalline silver | 2 | 1 | 0 | 0 |
| Protopic™ | 2 | 2 | 2 | 0 |
| Elocon™ | 2 | 2 | 2 | 0 |
| Ultravate™ | 2 | 2 | 1 | 0 |

The pigs treated with the high (Ultravate™) and medium (Elocon™) strength steroids showed little to no improvement in the degree of erythema associated with contact dermatitis. They did, however, improve in terms of edema in that at Day 3, no swelling was apparent. Protopic™ showed a marked improvement when compared to the steroids in both the degree of erythema and edema. The largest improvement occurred with the nanocrystalline silver powder suspended in a 2% carboxymethyl cellulose gel. Both erythema and edema scores were lower after a single treatment and were normal after Day 2 (edema) and Day 3 (erythema) of treatment. Clearly the nanocrystalline silver product was more efficacious in treating contact dermatitis than the commercially available products.

Example 11

Preparation of Gels

No. 1

A commercial carboxymethyl cellulose/pectin gel (Duo-DERM™, ConvaTec Canada, 555, Dr. Frederik Philips, Suite 110, St-Laurent, Quebec, H4M 2X4) was combined with nanocrystalline silver powder prepared as set forth in Example 3 to produce a gel with 0.1% silver. A logarithmic reduction test was performed as follows in the gel using *Pseudomonas aeruginosa*. The inoculum was prepared by placing 1 bacteriologic loopful of the organism in 5 mL of trypticase soy broth and incubating it for 3-4 h. The inoculum (0.1 mL) was then added to 0.1 mL of gel and vortexed (triplicate samples). The mixture was incubated for one-half hour. Then 1.8 mL of sodium thioglycollate-saline (STS) solution was added to the test tube and vortexed. Serial dilutions were prepared on $10^{-1}$ to $10^{-7}$. A 0.1 mL aliquot of each dilution was plated in duplicate into Petri plates containing Mueller-Hinton agar. The plates were incubated for 48 h and then colonies were counted. Surviving members of organisms were determined and the logarithmic reduction compared to the initial inoculum was calculated. The logarithmic reduction for this mixture was 6.2, indicating a significant bactericidal effect.

No. 2

Carboxymethyl cellulose (CMC) fibers were coated directly to produce an atomic disordered nanocrystalline silver coating, using magnetron sputtering conditions similar to those set forth in Example 1. The CMC was then gelled in water by adding 2.9 g to 100 mL volume. This material was tested using the method of No. 1. The material generated a 5.2 logarithmic reduction of *Pseudomonas aeruginosa*, demonstrating that the gel had a significant bactericidal effect.

No. 3

An alginate fibrous substrate was directly coated with an atomic disordered nanocrystalline silver coating using magnetron sputtering conditions similar to those set forth in Example 1. The alginate (5.7 g) was added to 100 mL volume of water to create a gel. This material was tested using the method of No. 1. The material generated a 5.2 logarithmic reduction of *Pseudomonas aeruginosa*, demonstrating that the gel had a significant bactericidal effect.

No. 4

A commercial gel containing CMC and alginate (Purilin gel, Coloplast) was mixed with a atomic disordered nanocrystalline silver powder to give a product with 0.1% silver. This was tested as above with both *Pseudomonas aeruginosa* and *Staphylococcus aureus*. Zone of inhibition data was also generated for this gel as follows. An inoculum (*Pseudomonas aeruginosa* and *Staphylococcus aureus*) was prepared as in No. 1 and 0.1 mL of this was spread onto the surface of Mueller-Hinton agar in a Petri dish. A six mm hole was then cut into the agar at the center of the Petri dish and removed. The well was filled with either 0.1 mL of the silver containing gel, a mupirocin containing cream or a mupirocin containing ointment. The Petri plates were then incubated for 24 h and the diameter of the zone of inhibition was measured and recorded.

The silver containing gel produced 9 mm zone of inhibition against both *Pseudomonas aeruginosa* and *Staphylococcus aureus*, while the mupirocin cream and ointment produced 42 and 48 mm zones against *Staphylococcus aureus* and 0 mm zones against *Pseudomonas aeruginosa*.

The silver containing gel reduced the *Pseudomonas aeruginosa* and *Staphylococcus aureus* properties by 4.4 and 0.6 log reductions, respectively, showing good bactericidal activity. The mupirocin cream and ointment generated 0.4 and 0.8, and 0.8 and 1.6, log reductions against *Staphylococcus aureus* and *Pseudomonas aeruginosa*, respectively. The silver gel had both a greater bactericidal effect and spectrum of activity than the mupirocin containing products.

Nos. 5-10

The formula for Nos. 5-10 are summarized in the following table. Zones of inhibitions were determined as in No. 4 and log reductions were determined as in No. 1.

All formulae provided a broader spectrum of activity and a greater bactericidal effect than did mupirocin in a cream or ointment form. The mupirocin cream produced zones of inhibition of 42 and 0, and log reduction of 0.4 and 0.8, against *Staphylococcus aureus* and *Pseudomonas aeruginosa*, respectively.

| # | CMC (%) | PVA (%) | Ag Powder (%) | Beta-glucan | Methyl paraben | Propyl paraben | CZOI *S. aureus* | CZOI *P. aeruginosa* | Log red'n *S. aureus* | Log red'n *P. aeruginosa* |
|---|---|---|---|---|---|---|---|---|---|---|
| 5 | 2 |  | 0.1 |  |  |  | 11 | 13 | 1.4 | >6 |
| 6 | 2 | 0.5 | 0.1 |  | 0.1 | 0.02 | 14 | 15 | 3.3 | >6 |
| 7 | 2 | 0.5 | 0.1 |  |  |  | 13 | 14 | 2 | N/A |
| 8 | 2 | 0.5 | 0.1 |  | 0.1 |  | 14 | 14 | 2 | N/A |
| 9 | 2 | 0.5 | 0.1 |  |  | 0.20 | 14 | 14 | 2 | N/A |
| 10 | 2 | 0.5 | 0.1 | 0.5 | 0.1 | 0.20 | 14 | 14 | 2 | >6 |

No. 11

A commercially available gel (glyceryl polymethacrylate) was blended with nanocrystalline silver powder to produce a gel with a silver content of 0.1%. This gel was tested as in Nos. 5-10 and was found to produce zones of 15 mm against both *Staphylococcus aureus* and *Pseudomonas aeruginosa*. Log reductions of 1.7 and >5 were produced against *Staphylococcus aureus* and *Pseudomonas aeruginosa*. This gel product had a greater spectrum of activity than did mupirocin cream or ointment.

Example 12

Treatment of Adult Acne with Nanocrystalline Silver Gel Occluded by a Hydrocolloid Dressing A 49 year old white male experienced occasional acne vulgaris. He had painful, raised, red papules and pustules on his shoulders. The patient was treated with gel formulation No. 5 as set forth in Example 11. Gel formulation No. 5 was applied to the problem area of the patient's shoulders and then occluded by a thin hydrocolloid dressing (Craig Medical Products Ltd., Clay Gate House 46 Albert Rd. North Reigate, Surrey, United Kingdom). The dressing remained in place for 24 hours. Upon removal the pustule was no longer painful, red, or raised.

Treatment of Mucosal or Serosal Conditions

Example 1

Preparation of Nanocrystalline Silver Coatings on Dressings

This example shows the preparation of a bilayer nanocrystalline silver coating on a dressing material. A high density polyethylene dressing, DELNET™ or CONFORMANT 2™ was coated with a silver base layer and a silver/oxide top layer to generate a coloured antimicrobial coating having indicator value as described in Example 1 of the Treatment of Hyperproliferative Skin conditions examples. The coating layers were formed by magnetron sputtering under the conditions set out in the following table.

Example 2

Preparation of Atomic Disordered Nanocrystalline Silver Powders

Atomically disordered, nanocrystalline silver powder was prepared as described in Example 3 in the Treatment of Inflammatory Skin conditions examples above.

Example 3

Silver solutions were prepared by immersing AgHDPE mesh from dressings prepared as in Example 1 in reverse osmosis water that had been pretreated with $CO_2$ in order to reduce the pH. Two different concentrations of silver solutions were prepared by this method, the concentrations being 85 µg/ml, and 318 µg/ml. Solutions of silver nitrate were also prepared to use as comparisons in the experiments. The concentrations of the silver nitrate were 103 ppm of silver and 295 ppm of silver as determined by Atomic Absorption Spectroscopy.

The solutions were in turn placed in an ultrasonic nebulizer that created small droplets containing dissolved and suspended parts of the silver solution. The output from the nebulizer was directed into a chamber made from a stainless steel frame and base. Petri dishes containing Mueller Hinton agar streaked with 4 h old cultures of *Pseudomonas aeruginosa* and *Staphylococcus aureus*, were exposed to the silver solution aerosols and the silver nitrate aerosols.

The results of the tests show that silver aerosols of this invention transmit the antimicrobial activity of the dressings to remote sites, and such aerosols are more effective than comparable concentrations of silver nitrate.

In many instances the delivery of antimicrobial materials may most expeditiously be accomplished by using aerosols (e.g. treatment of pneumonia). The drawback of aerosols is the requirement for a high concentration of the active ingredient to ensure that a sufficient amount is delivered to achieve the biological effect desired without causing problems with the carrier solvent (e.g. water). It is preferably that the equipment for producing an aerosol that contains the dissolved and suspended components of nanocrystalline silver form droplets of aerosol direct from the liquid form, and the aerosol droplets must be small enough to reach the lungs. This means the droplets should be less than approximately 10 µm. To meet these requirements the aerosol is not created by first evaporating the liquid then condensing it to form droplets., Rather, aerosols are generated by 1) mechanical disruption of the liquid, or 2) air under pressure passing through some form of orifice that combines the air and the liquid in a way that creates droplets instead of evaporating the liquid.

Several experiments were carried out with silver solutions of this invention and silver nitrate solutions to determine if the antimicrobial activity of the dressing could be transferred through a direct droplet aerosol to a Petri dish.

a) Methods
  i) Equipment

The method used for the current tests was the mechanical method in the form of an ultrasonic nebulizer. For convenience an ultrasonic humidifier was used. The liquid containing the dissolved and suspended silver from the dressing of Example 1 was placed in the water reservoir of the humidifier. When power was applied to the humidifier aerosol droplets of dissolved and suspended silver were generated and flowed from the output nozzle.

A test chamber was constructed using a stainless steel frame with a transparent plastic covering. The frame was placed on a stainless steel base plate. The output nozzle from the humidifier was modified so that the aerosol could be directed into the chamber at a height of approximately 30 cm from the base. The plates and other test samples were placed on the stainless steel plate and exposed to the aerosol for a prescribed length of time.

ii) Solutions

Solution 1—A silver containing solution was prepared by immersing 518 sq. inches of the dressing from Example 1 in 1 L of reverse osmosis water, which was treated with $CO_2$ to maintain a pH of 6.5. After 20 minutes the concentration of silver in the water was 85 µg/ml.

Solution 2—A solution containing 370 µg/ml of silver from a dressing from Example 1 was prepared as follows: 1 L of reverse osmosis water was purged with commercial grade carbon dioxide until the pH was 4.3.

Sufficient dressing was added to bring the pH up to 6.5. At that time, the silver concentration was 370 µg/ml.

Solution 3—Ag as $AgNO_3$ was prepared by dissolving 0.157 g of $AgNO_3$ into 1 L of reverse osmosis water and mixed until dissolved. The solution was analyzed by Atomic Absorption Spectroscopy and found to be 102.9 ppm of silver.

Solution 4—Ag as $AgNO_3$ was prepared by dissolving 0.427 g of $AgNO_3$ into 1 L of reverse osmosis water and mixed until dissolved. The solution was analyzed by Atomic Absorption Spectroscopy and found to be 295 ppm of silver.

iii) Aerosolization

Petri dishes, containing Mueller Hinton agar, were streaked with 4 h old cultures of *Pseudomonas aeruginosa* or *Staphylococcus aureus*. The plates were then weighed and their exposed outer surfaces were coated with Parafilm to prevent condensation from occurring on these surfaces. These plates were placed in the aerosol chamber uncovered. The ultrasonic nebulizer was then started and run for 53 minutes. The plates were then removed from the chamber, the plastic was removed and the dishes re-weighed so that the amount of moisture loss/gain could be determined.

The plates were then placed in a 35° C. incubator for 16 h. After incubation the pattern and amount of growth was assessed on the plates for both organisms.

iv) Viability Assessment

Three of the six plates made for each organism were tested to determine if the antimicrobial effect was cidal or static in nature. This was accomplished by rinsing or placing a piece of the clear section of agar in the Petri dish plates into Tryptic soy broth in a test tube and incubating for 4 h or 16 h. If the medium turned turbid in 4 h it would indicate that the antimicrobial affect was bacteriostatic in nature. If the organisms took more than 16 h to grow, as indicated by turbidity, it was considered an indication that both static and cidal effects occurred. If no growth occurred the effect was bactericidal.

v) Results—The results are summarized in the following table.

|  | Silver from Dressing | | AgNO$_3$ | |
| --- | --- | --- | --- | --- |
| Organism | P. aeruginosa | S. aureus | P. aeruginosa | S. aureus |
| Solutions 1 and 3 | | | | |
| Ag concentration (µg/ml) | 85 | 85 | 99 | 99 |
| pH of test solution | 6.5 | 6.5 | About 6.5 | about 6.5 |
| Exposure Time (minutes) | 53 | 53 | 53 | 53 |
| Exposed are (sq. in.) | 9.8 | 9.8 | 9.8 | 9.8 |
| Exp Weight Gain (g) | 0.8 | 0.8 | 1.05 | 1.05 |
| Growth at 16 h | 0 | 0 | 0 | 0 |
| (0-++++) at 48 h | 0 | ++ | 0 | ++++ |
| Viable | | | | |
| 4 h | No | No | No | No |
| 16 h | No | No | No | N/A |
| Solutions 2 and 4 | | | | |
| Ag concentration (µg/ml) | 370 | 370 | 300 | 300 |
| pH of test solution | 6.5 | 6.5 | About 6.3 | about 6.3 |
| Exposure Time (minutes) | 53 | 53 | 53 | 53 |
| Exposed are (sq. in.) | 9.8 | 9.8 | 9.8 | 9.8 |
| Exp Weight Gain (g) | 1.14 | 1.14 | 1.12 | 1.12 |
| Growth at 16 h | 0 | 0 | 0 | 0 |
| (0-++++) at 48 h | 0 | 0 | 0 | +++ |
| Viable | | | | |
| 4 h | No | No | No | No |
| 16 h | No | No | No | N/A | vi) Discussion

At the low concentration of silver in solution, the dressing generated silver was effective in controlling the growth of both organisms while the silver nitrate only prevented the growth of P. aeruginosa. Viability tests showed that at the low concentration, neither form of silver was completely bacteriocidal although the poor growth on the dressing aerosol treated plates compared to the silver nitrate treated plates suggests that a significant log reduction occurred in the dressing aerosol treated plates.

At a higher concentration of silver, both dressing generated silver (370 µg/ml) and AgNO$_3$ (300 µg/ml) were effective at controlling P. aeruginosa. Since no re-growth occurred, it is assumed that the agent at this concentration were bactericidal. Silver generated from the dressing was more effective than AgNO$_3$ at controlling S. aureus. No re-growth occurred on any plates or in the broth indicating a total kill of the organism while in the AgNO$_3$ treatment, a large number of organisms grew at 16 h.

Based on weight gain during aerosol treatments a dose per unit area can be calculated. In each case for solution 1 the dose was 8.5 µg/sq. inch while for solution 2 the dose was 38 µg/sq. inch. These doses, on a per lung basis, would be less than 10 mg of silver per hour of treatment. Each hour of treatment with dressing generated silver aerosols appears to provide at least 48 h of protection. Therefore the dose per day, from the high concentration treatment, would be about 5 mg or a little less than the silver released by 2 sq. inches of SSD per day.

A most significant advantage of using dressing generated silver may be the lack of a toxic cation such as NO$_3$ or sulfadiazine.

Overall, the example demonstrated that the dressing generated aerosols are operative to transmit the antimicrobial activity of the dressings to remote sites. Furthermore, the dressing generated aerosols were more effective than comparable concentrations of silver nitrate.

Example 4

Aerosolized Silver Solutions in Rats a) Materials And Methods i) Solutions From Atomically Disordered Silver Dressings A solution was prepared by sparging CO$_2$ through 400 ml of reverse osmosis water for 30 minutes at a flow rate of 1 L/min. The beaker of water was covered with a piece of parafilm to assist in maintaining a saturated CO$_2$ environment. This process resulted in the pH of the water dropping to about 4. At this point, approximately 600 square inches of silver-coated net (AgHDPE) prepared as in Example 1 was added to the water and stirred for approximately 40 minutes resulting in an elevation of the pH to approximately 6.5. The solution was then transferred to a medical nebulizer and connected to an oxygen cylinder with a flow rate of 10 L/min. The outflow of the nebulizer was connected to a sealed animal chamber housing the rats to be dosed. Only the "test" rats (15 randomly assigned animals) received the dosing. The rats received two, one-hour aerosol administrations of the solution on the day of infection. Thereafter, the test rats were dosed three times per day for an additional three days.

ii) Animals

Thirty male Sprague-Dawley rats were obtained from the University of Calgary, Alberta, Canada breeding colony. These animals were specific-pathogen free and weighed approximately 300 g. The animals were housed in groups of 5 in plastic cages with wire mesh tops. The rats had access to fresh water and rat chow ad libitum. All animals were maintained in an appropriate facility with 12-hour light/dark cycles and constant temperature and humidity, according to facility standard operating procedures. The protocol was approved by the University of Calgary Animal Care Committee and was conducted in accordance with guidelines established by the Canadian Council on Animal Care.

iii) Bacteria

The bacteria used for infection of these animals were Pseudomonas aeruginosa strain 579. The dose was previously titrated to ascertain that a dose of up to $10^{10}$ CFU was not lethal for the animals. The bacteria were grown overnight in Tryptic soy broth, washed once in sterile PBS, and re-suspended in a $\frac{1}{10}$ volume of sterile PBS.

iv) Infection

The rats were anesthetized by inhalation of 2% halothane. A 50 microliter volume of bacterial suspension was intratracheally administered into the bronchi of each rat. This was performed non-surgically on intubated animals. The infection process resulted in the instillation of approximately $2\times10^9$ CFU into the lungs of each animal.

v) Sampling

On each day, a number of animals were sacrificed. The lungs of the animals were aseptically removed, homogenized, and plated to determine bacterial levels. A few animals were also subjected to bronchoalveolar lavage prior to removal of the lungs. In several cases, lung homogenates and/or lavage fluids were reserved for silver analysis.

After the first batch of the silver solution was prepared, total silver analysis indicated that there was about 225 ppm of total silver in the solution. The solution was reserved for several hours until after next dosing of the animals. A second silver analysis indicated that the total silver in solution had dropped to about 166 ppm. The reason for the drop was immediately apparent as the silver had visibly precipitated out of solution and had deposited on the surface of the nebulizer. One other batch of freshly prepared solution had a total silver concentration of 337 ppm. Regardless of the actual numbers, the process of generating the silver solution results in a significant quantity of silver in the solution that is aerosolized into the dosing chamber.

The dosing chamber is not perfect. Although significant amounts of mist are generated into the chamber, the rates tend to lie on top of one another and are probably exposed to vastly different levels of the silver mist.

vi) Results i) Pulmonary Bacterial Levels

| Day | Log CFU/ Test Lung | Log CFU/ Control Lung |
|---|---|---|
| 1 | 6.2 | 7.3 |
| 2 | 4.1 | 7.8 |
| 3 | 0 | 6.2 |
| 4 | 3.5 | 4.8 |

The bacteriological results gathered from the lungs of the treated and control animals demonstrated a sharper decline in the numbers of bacteria present in the lungs following treatment with silver mist as compared to controls. The results indicated that, in spite of the small sample sizes and inconsistent exposures, a difference could still be noted. There was considerable variation in the numbers of bacteria recovered from individual animals within each treatment group and, therefore, there was no significant difference in the results. Gross examination of excised lungs suggested that there may have been less apparent damage to the lungs in the animals treated with the silver mist as compared to the untreated, infected animal. This was very encouraging given the potential anti-inflammatory effects of the nanocrystalline silver technology.

ii) Pulmonary Silver Levels

| Sacrifice Date | Rat Description | Total Silver Level | Average |
|---|---|---|---|
| 36999 | Silver mist 1 | 0.50 ppm | |
| 36999 | Silver mist 2 | 1.13 ppm | 0.74 ppm |
| 36999 | Silver mist 3 | 0.58 ppm | |
| 37000 | Silver mist 4 | 0.73 ppm | |
| 37000 | Silver mist 5 | 0.70 ppm | 0.72 ppm |
| 37000 | Control 1 | 0.08 ppm | |
| 37000 | Control 2 | 0.10 ppm | 0.09 ppm |

The results of the silver analysis appear to indicate that the amount of silver in the lung either plateaus or each dose of silver mist deposits a certain amount of silver within the lung and this level is significantly diminished prior to the next dosing of the animals.

The results of this experiment indicated that the method employed to prepare the silver mist solution was reasonably reproducible and yielded relatively high concentrations of silver in solution. However, the silver was prone to precipitation and should be freshly prepared prior to each dosing period. A lengthy period between preparation and dosing, although resulting in a decrease in the amount of silver in solution, did not result in a complete elimination of the silver from the solution or even result in the silver concentration dropping to very low levels.

The method employed for exposing the rats to the mist is also prone to significant variation due to the piling up of the rats and the resultant inconsistent exposure to the silver-containing mist. However, the silver analyses suggested that a reasonably uniform dose of silver was achieved when only a few animals were present within the dosing chamber.

Regardless of the difficulties associated with the experiment, the results were indicative of a therapeutic modality for pulmonary infections. The results showed that the presence of silver mist was effective in more rapidly clearing the bacterial load of the infected lungs than is the host immune system alone. The apparently less severe pathology associated with the rat lungs treated with the silver mist showed that the treatment was effective for more than simply assisting in the killing of invading organisms.

Example 5

Pulmonary Anti-inflammatory Activity

A solution form nanocrystalline silver coated dressings (AgHDPE) from Example 1 was prepared by sparging $CO_2$ through 1000 ml of reverse osmosis water using commercial $CO_2$ Soda Syphon Charger. This process resulted in the pH of the water dropping to about 4. At this point, approximately 333 ml of the carbonated water was decanted into a plastic bottle and 333 square inches of nanocrystalline silver-coated net was added to the water. The nanocrystalline silver-coated net and water were placed in 37° C. shaker incubator and shaken at 180 RPM for 30 minutes to elevate the pH to approximately 5.8. The solution was then transferred to a beaker and stirred vigorously for 2 minutes to raise the pH to approximately at 7.3. The dissolution solution was transferred to a commercial nebulizer which was connected to a medical air cylinder with a flow rate of approx. 20 L/min. The outflow of the nebulizer was connected to a animal chamber housing the rats to be dosed. Only the "test" rats (12 randomly assigned animals) received the dosing. The rats received two—½ hour aerosol administrations of the test solution on the day of infection. Thereafter, the test rats were dosed 3 times per day for an additional one and a half days.

Thirty male Spragu-Dawley rats were obtained. These animals are specific-pathogen free and weighed approximately 400 g. The animals are housed in groups of four in plastic cages with wire mesh tops. The rats had access to fresh water and rat chow ad libitum. All animals were maintained in an appropriate facility standard operating procedures.

The bacteria used for infection of these animals were *Pseudomonas aeruginosa* strain 5588. The dose was previously titrated to ascertain that a dose of up to $10^9$ CFU was not lethal for the animals. The bacteria were grown overnight in Tryptic soy broth, washed once in sterile PBS and resuspend in sterile PBS. The final concentration of the inoculum was $4 \times 10^9$ CFU/ml.

The rats were anesthetized by inhalation of 2% halothane. A 400 microliter volume of bacterial suspension was intratracheally administered in the bronchi of each rat. This was performed non-surgically on intubated animals. The infection process resulted in the instillation of approximately $10^9$ CFU into the lungs of each animal.

The three treatment groups of rats and treatment schedules were as follows:

| | |
|---|---|
| Group 1 | Infected, not treated (12 Rats) |
| Group 2 | Infected, animal will be treated by intramuscularly injection of Tobramycin at 30 mg/kg (12 mg/rat) once daily (12 Rats) |
| Group 3 | Infected and treated, using nanocrystalline silver solution and nebulizer (Nebulized Ag), three times a day (12 Rats) |
| Day One | |
| 10:00 AM | Infection |
| 4:00 PM | First treatment (For Group 2, Nebulized Ag for Group 3) |
| 8:00 PM | Nebulized Ag treatment for Group 3 |
| Day Two | |
| 9:00 AM | Injection treatment for Group 2, Nebulized Ag for Group 3 |
| 1:00 PM | Sacrifice and sample six Rats in each group |
| 3:00 PM | Nebulized Ag treatment for Group 3 |
| 8:00 PM | Nebulized Ag treatment for Group 3 |
| Day Three | |
| 9:00 AM | Injection treatment for Group 2, Nebulized Ag for Group 3 |
| 1:00 PM | Sacrifice and sample six Rats in each group |

On each day, six rats of each group of animals were sacrificed. The lungs of the animals were aseptically removed, homogenized and plated to determine bacterial levels. Lung samples were collected for histological examination. Three lung homogenates were reserved for silver analysis. Lungs were grossly scored (absent=0, mild=1, moderate=2, and severe=3) based on the degree and involvement of consolidation, hemorrhage, edema and necrosis based upon gross observation.

Histopathology was scored (0-4) based upon the degree of consolidation and inflammation (neutrophil infiltration). The entire right middle lobes of all rats were collected for histopathology. As whole lobes were selected there was no bias toward any sample. All samples were fixed in neutral buffered formalin at the time the lung was removed from the thorax. It was fixed overnight, dehydrated and embedded in was. Sections were obtained which were hydrated and stained with haematoxylin and eosin.

All sections were examined by a veterinary pathologist who was blinded to the treatment groups, until after the samples were scored and comments were provided. The Scores and comments are provided in Table 5. (0=normal, 1=slight, 2 moderate, 3 severe, 4 very severe).

Tissue Colony Counts:

At 24 hours, there was not a significant reduction in the number of colony forming units (cfu) in the nebulized Ag group compared to the control but at 48 hours there was a significant reduction in the bacterial numbers in the nebulized Ag animals. The Tobramycin treated animals had a similar cfu counts to the controls at time 24 hours and 48 hours.

| | Control | Tobramycin | Nebulization |
|---|---|---|---|
| 24 h animal | | | |
| 1 | 0 | 2 | 1 |
| 2 | 0 | 3 | 1 |
| 3 | 3 | 1 | 0 |
| 4 | 3 | 3 | 0 |
| 5 | 2 | 2 | 3 |
| 6 | 3 | 2 | 1 |
| 48 h animal | | | |
| 7 | 2 | 1 | 1 |
| 8 | 1 | 2 | 1 |
| 9 | 1 | 1 | 0 |
| 10 | 1 | 1 | 0 |
| 11 | 3 | 1 | 1 |
| 12 | Dead | Dead | Dead |

Histopathology of Lung Samples:

Both the control and the Tobramycin treated rats had similar pathology. These are outlined in Table 6. At 24 and 48 hours severe infiltration of polymorphonuclear leukocytes (PMN's) into the interstitial spaces of the lung was observed. These cellular elements could also be identified in alveolar and bronchiolar spaces but to a lesser extent. The pulmonary vessels were dilated and the alveolar spaces were filled with proteinaceous material. The silver-nebulized rats had occasional infiltration of PMN's and no evidence of accumulation of fluids in alveolar or bronchiolar spaces.

Histopathology of Lung Samples Removed from Rats

| Treatment | Time | Inflam Score | Consol Score | Comments |
|---|---|---|---|---|
| Control (1) | 24 | 3 | 3 | Severe infiltration of PMN into interstitial spaces. Proteinaceous secretion in alveolar spaces. Occasional PMN in alveolar and bronchiolar space. Consolidation in affected areas. Involvement of 70% of sample. Interstitial Pneumonia. |

-continued

Histopathology of Lung Samples Removed from Rats

| Treatment | Time | Inflam Score | Consol Score | Comments |
|---|---|---|---|---|
| Control (2) | 24 | 3 | 3 | Severe infiltration of PMNs into interstitial spaces. Proteinaceous secretion in alveolar spaces. Occasional PMN in alveolar and bronchiolar space. Consolidation in affected areas. Involvement of 80% of sample. Interstitial Pneumonia |
| Tobramycin (1) | 24 | 3 | 3 | Severe infiltration of PMNs into interstitial spaces. Proteinaceous secretion in alveolar spaces. Occasional PMN in alveolar and bronchiolar space. Consolidation in affected areas. Involvement of 90% of sample. Interstitial Pneumonia. |
| Tobramycin (2) | 24 | 3 | 3 | Severe infiltration of PMNs into interstitial spaces. Proteinaceous secretion in alveolar spaces. Occasional PMN in alveolar and bronchiolar space. Consolidation in affected areas. Involvement of 80% of sample. Interstitial Pneumonia. |
| Nebulized Ag (1) | 24 | 0 | 1 | No PMNs in area. Slight consolidation. Normal Lung |
| Nebulized Ag (2) | 24 | 1 | 1 | Slight infiltration of PMNs around vessels and brocheoli. |
| Control (1) | 48 | 3 | 3 | Severe infiltration of PMNs into interstitial spaces. Proteinaceous secretion in alveolar spaces. Occasional PMN in alveolar and bronchiolar space. Consolidation in affected areas. Involvement of 80% of sample. Interstitial Pneumonia. |
| Control (2) | 48 | 2 | 2 | Severe infiltration of PMNs into interstitial spaces. Proteinaceous secretion in alveolar spaces. Occasional PMN in alveolar and bronchiolar space. Consolidation in affected areas. Involvement of 60% of sample. Interstitial Pneumonia. |
| Tobramycin (1) | 48 | 3 | 3 | Severe infiltration of PMNs into interstitial spaces. Proteinaceous secretion in alveolar spaces. Occasional PMN in alveolar and bronchiolar space. Consolidation in affected areas. Involvement of 70% of sample. Interstitial Pneumonia. |
| Tobramycin (2) | 48 | 3 | 3 | Severe infiltration of PMNs into interstitial spaces. Proteinaceous secretion in alveolar spaces. Occasional PMN in alveolar and bronchiolar space. Consolidation in affected areas. Involvement of 70% of sample. Interstitial Pneumonia. Slight infiltration of PMNs around vessels and brocheoli. |
| Nebulized Ag (1) | 48 | 1 | 0 | Slight infiltration of PMNs around vessels and brocheoli. |
| Nebulized Ag (2) | | | | Normal lung. |

The nebulized nanocrystalline silver reduced bacterial colonization in Pseudomonas infected lungs reduced injury as determined by gross pathology (consolidation, hemorrhage, edema) in Pseudomonas infected lungs. Further, the nanocrystalline silver delivered by aerosol reduced pulmonary inflammation (primarily PMN infiltration) in Pseudomonas infected lungs compared to Tobramycin (IM).

Example 6

Pulmonary Anti-inflammatory Activity

A solution was prepared by sparging $CO_2$ through 1000 ml of reverse osmosis water using commercial $CO_2$ Soda Syphon Charger. This process results in the pH of the water dropping to about 4. At this point, approximately 333 ml of the carbonated water was decanted into a plastic bottle and 333 square inches of nanocrystalline silver-coated net was added to the water. The nanocrystalline silver-coated net and water were placed in 37° C. shaker incubator and shaken at 180 RPM for 30 minutes to elevate the pH to approximately 5.8. The solution was then transferred to a beaker and stirred vigorously for 2 minutes to raise the pH to approximately at 7.3. The solution had a final silver concentration of approximately 400 ppm.

Test solutions of silver nitrate (400 ppm) and silver acetate (400 ppm) were prepared by dissolving the silver salts in deionized water. A colloidal silver solution (20 ppm) in was obtained from a commercial source.

The dissolution solutions were transferred to commercial nebulizers which were connected to a Medical air cylinder with a flow rate of approx. 20 L/min. The outflows of the nebulizers were connected to an animal chamber housing the rats to be dosed. All rats (40 randomly assigned animals) received the dosing. The rats received two—½ hour aerosol administrations of the test solutions on the day of infection. Thereafter, the test rats were dosed 3 times per day for an additional one and a half days.

Forty male Sprague-Dawley rats were obtained. These animals are specific-pathogen free and weighed approximately 400 g. The animals were housed in groups of four in plastic cages with wire mesh tops. The rats had access to fresh water and rat chow ad libitum. All animals were maintained in an appropriate facility with 12-hour light/dark cycles and constant temperature and humidity, according to facility standard operating procedures.

The bacteria used for infection of 20 these animals were *Pseudomonas aeruginosa* strain 5588. The dose was previously titrated to ascertain that a dose of up to $10^9$ CFU was not lethal for the animals. The bacteria were grown overnight in Tryptic soy broth, washed once in sterile PBS and resuspend in sterile PBS. The final concentration of the inoculum was 4×10$^9$ CFU/ml.

The rats were anesthetized by inhalation of 2% halothane. A 400 microliter volume of bacterial suspension was intratracheally administered into the bronchi of each rat. This was performed non-surgically on intubated animals. The infection process resulted in the instillation of approximately 10$^9$ CFU into the lungs of each animal.

| | |
|---|---|
| Group 1 & 2: | Not infected and infected, treated with nebulized silver nitrate. (10 Rats) |
| Group 3 & 4: | Not infected and infected, treated with nebulized colloidal silver. (10 Rats) |
| Group 5 & 6: | Not infected and infected, treated with nebulized nanocrystalline silver. (10 Rats) |
| Group 7 & 8: | Not infected and infected, treated with nebulized silver acetate. (10 Rats) |

The treatment schedule was as follows:

| Day One | | Day Two | |
|---|---|---|---|
| 10:00 AM | Infection | 9:00 AM | Third Treatment |
| 4:00 PM | First Treatment | 1:00 PM | Sacrifice, sample 5 rats/Gp |
| 8:00 PM | Second Treatment | | |

All rats of each group of animals were sacrificed after 24 h. The lungs of the animals were aseptically removed, homogenized and plated to determine bacterial levels. Lung samples were collected for histological examination. Three lung homogenates were reserved for silver analysis. Lungs were grossly scored (absent=0, mild=1, moderate=2, and severe=3) based on the degree of involvement of consolidation, hemorrhage, edema and necrosis based upon gross observation.

Histopathology was scored (0-4) based upon the degree of consolidation and inflammation (neutrophil infiltration). The entire right middle lobes of all rats were collected for histopahtology. As whole lobes were selected there was no bias toward any sample. All samples were fixed in neutral buffered formalin at the time the lung was removed from the thorax. It was fixed overnight, dehydrated and embedded in wax. Sections were obtained which were hydrated and stained with haematoxylin and eosin.

All sections were examined by a veterinary pathologist who was blinded to the treatment groups, until after the samples were scored and comments were provided, with scoring being (0=normal, 1=slight, 2=moderate, 3=severe, 4=very severe).

All rats in the silver nitrate, silver acetate and colloidal silver groups had lung that were grossly scored as moderately to severely inflamed while the lungs of the nanocrystalline group were grossly scored as normal to slightly inflamed. This was confirmed by the histopathological analyses.

The nanocrystalline derived silver solution had pulmonary anti-inflammatory properties while the other forms of silver did not.

Example 7

Treatment of an Infected Throat with a Nanocrystalline Silver Derived Solution

A forty-nine year old male was suffering from an infected throat. The condition was accompanied by fever and a severe pain that made swallowing very difficult and limited the patients ability to sleep. A solution of nanocrystalline derived silver was prepared using a method similar to Example 1. This solution was gargled for one minute and repeated 3 times over the next ten minutes. Within an hour the pain was reduced to the point where the patient could sleep. The treatment was repeated every four hours for 16 h and then once 8 h later. The throat infection was cleared as determined by the elimination of fever and pain. No further symptoms occurred.

Example 8

Preparation of Gels

Gels were prepared as described above in Example 11 in the Treatment of Inflammatory Skin Conditions examples above.

Apoptosis Induction/MMP Modulation

Example 1

Preparation of Nanocrystalline Silver Coatings on Dressings

This example shows the preparation of a bilayer nanocrystalline silver coating on a dressing material. A high density polyethylene dressing, DELNET™ or CONFORMANT 2™ was coated with a silver base layer and a silver/oxide top layer to generate a coloured antimicrobial coating having indicator value as described in Example 1 of the Treatment of Hyperproliferative Skin conditions examples. The coating layers were formed by magnetron sputtering under the conditions set out in the following table.

Example 2

Preparation of Atomic Disordered Nanocrystalline Silver Powders

Atomically disordered, nanocrystalline silver powders were prepared as described in Example 3 in the Treatment of Inflammatory Skin Conditions examples above.

Example 3

Preparation of Gels

Gels were prepared as described above in Example 11 in the Treatment of Inflammatory Skin Conditions examples above.

Example 4

Effects of Antimicrobial Silver on Apoptosis and Matrix Metalloproteinases in a Porcine Model A porcine model was used to examine the effects of an antimicrobial metal formed with atomic disorder, preferably silver, on apoptosis and matrix metalloproteinases. Young, commercially produced, specific pathogen free domestic swine (20-25 kg) were used in these studies. The animals were conditioned in an animal facility for one week prior to any experimental manipulation. Typically, three animals were used in each experiment. The animals received water and hog ration (Unifeed™, Calgary, Alberta) without antibiotics ad libitum, were housed individually in suspended stainless steel cages (5'×6'), and maintained in a controlled environment with 12 hours of light per day. The study was approved by the University of Calgary Animal Care Committee and was conducted in accordance with guidelines established by the Canadian Council on Animal Care.

Antimicrobial silver metal was administered in the form of a dressing. The dressings included:

i) AB—nanocrystalline silver-coated dressing (the nonfoam, three-layer dressing as set out in Example 1), comprising two layers of silver-coated high density polyethylene (HDPE) bonded on either side of an absorbent rayon/polyester core;

ii) AgHDPE—nanocrystalline silver coated HDPE layers aseptically separated from the absorbent core of the AB dressings;

iii) Control—identical in construction to the AB dressing except that the HDPE was not coated with nanocrystalline silver;

iv) Gauze—the absorbent rayon/polyester core of the AB dressings;

v) cHDPE—the uncoated HDPE aseptically removed from the absorbent core of the control dressings; and vi) SN—sterile piece of the gauze dressing to which 24 μg silver/square inch (from silver nitrate) was added. This amount of silver is equivalent to the amount of silver released from a square inch of the AB dressing immersed in serum over a 24 hour period, as determined by atomic absorption analysis.

Dressings (i)-(iii) were gamma sterilized (25 kGy) prior to use. All dressings were moistened with sterile water prior to application to the incision. In some cases, the incisions were covered with a layer of occlusive polyurethane (Tegaderm™, 3M Corp., Minneapolis, Minn.).

Three isolates of bacteria were used in the inoculum, including *Pseudomonas aeruginosa, Fusobacterium* sp., and *coagulase*-negative *staphylococci* (CNS) (Culture Collection, University of Calgary, Calgary, Alberta). The bacterial strains were grown under appropriate conditions overnight prior to the day of surgery. On the morning of surgery, the organisms were washed with sterile water and resuspended to a final density of approximately $10^7$ CFU/mL. The bacteria were mixed together in a ratio of 1:0.5:1 (*Pseudomonas*:CNS:*Fusobacterium*) in water. Sufficient inoculum was prepared to wet the incision created in each experiment. This procedure resulted in the incisions initially being evenly contaminated with approximately $8 \times 10^4$ CFU/cm$^2$.

Prior to treatment, animals were sedated by an intramuscular injection of a mixture of 10 mg/kg ketamine (Ketalean™, MTC Pharmaceuticals, Cambridge, ON) and 0.2 mg/kg acepromazine (Atravet™, Ayerst Laboratories), followed by complete anesthesia induced by mask inhalation of 1-2% halothane (MTC Pharmaceuticals). Following induction of anesthesia, the dorsal and lateral thorax and abdomen of each animal was clipped using a #40 Osler blade and the skin subsequently scrubbed with a non-antibiotic soap, and allowed to dry prior to incision.

Animals typically received 20 full-thickness incisions, 10 on each side of the dorsal thorax. The incisions were created using a 2 cm diameter trephine. An epinephrine solution was then applied to the incisions to provide for complete hemostasis prior to inoculation. The incisions were contaminated by covering them with gauze sponges soaked with the bacterial inoculum. The wet sponges were covered with an occlusive barrier and allowed to stand for 15 minutes. In some instances, an incision was then sampled to determine the initial inoculum. Following any requisite sampling, the incisions were dressed with the appropriate dressings and covered with an occlusive layer that was secured with Elastoplast™ tape (Smith & Nephew, Lachine, QC). All animals received narcotic pain medication (Torbugesic™, Ayerst Laboratories, Montreal, QC, 0.2 mg/kg), as required.

The experimental and control groups are summarized in the following table:

| Animal # | Left Side (Silver Treatment) | Right Side (Controls) |
|---|---|---|
| Pig 1 | silver nitrate (SN) on gauze | gauze moistened with water |
| Pig 2 | AgHDPE | cHDPE |
| Pig 3 | AB | control |

A 2 cm diameter circle of the appropriate dressing was applied to each incision. For Pig 1, incisions on the left side were dressed with silver nitrate-moistened (SN) gauze, while control incisions on the right side received water-moistened gauze dressing. For Pig 2, the incisions on the left side were dressed with silver-coated HDPE (AgHDPE), while the control incisions on the right side received non-coated HDPE (cHDPE). For Pig 3, the incisions on the left side were dressed with AB dressing, while incisions on the right side received the vehicle control. For these experiments, each incision was individually covered with an occlusive film dressing (Tegaderm™, 3M Corp., Minneapolis, Minn.).

Each day following incision (up to 5 days), the dressing materials from each of the experimental and control groups were collected and pooled within each group. These dressing materials were then placed in conical centrifuge tube containing glass wool. The tubes and contents were centrifuged to remove all liquid from the dressings. The glass wool was then placed into a 5-mL syringe and pressed to recover the incision fluid from each of the six sample sets. The incisions were rebandaged in an identical manner to the original dressing format each time. Incision fluid which collected under the occlusive dressing was also aspirated and reserved for analysis. Due to the small volumes collected from each incision, it was necessary to pool the collected fluid from each of 10 incisions dressed with the same type of dressing. All incision fluids were stored at −80° C. until analysis.

Prior to enzyme zymography or activity assays, the protein concentrations of the incision fluid samples were compared to ensure that the protein levels in each sample were similar. The samples were diluted 1:100 in water and assayed using the BCA Protein Assay System™ (Pierce Chemical, Rockford, Ill.). A standard curve was concurrently constructed using dilutions of bovine serum albumin. Incision fluid was diluted in water and then mixed with an equal volume of sample buffer (0.06 M Tris-HCl, pH 6.8; 12% SDS; 10% glycerol; 0.005% bromophenol blue). The samples were then electrophoresed on 10% polyacrylamide (BioRad, Mississauga, ON) gels containing 0.1% gelatin. The proteins were then incubated in renaturing buffer (2.5% Triton™ X-100) for 90 minutes at 37° C. Following enzyme renaturation, the gels were incubated overnight in substrate buffer (50 mM Tri-HCl, pH 7.8; 5 mM $CaCl_2$; 200 mM NaCl; 0.02% Brij-35) with or without 10 mM 1,10 phenanthroline. The gels were subsequently stained with a standard Coomassie Blue stain and destained in methanol/acetic acid. Unless otherwise indicated, all chemicals were obtained from Sigma-Aldrich (Oakville, ON).

The incision fluid samples were assayed for the total amount of protein present. These values were between 30-80 mg/mL. The samples from individual animals were even more similar, varying by only 10-20 mg/mL in the pooled incision fluid.

i) Assay for Activity of Total MMPs

The total MMP activity of the incision fluid samples was determined by incubating diluted incision fluid with a quenched fluorescein-conjugated substrate (EnzChek DQ gelatin™, Molecular Probes, Eugene, Oreg.) for approximately 20 hours. Following incubation, the samples were read in a fluorometer (excitation 1=480 nm; emission 1=520 nm). Activity was compared to a collagenase standard as well as experimental versus control incision fluids.

FIG. 4 shows the change in total MMP activity from differently treated incision sites over a five-day period. The silver-coated HDPE (AgHDPE) results were essentially identical to those obtained using the silver-coated dressing (AB). Similarly, the gauze, non-coated HDPE (cHDPE), and control dressings yielded results essentially identical to each other and to untreated incisions under occlusion from which incision fluid was collected. Only the results from the control, silver-coated dressing (AB), silver-coated HDPE (AgHDPE), and silver nitrate moistened gauze (SN) are thus shown. The total MMP activity of the incision fluid sample from the control dressing was low for the first few days, then rose dramatically and remained high for the duration of the experiment. Similarly, the silver-nitrate moistened gauze (SN) demonstrated an almost identical pattern of total MMP activity. Results from the silver-coated dressing (AB) yielded dramatically different results. The level of MMP activity remained steady for the duration of the experiment and did not spike to high levels. Instead, it remained at a level roughly 60% lower than the highest level of activity reached in control or silver-nitrate moistened gauze (SN).

ii) Assay for Activity of Gelatinases

Gelatinases include MMP-2 (secreted by fibroblasts and a wide variety of other cell types) and MMP-9 (released by mononuclear phagocytes, neutrophils, corneal epithelial cells, tumor cells, cytotrophoblasts and keratinocytes). The gelatinases degrade gelatins (denatured collagens) and collagen type IV (basement membrane). Zymograms were run to examine changes in the levels and activity of MMP-9 and MMP-2 over the duration of the experiment.

Results of the zymograms for the control and silver nitrate moistened gauze (SN) appeared to be identical. The levels of MMP-9 declined over the period examined, particularly levels of the active form of MMP-9. The silver-coated dressing (AB) demonstrated higher levels of active MMP-9 than for the control. On Day 2, the silver-coated dressing (AB) showed lower levels of active MMP-9 than in the control. On Day 4, the silver-coated dressing (AB) showed little active MMP-9. In the control, the amount of the latent enzyme appeared to decrease while the active form of MMP-9 increased, particularly up to Day 4.

There was not much difference in the levels of MMP-2 activity for the silver-coated dressing (AB) over the duration of the experiment. However, there was an increase in the level of active MMP-2 in the control dressing by Day 5. It was also observed that the levels of some other, unidentified, gelatinolytic enzymes also decreased in the silver-coated dressing (AB) compared to the control.

iii) Assay of Total Protease Activity

Since MMPs have proteolytic activity, the total protease activity in incision fluid samples was assessed by incubating the samples with 3 mg/mL azocasein in 0.05 M Tris-HCl, pH 7.5 for 24 hours at 37° C. The undigested substrate was then precipitated by the addition of 20% trichloroacetic acid. The absorbance of the supernatant was then assessed using a spectrophotometer, 1=400 nm. The absorbance was compared to a standard curve prepared with bovine pancreatic trypsin.

Figure 5:
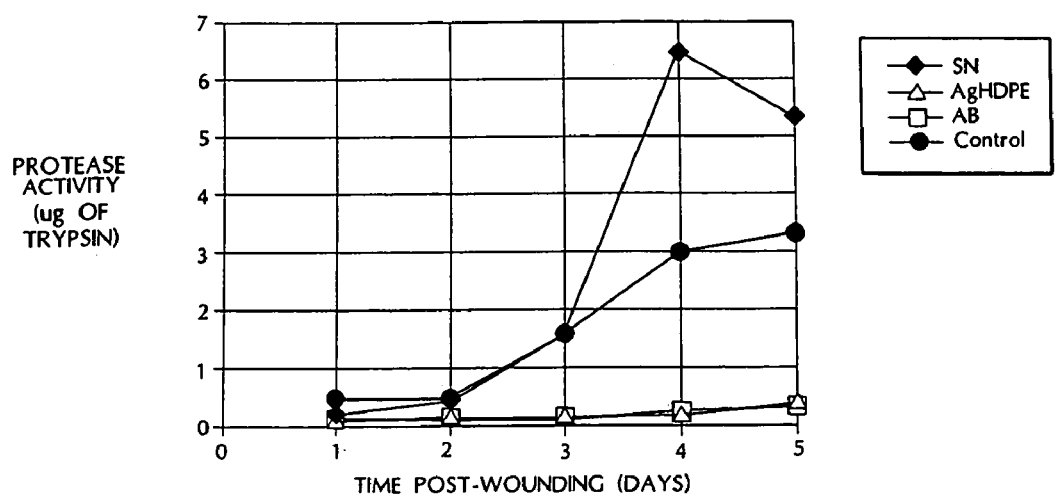
FIG. 5 is a graph showing total protease activity of incision fluids recovered from different dressings.

Results paralleled those obtained in the total MMP assay above. The incision fluid samples for the control and silver nitrate moistened gauze (SN) demonstrated a pronounced increase in activity after Day 2 (FIG. 5). Incision fluid from the silver nitrate moistened gauze (SN) also demonstrated a marked increase in the total protease activity compared to control dressing incision fluid (FIG. 4). However, the total protease activity in the incision fluids of the silver coated dressings (AB) remained constant over the duration of the experiment.

Antimicrobial silver was thus demonstrated to be effective in modulating overall MMP activity. However, silver nitrate was not effective in modulating MMP activity in spite of the $Ag^+$ concentration being approximately the same levels as were expected to be released from the silver-coated dressing (AB) over the same period of time (24 h) between applications. The reason for the difference in effects may be related to the inherent nature of the two silver formulations. In the case of silver nitrate, although the silver was added to provide a similar final concentration of $Ag^+$ as was anticipated to be released from the silver-coated dressing (AB), the $Ag^+$ ions were added at once. It would thus be expected that the serum proteins and chlorides within the incision fluid would quickly inactivate a large portion of the $Ag^+$. In the case of the silver-coated dressing (AB), the silver is continuously released to maintain a steady-state equilibrium, maintaining an effective level of silver in the incision for a prolonged period.

iv) Apoptosis

Histological assessment of cell apoptosis was carried out in order to determine whether the silver-coated dressing (AB) affected apoptosis within the incision.

Histological Observations of Porcine Tissue

Samples of tissue from the incisions were collected daily for the duration of the experiment, except for Day 1, and examined for evidence of apoptosis. The samples were fixed in 3.7% formaldehyde in PBS for 24 hours, then embedded in paraffin, and cut into 5 mm thick sections. The samples were then de-waxed with Clearing Solvent™ (Stephan's Scientific, Riverdale, N.J.) and rehydrated through an ethanol:water dilution series. The sections were treated with 20 mg/mL proteinase K (Qiagen, Germantown, Md.) in 10 mM Tris-HCl (pH 7.4) for 30 minutes at room temperature.

Terminal deoxynucleotidyl transferase nick end labeling (TUNEL staining) was performed using an In Situ Cell Death Detection POD Kit™ (Boehringer Mannheim, Indianapolis, Ind.). Using this technique, cells which stain brown are those being eliminated by apoptosis. Endogenous peroxidase was blocked with 3% hydrogen peroxide in methanol for 10 minutes at room temperature then cells were permeabilized with 0.1% Triton™ X-100 (in 0.1% sodium citrate) for 2 minutes on ice. After permeabilization, the samples were treated with the terminal transferase enzyme solution incubated in a humidified chamber at 37° C. for 60 minutes. Following labelling, the samples were washed once with 1.0% Triton™ X-100 and twice with PBS. The sections were incubated with Converter-POD™ (Boehringer Mannheim, Indianapolis, Ind.) in a humidified chamber at 37° C. for 30 minutes, and repeated washing with 1.0% Triton™ X-100 and PBS. Subsequently, the samples were incubated with DAB substrate (Vector Laboratory Inc., Burlingame, Calif.) for 10 minutes at room temperature and washed with 1.0% Triton™ X-100 and PBS. It was also necessary to counterstain the sections with hematoxylin nuclear counterstain (Vector Laboratory Inc., Burlingame, Calif.) for 10 seconds.

The prepared samples were then ready to be observed by light microscopy for evidence of apoptosis. For a positive control, the permeabilized sections were treated with 100 mg/mL DNase I in PBS for 10 minutes at room temperature to induce DNA strand breaks. For negative controls, the terminal transferase enzyme, POD or DAB were omitted between each labelling step.

In all samples examined, there was little difference between the control and silver nitrate moistened gauze (SN). However, significant apoptosis of the cell population was observed in incisions of the silver-coated dressing (AB). In the control incision, there were significant numbers of polymorphonuclear leukocytes (PMNs) and few fibroblasts, while in incisions of the silver-coated dressing (AB), there were significantly more fibroblasts and few PMNs.

Histopathological Scoring of Porcine Tissue

Animals were anesthetized as described above of Days 1, 4, and 7. A mid-incision biopsy was collected with a sterile 4 mm biopsy punch. The tissue was fixed in 10% neutral buffered formalin, embedded in methacrylate and sectioned (2-5 mm thick). The sections were stained with Lee's methylene blue and basic fuschin to demonstrate the cellular organization and bacteria. A pathologist blinded to the treatments scored the sections based on the presence of fibroblasts, PMNs and bacteria as follows: 0=absent; +=occasional with 1-5 per high power field of view; ++=moderate with 6-20 per high power field of view; +++=abundant with 21-50 per high power field of view; ++++=very abundant with more than 50 per high power field of view (see the following table).

| Day Post-Incision | Dressing | Fibroblasts | PMNs | Bacteria |
|---|---|---|---|---|
| 1 | Silver coated (AB) | ++ | ++ | + |
| 1 | Control | 0 | +++ | ++++ |
| 4 | Silver coated (AB) | ++++ | ++ | 0 |
| 4 | Control | + | ++++ | ++++ |
| 7 | Silver Coated (AB) | ++++ | + | 0 |
| 7 | Control | +++ | +++ | +++ |

The microscopic observation of the biopsy samples revealed that the infiltrating cell types were significantly different between the control and silver-coated dressings (AB). The control incisions were characterized by a large numbers of PMNs, while the silver-coated dressings (AB) demonstrated a larger proportion of fibroblasts and monocytes. The relative abundance of the fibroblasts in incisions of the silver-coated dressings (AB) became increasingly pronounced through to Day 7, as compared to the control incisions that remained populated largely by PMNs and monocytes. The staining method enabled staining also of bacteria, which was abundant in the control incision but generally absent in the incisions of the silver-coated dressings (AB).

Incisions treated with the nanocrystalline antimicrobial silver thus demonstrated more extensive apoptosis than did cells from incisions treated with either control or silver nitrate dressings. During the first two days following incision, the cell type which demonstrated the most pronounced increase in apoptosis were neutrophils. This suggests that part of the reason for the moderated neutrophil presence and the resultant modulation of MMP levels was due to neutrophil apoptosis. It has been shown that the number of apoptotic cells increases as the incision closes and that this is part of the mechanism involved in the decrease in cellularity of the maturing scar tissue (Desmouliere, A., Badid, C., Bochaton-Piallat, M. and Gabbiani, G. (1997) Apoptosis during wound healing, fibrocontractive diseases and vascular wall injury. Int. J. Biochem. Cell Biol. 29: 19-30.). The results suggest that the maturing of the nascent dermal and epidermal tissues may also be accelerated in the presence of the nanocrystalline antimicrobial metal-containing materials. The findings indicated that acceleration in healing induced by the nanocrystalline antimicrobial metal-containing materials is associated with a reduction of local MMP activity, as well as with an increased incidence of cell apoptosis within the incision.

Example 5

Clinical Study on the Effect of Silver-Coated Dressings on MMPs and Cytokines

This study was conducted to assess the effect of the silver-coated dressing on the concentrations of MMPs and cytokines in non-healing wounds over time during treatment. The modulation of the levels of active MMPs and cytokines may alleviate the inflammatory response in a wound, allowing the wound to advance through the subsequent stages of wound healing culminating in a healed wound.

A total of 10 patients with non-healing venous stasis ulcers were randomly assigned to treatment with a silver-coated dressing (5 patients) or a control dressing (5 patients). The silver-coated dressing was prepared as in Example 1. The control dressing was identical in construction to the silver-coated dressing of Example 1, except that the HDPE was not coated with silver. The ulcers were dressed in appropriate pressure dressings to correct the underlying medical problem. Samples of the ulcer fluid were collected before treatment (day 0) and at weekly intervals (days 1, 7, 14 and 21) by removing the silver-coated dressing or control dressing, and replacing the dressing with Tegaderm™ occlusive dressing (3M Corp., Minneapolis, Minn.) for one hour to allow wound fluids to collect. The fluid samples were aspirated from below the dressing in a syringe, and were frozen at −80° C. until assayed.

Assays were conducted for active MMP-9, active MMP-2, Tumor necrosis factor-α (TNF-α) and Interleukin-1β (IL-1β). High levels of MMP-9 and MMP-2 are predominant in non-healing wounds, with levels decreasing over time in normal healing wounds. Released by activated macrophages, TNF-α and IL-1β are indicators of wound inflammation. Levels of TNF-α and IL-1β are elevated in non-healing wounds and increase release of pro-MMPs, for example, MMP-9 and MMP-2.

To measure the levels of active MMP-9 and MMP-2, enzyme capture assays (BioTrak, NJ) were conducted. In this method, active enzyme is detected through activation of a modified pro-detection enzyme and the cleavage of its chromogenic peptide substrate. The resultant color is read by spectrophotometer, and the concentration of MMP is determined by interpolation of a standard curve, expressed in ng/ml (see results in FIGS. 6 and 7).

To assay the levels of cytokines, IL-1β levels were measured using a sandwich immunoassay (BioTrak, NJ), while TNF-α levels were measured by a high sensitivity sandwich antibody assay (BioTrak, NJ). In both methods, endogenous cytokine is bound to an immobilized antibody and then detected by an addition of a biotinylated antibody, followed by a colorimetric substrate. The color is measured by a spectrophotometer, and the concentrations of TNF-α and IL-1β are determined by interpolation of a standard curve and expressed as pg/ml (see results in FIGS. 8 and 9).

Total protein levels were measured for each sample to standardize the measures of the MMPs and cytokines. Total protein levels were measured using BCA Protein Assay System™ (Pierce Chemical, Rockford, Ill.). No protein level of any sample was significantly different from the total mean.

Figure 6:
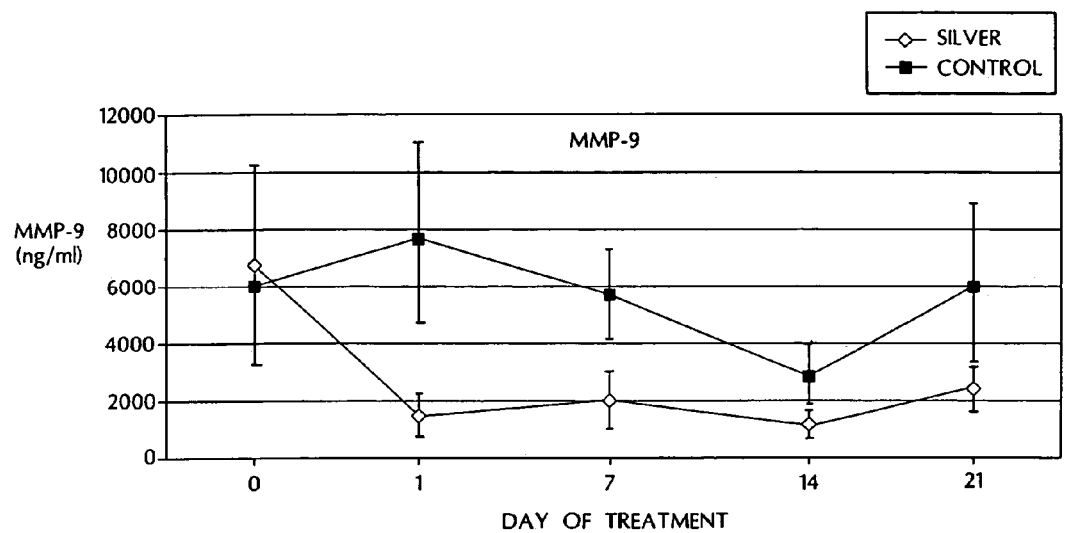
FIG. 6 is a graph showing the concentrations (ng/ml) of active MMP-9 in fluid samples recovered from ulcers dressed with different materials.

FIG. 6 is a graph showing the concentrations (ng/ml) of active MMP-9 in fluid samples recovered from ulcers dressed with silver-coated dressing (Silver) and control dressing (Control) at days 0, 1, 7, 14 and 21. The levels of active MMP-9 decreased to a normal level, and were suppressed over time with the silver-coated dressing compared to the control dressing, demonstrating a modulating effect of the silver-coated dressing.

Figure 7:
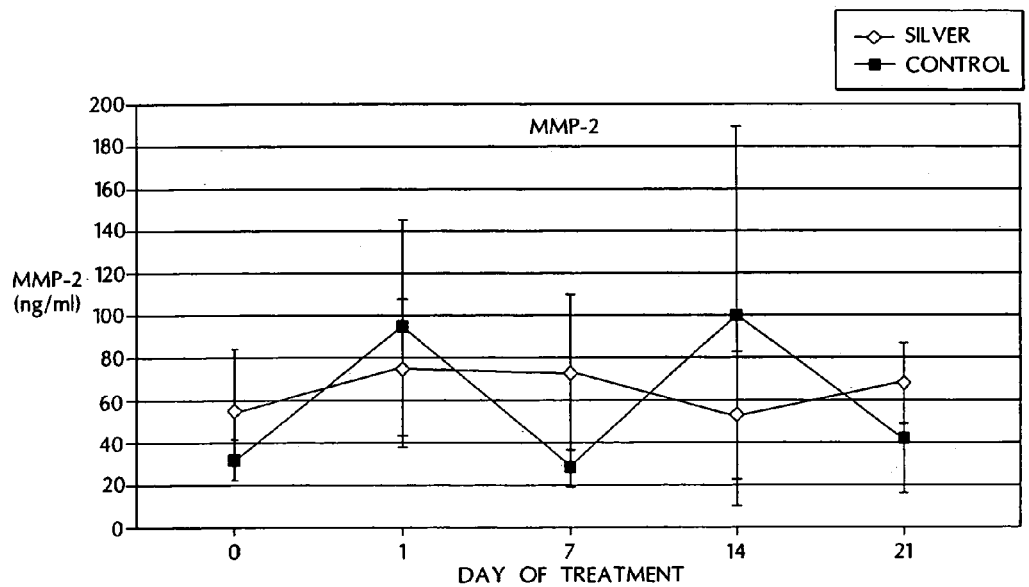
FIG. 7 is a graph showing the concentrations (ng/ml) of active MMP-2 in fluid samples recovered from ulcers dressed with different materials.

FIG. 7 is a graph showing the concentrations (ng/ml) of active MMP-2 in fluid samples recovered from ulcers dressed with silver-coated dressing (Silver) and control dressing (Control) at days 0, 1, 7, 14 and 21. The levels of active MMP-2 were not significantly different with the silver-coated dressing and the control dressing.

Figure 8:
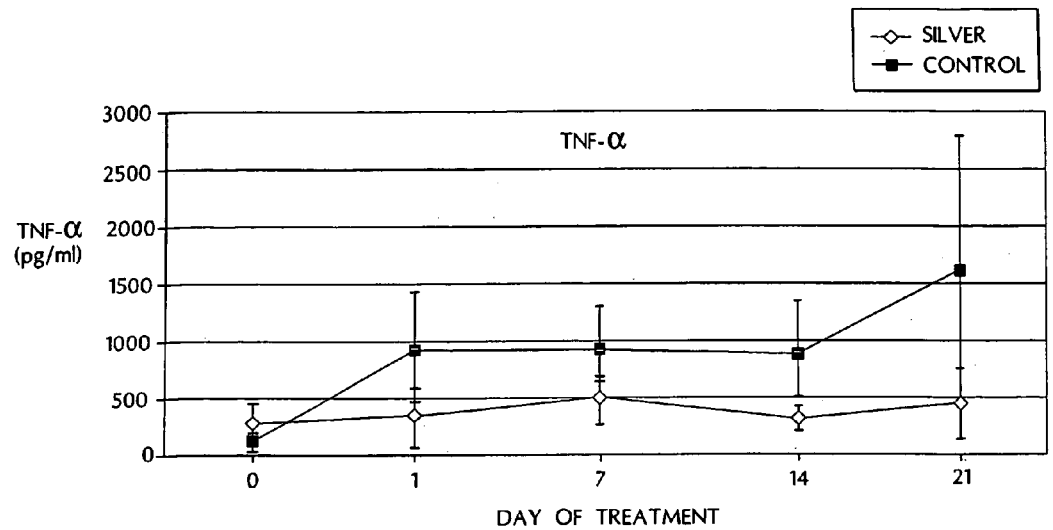
FIG. 8 is a graph showing the concentrations (pg/ml) of active TNF-α in fluid samples recovered from ulcers dressed with different materials.

FIG. 8 is a graph showing the concentrations (pg/ml) of TNF-α in fluid samples recovered from ulcers dressed with silver-coated dressing (Silver) and control dressing (Control) at days 0, 1, 7, 14 and 21. The levels of TNF-α were suppressed over the treatment period, and did not increase significantly over the treatment period with the silver-coated dressing, while the levels in the control dressing increased, demonstrating a modulating effect of the silver-coated dressing.

Figure 9:
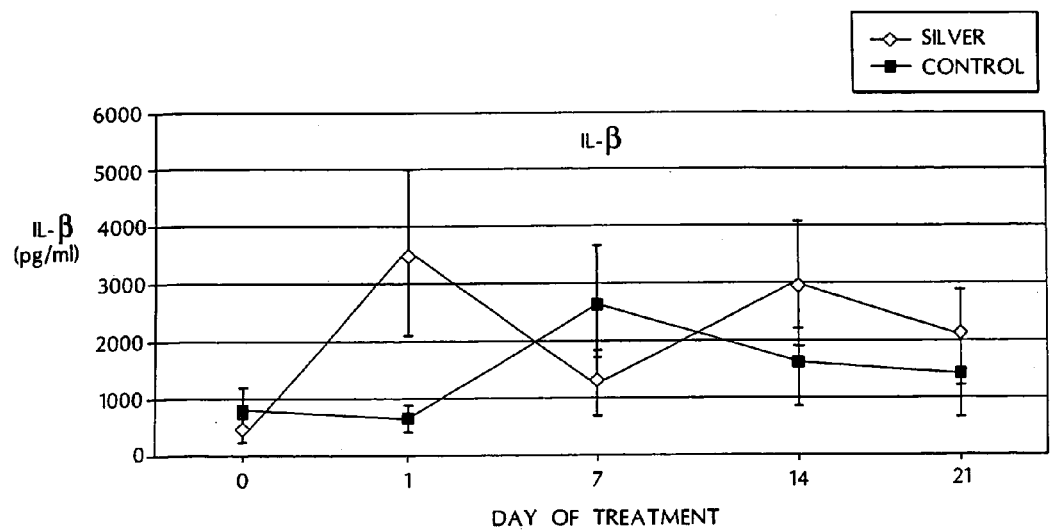
FIG. 9 is a graph showing the concentrations (pg/ml) of active IL-1β in fluid samples recovered from ulcers dressed with different materials.

FIG. 9 is a graph showing the concentrations (pg/ml) of IL-1β in fluid samples recovered from ulcers dressed with silver-coated dressing (Silver) and control dressing (Control) at days 0, 1, 7, 14 and 21. The levels of IL-1β were not significantly different with the silver-coated dressing and the control dressing.

The study suggests that the modulation of the MMP-9 and TNF-α levels is responsible for improved wound healing and reduced inflammation with silver-coated dressings. In comparison, the levels of MMPs and cytokines did not decrease over time with the control dressings.

This example and Example 4 above, taken together with the evidence that the silver materials herein disclosed are capable of reducing inflammation (see co-pending U.S. patent application Ser. Nos. 10/131,568; 10/131,511; 10/131,509; 10/131,513; and 10/128,208 filed Apr. 23, 2002; and co-pending U.S. patent application Ser. No. 09/840,637 filed Apr. 23, 2001, and U.S. Provisional Patent Application No. 60/285,884 filed Apr. 23, 2001) demonstrates a method of reducing inflammation in a patient in need thereof, by contacting an area of inflammation or an inflammatory cell with a therapeutically effective amount of the antimicrobial metal-containing materials in a crystalline form. The antimicrobial metal-containing materials are characterized by sufficient atomic disorder, such that the metal, in contact with an alcohol or water-based electrolyte, releases atoms, ions, molecules, or clusters of at least one antimicrobial metal at a concentration sufficient to modulate the release of one or both of MMP-9 and TNF-α. Excessive TNF production has been reported in diseases, such as cancer and autoimmune diseases, which are characterized by elevated MMP activity. In this regard, use of the nanocrystalline silver of the present invention, when in therapeutically effective amounts, provides the dual modulation of MMP-9 and TNF-α to alleviate the particular condition.

ADDITIONAL EXAMPLES

Example 1

6 milligrams of antimicrobial metal-containing material with atomic disorder, in free-standing powder form, are sprinkled lightly onto 6.5 cm$^2$ of burned tissue, and thereafter wet with a light spray of water or wound exudate or TDWL (Trans Dermal Water Loss) or other bodily fluids, so as to provide an antimicrobial treatment to the burned tissue. The treatment is repeated every 24 hours until the therapeutic effects are no longer needed.

Example 2

0.5 milligrams of antimicrobial metal-containing material with atomic disorder, in free-standing powder form, are injected, using a small-needle drug delivery system or a needle-less drug delivery system, into gum tissue so as to treat gingivitis. The treatment is repeated every 3 days until the therapeutic effects are no longer needed.

Example 3

A solution of antimicrobial metal-containing material with atomic disorder is prepared by dissolving 6 milligrams of antimicrobial metal-containing material with atomic disorder in 1 gram of water. The solution of antimicrobial metal-containing material with atomic disorder is applied as a rinse or bath or wash to a wound site so as to provide an antimicrobial treatment to the wound site. The treatment is repeated every 24 hours until the therapeutic effects are no longer needed.

Example 4

A solution of antimicrobial metal-containing material with atomic disorder is prepared by dissolving 6 milligrams of antimicrobial metal-containing material with atomic disorder in 1 gram of water. The solution of antimicrobial metal-containing material with atomic disorder is applied to the interior of the bladder via a catheter so as to provide antimicrobial treatment to the bladder. The treatment is repeated every 8 hours until the therapeutic effects are no longer needed.

Example 5

A solution of antimicrobial metal-containing material with atomic disorder is prepared by dissolving 6 milligrams of antimicrobial metal-containing material with atomic disorder in 1 gram of water. The solution of antimicrobial metal-containing material with atomic disorder is injected (using a small-needle or needle-less injection system) under the toenails or into the nail bed and/or the surrounding tissue of a person suffering from onychomycosis so as to provide an antimicrobial treatment to the tissue. The treatment is repeated 2 times a day until the therapeutic effects are no longer needed.

Example 6

Summary

Solutions of nanocrystalline noble metal-containing materials were prepared by immersing Acticoat® burn dressings (distributed by Smith & Nephew) in reverse osmosis water that had been pretreated with CO2 in order to reduce the pH. Two different concentrations of antimicrobial metal-containing material with atomic disorder solutions were prepared by this method, the concentrations being 85 mg/mL and 318 mg/mL. Solutions of silver nitrate were also prepared to use as comparisons in the experiments. The concentrations of the silver nitrate were 103 ppm of silver and 295 ppm of silver as determined by Atomic Absorption Spectroscopy.

The solutions were in turn placed in an ultrasonic nebulizer that created small droplets containing dissolved and suspended parts of the solution of nanocrystalline noble metal-containing material. The output from the nebulizer was directed into a chamber made from a stainless steel frame and base. Petri dishes containing Mueller Hinton agar streaked with 4 h old cultures of *Pseudomonas aerugiona* and *Staphylococcus aureus* were exposed to nanocrystalline noble metal aerosols and the silver nitrate aerosols.

The results of the tests show that nanocrystalline noble metal aerosols transmit the antimicrobial activity of the dressings to remote sites, and nanocrystalline noble metal aerosols are more effective than comparable concentrations of silver nitrate.

Introduction

In many instances the delivery of antimicrobial materials may most expeditiously be accomplished by using aerosols (e.g., in the treatment of pneumonia). The drawback of aerosols is the requirement for a high concentration of the active ingredient to ensure that a sufficient amount is delivered to achieve the biological effect desired without causing problems with the carrier solvent (e.g., water). The essential requirement of the equipment for producing an aerosol that contains dissolved and suspended components of antimicrobial metal-containing material with atomic disorder is that it must form droplets of aerosol directly from the liquid form, and the aerosol droplets must be small enough to reach the lungs. This means that the droplets should be preferably less than approximately 10 mm. To meet these requirements, the aerosol cannot be created by first evaporating the liquid and then condensing it to form droplets, since this would remove the desired antimicrobial metal-containing material with atomic disorder from the aerosol. There are two methods that can be used to relatively easily form the droplets directly: (1) mechanical disruption of the liquid; and (2) air, under pressure, passing through some form of orifice that combines the air and the liquid in a way that creates droplets instead of evaporating the liquid.

Several experiments were carried out with antimicrobial metal-containing material with atomic disorder and silver nitrate solutions to determine if the antimicrobial activity of the dressing could be transferred through a direct droplet aerosol to a Petri dish.

Equipment

The method used to create an aerosol for these tests was the mechanical method in the form of an ultrasonic nebulizer. For convenience, an ultrasonic humidifier was used. The liquid containing the dissolved and suspended antimicrobial metal-containing material with atomic disorder was placed in the water reservoir of the humidifier. When power was applied to the humidifier, aerosol droplets of dissolved and suspended antimicrobial metal-containing material with atomic disorder were generated and flowed from the output nozzle.

A test chamber was constructed using a stainless steel frame with a transparent plastic covering. The frame was placed on a stainless steel plate. The output nozzle from the humidifier was modified so that the aerosol could be directed into the chamber at a height of approximately 30 cm from the base. The plates and other test samples were placed on the stainless steel plate and exposed to the aerosol for a prescribed length of time.

Solution 1

A solution of antimicrobial metal-containing material with atomic disorder was prepared by immersing 518 sq. inches of Acticoat® burn dressing in 1 L of reverse osmosis water, which was treated with $CO_2$ to maintain a pH of 6.5. After 20 minutes the concentration of silver in the water was 85 mg/mL.

Solution 2

A solution containing 370 mg/mL of silver from a Acticoat® dressing was prepared as follows: 1 L of reverse osmosis water was purged with commercial grade carbon dioxide until the pH was 4.3. Sufficient Acticoat® dressing was added to bring the pH up to 6.5. At that time, the silver concentration was 370 mg/mL.

Solution 3

Ag as $AgNO_3$ was prepared by dissolving 0.157 g of $AgNO_3$ into 1 L of reverse osmosis water and mixed until dissolved. The solution was analyzed by Atomic Absorption Spectroscopy and found to be 102.9 ppm of silver.

Solution 4

Ag as $AgNO_3$ was prepared by dissolving 0.427 of $AgNO_3$ into 1 L of reverse osmosis water and mixed until dissolved. The solution was analyzed by Atomic Absorption Spectroscopy and found to be 295 ppm of silver.

Aerosolization

Petri dishes, containing Mueller Hinton agar, were streaked with 4 h old cultures of *Pseudomonas aeruginosa* or *Staphylococcus aureus*. The plates were then weighed and their exposed outer surfaces were coated with Parafilm to prevent condensation from occurring on these surfaces. These plates were placed in the aerosol chamber uncovered. The ultrasonic nebulizer was then started and run for 53 minutes. The plates were then removed from the chamber, the plastic was removed and the dishes re-weighed so that the amount of moisture loss/gain could be determined.

The plates were then placed in a 35° C. incubator for 16 h. After incubation the pattern and amount of growth was assessed on the plates for both organisms.

Viability Assessment

Three of the six plates made for each organism were tested to determine if the antimicrobial effect was cidal or static in nature. This was accomplished by rinsing or placing a piece of the clear section of agar in the Petri dish plates into Tryptic soy broth in a test tube and incubating for 4 h or 16 h. If the medium turned turbid in 4 h it would indicate that the antimicrobial affect was bacteriostatic in nature. If the organism took more than 16 h to grow, as indicated by turbidity, it was considered an indication that both static and cidal effects occurred. If no growth occurred, the effect was bactericidal.

Results

The results for Solutions 1 and 3 are summarized in the following two table.

| Organism | Antimicrobial Metal-Containing Material With Atomic Disorder | | AgNo₃ | |
|---|---|---|---|---|
| | Ps. Aeruginosa | S. aureus | Ps. Aeruginosa | S. aureus |
| Ag concentration (μg/mL) | 85 | 85 | 99 | 99 |
| pH of test solution | 6.5 | 6.5 | Approx. 6.5 | Approx. 6.5 |
| Exposure time (minutes) | 53 | 53 | 53 | 53 |
| Exposed area (sq. in) | 9.8 | 9.8 | 9.8 | 9.8 |
| Weight gain (g) | 0.8 | 0.8 | 1.05 | 1.05 |
| Growth at 16 h (0–++++) at 48 h | 0 | 0 | 0 | ++++ |
| Viable | 0 | ++ | 0 | ++++ |
| 4 h | No | Yes | No | Yes |
| 16 h | Yes | Yes | Yes | Yes |

The results for Solutions 2 and 4 are summarized in the following two table.

| Organism | Antimicrobial Metal-Containing Material With Atomic Disorder | | AgNo₃ | |
|---|---|---|---|---|
| | Ps. aeruginosa | S. aureus | Ps. aeruginosa | S. aureus |
| Ag concentration (μg/mL) | 370 | 370 | 300 | 300 |
| pH of test solution | 6.5 | 6.5 | Approx. 6.3 | Approx. 6.3 |
| Exposure time (minutes) | 53 | 53 | 53 | 53 |
| Exposed area (sq. in) | 9.8 | 9.8 | 9.8 | 9.8 |
| Weight gain (g) | 1.14 | 1.14 | 1.12 | 1.12 |
| Growth at 16 h | 0 | 0 | 0 | 0 |
| (0–++++) at 48 h Viable | 0 | 0 | 0 | +++ |
| 4 h | No | No | No | No |
| 16 h | No | No | No | N/A |

Discussion

At the low concentration of silver in solution, the Acticoat® dressing generated silver was effective at controlling the growth of both organisms while the silver nitrate only prevented the growth of *Ps. aeruginosa*. Viability tests showed that at the low concentration, neither form of silver was completely bactericidal although the poor growth on the plates treated with antimicrobial metal-containing material with atomic disorder compared to the silver nitrate treated plates suggests that a significant log reduction occurred in the plates treated with the aerosol of antimicrobial metal-containing material with atomic disorder.

At a higher concentration of silver, both antimicrobial metal-containing material with atomic disorder (370 mg/nL) and AgNO₃ (300 mg/mL) were effective at controlling *P. aeruginosa*. Since no re-growth occurred, it is assumed that the agent at this concentration was bactericidal. Antimicrobial silver with atomic disorder was more effective than Ag NO₃ at controlling *S. aureus*. No re-growth occurred on any plates or in the broth indicating a total kill of the organism while, in the Ag NO₃ treatment, a large number of organisms grew at 16 h.

Based on weight gain during aerosol treatments, a dose per unit area can be calculated. In each case for Solution 1, the dose was 8.5 mg/sq. inch, while for Solution 2, the dose was 38 mg/sq. inch. These doses, on a per lung basis, would be less than 10 mg of silver per hour of treatment. Each hour of treatment with antimicrobial silver with atomic disorder aerosols appears to provide at least 48 h of protection. Therefore, the dose per day, from the high concentration treatment, would be about 5 mg or a little less than the silver released by 2 sq. inches of SSD per day.

The most significant advantage of using antimicrobial silver with atomic disorder may be the lack of a toxic action such as NO₃ or sulfadiazine.

Conclusions (1) Aerosols of antimicrobial metal-containing material with atomic disorder transmit the antimicrobial activity of the dressings to remote sites.

(2) Aerosols of antimicrobial metal-containing material with atomic disorder are more effective than comparable concentrations of silver nitrate.

(3) The dose delivered is acceptable and would not appear to be excessive.

(4) No toxic cations (NO₃ or sulfadiazine) are introduced to the patient.

Example 7

(Gels of Antimicrobial Metal-Containing Material With Atomic Disorder)

Gel products of antimicrobial metal-containing material with atomic disorder encompass both wet and dry materials.

A wet gel product of antimicrobial metal-containing material with atomic disorder is a product that provides moisture to a dry skin condition (psoriasis, eczema, acne, wound, etc.) and facilitates autolytic debridement of necrotic tissue. It also delivers the antimicrobial and anti-inflammatory properties of the suspended antimicrobial metal-containing material with atomic disorder powders.

In many instances it is also beneficial to supply biologically active molecules to elicit a specific response such as cell migration, etc. Since these biologically active molecules are susceptible to microbial degradation if not protected, it is beneficial to include them in gels of antimicrobial metal-containing material with atomic disorder that will provide the necessary protection.

Dry gel products of antimicrobial metal-containing material with atomic disorder are physically stabilized (dry or cross-linked) materials that provide lubricious, antimicrobial, antithrombogenic, and anti-inflammatory properties to a variety of implantable, trancutaneous or topically applied devices. The coatings may also provide other benefits such as accelerating or otherwise facilitating tissue integration by creating a favorable environment for cell proliferation. This favorable environment may be created by including cytoconductive agents or anti-adhesion agents such as bone morphogenetic proteins, B-glucan hyaluronic acids in the gel. The gel may be stabilized by cross-linking the gel components (collagen, gelatin, etc.) or by drying the coated materials.

Examples of the primary gelling agents are listed in the following table. Biologically active ingredients that may be used, in any combination with the primary gelling agents, are given in the subsequent table. Materials that should not be used with gels of antimicrobial silver with atomic disorder are given in the final table.

| Material | Percentage Composition |
| --- | --- |
| Carboxymethyl cellulose (CMC) | 0.1-10 |
| Polyvinyl alcohol (PVA) | 0.1-10 |
| Collagen | 0.1-10 |
| Pectin | 0.1-10 |
| Gelatin | 0.1-10 |
| Chitin | 0.1-10 |
| Chitosan | 0.1-10 |
| Alginate | 0.1-10 |
| Poly (α-amino acids) | |
| Polyester | |
| Poly-1-caprolactone | |
| PEG | |
| Cocoa butter | |
| Sepigel | |
| Biologically Active Ingredients | |
| Methyl paraben | <3 |
| Propyl paraben | <3 |
| B-glucan | <3 |
| Hyaluronic acid | <5 |
| Epidermal growth factor | <1 |
| Transforming growth factor | <1 |
| Vascular endothelial growth factor | <1 |
| Interleukins | <1 |
| Heparin | <5 |
| Bone morphogenetic proteins | <1 |
| Non-Compatible Materials | |
| Chloride salts | >0.01 |
| Aldehydes | >0.01 |
| Ketones | >0.01 |
| Long chain alcohols | >0.01 |
| Glycerol | >0.01 |
| Triethanolamine | >0.01 |

Example 8

(Examples of Gels with Antimicrobial Metal-Containing Material With Atomic Disorder)

Gels were prepared as described above in Example 11 in the Treatment of Inflammatory Skin Conditions examples above.

Other embodiments are in the claims.

What is claimed is:

1. An article in suppository form, comprising:
   an atomically disordered, nanocrystalline material comprising a metal and an element, wherein the metal is selected from the group consisting of silver, gold, platinum, palladium and combinations thereof, and the element is selected from the group consisting of oxygen, nitrogen, carbon, boron, sulfur, phosphorus, silicon, a halogen, hydrogen and combinations thereof,
   wherein the atomically disordered, nanocrystalline material contains at least about one atomicpercent of the element and the article contains a pharmaceutically acceptable carrier.

2. The article of claim 1, wherein the nanocrystalline material comprises at most about 90 weight percent of the element.

3. The article of claim 1, wherein the nanocrystalline material is in the form of an agglomerate of clusters of atoms.

4. The article of claim 1, wherein the nanocrystalline material comprises a material selected from the group consisting of antimicrobial materials, antibacterial materials, anti-inflammatory materials, antifungal materials, antiviral materials, anti-autoimmune materials, anti-cancer materials, pro-apoptosis materials, MMP modulating materials, anti-proliferative materials, and combinations thereof.

5. The article of claim 1, wherein the metal is silver.

6. The article of claim 1, wherein the atomically disordered, nanocrystalline material contains a combination of metals selected from the group consisting of silver, gold, platinum and palladium.

* * * * *